United States Patent
Connor

(10) Patent No.: US 9,456,916 B2
(45) Date of Patent: Oct. 4, 2016

(54) DEVICE FOR SELECTIVELY REDUCING ABSORPTION OF UNHEALTHY FOOD

(71) Applicant: Robert A. Connor, Forest Lake, MN (US)

(72) Inventor: Robert A. Connor, Forest Lake, MN (US)

(73) Assignee: Medibotics LLC, Forest Lake, MN (US)

( * ) Notice: Subject to any disclaimer, the term of this patent is extended or adjusted under 35 U.S.C. 154(b) by 679 days.

(21) Appl. No.: 13/797,955

(22) Filed: Mar. 12, 2013

(65) Prior Publication Data

US 2014/0276546 A1    Sep. 18, 2014

(51) Int. Cl.
  *A61F 5/00*     (2006.01)
  *A61M 5/172*    (2006.01)
  *A61M 5/142*    (2006.01)

(52) U.S. Cl.
  CPC ........ *A61F 5/0076* (2013.01); *A61M 5/14276* (2013.01); *A61M 5/1723* (2013.01); *A61F 2005/0016* (2013.01); *A61M 2005/1726* (2013.01); *A61M 2202/0007* (2013.01); *A61M 2202/08* (2013.01); *A61M 2205/0244* (2013.01); *A61M 2205/3303* (2013.01); *A61M 2205/3324* (2013.01); *A61M 2210/1053* (2013.01); *A61M 2210/1057* (2013.01)

(58) Field of Classification Search
  CPC ....... A61M 5/142; A61M 5/172; A61F 5/00; A61F 5/0003; A61F 5/0036; A61F 5/0076
  See application file for complete search history.

(56) References Cited

U.S. PATENT DOCUMENTS

| | | |
|---|---|---|
| 3,411,507 A | 11/1968 | Wingrove |
| 3,818,906 A | 6/1974 | Stubbs |
| 3,856,942 A | 12/1974 | Murphy |
| 3,885,576 A | 5/1975 | Symmes |
| 3,911,099 A | 10/1975 | Defoney et al. |
| 3,972,995 A | 8/1976 | Tsuk et al. |
| 4,039,653 A | 8/1977 | Defoney et al. |
| 4,059,686 A | 11/1977 | Tanaka et al. |
| 4,075,769 A | 2/1978 | Young |
| 4,100,401 A | 7/1978 | Tutt et al. |
| 4,133,315 A | 1/1979 | Berman et al. |
| 4,159,347 A | 6/1979 | Yoshida et al. |
| 4,207,673 A | 6/1980 | DiGirolamo et al. |
| 4,210,637 A | 7/1980 | Wurtman et al. |
| 4,212,079 A | 7/1980 | Segar et al. |
| 4,218,611 A | 8/1980 | Cannon |
| 4,221,959 A | 9/1980 | Sessler |
| 4,292,299 A | 9/1981 | Suzuki et al. |
| 4,310,316 A | 1/1982 | Thomann |
| 4,321,674 A | 3/1982 | Krames et al. |
| 4,355,645 A | 10/1982 | Mitani et al. |
| 4,387,777 A | 6/1983 | Ash |

(Continued)

FOREIGN PATENT DOCUMENTS

| | | |
|---|---|---|
| EP | 1504778 | 2/2005 |
| EP | 1685834 | 8/2006 |

(Continued)

*Primary Examiner* — Matthew F Desanto

(57) ABSTRACT

This invention is a device and method for selectively and automatically reducing absorption of unhealthy food in a person's gastrointestinal tract, while allowing normal absorption of healthy food. In an example, such a device can comprise: a food-identifying sensor; an absorption-reducing substance; an implanted reservoir; and a release-control mechanism that selectively and automatically releases the substance into the person's gastrointestinal tract when the sensor detects that the person is consuming unhealthy food.

18 Claims, 7 Drawing Sheets

(56) References Cited

U.S. PATENT DOCUMENTS

| | | |
|---|---|---|
| 4,416,267 A | 11/1983 | Garren et al. |
| 4,471,771 A | 9/1984 | Brown |
| 4,491,578 A | 1/1985 | Peikin |
| 4,497,798 A | 2/1985 | Lambert |
| 4,519,400 A | 5/1985 | Brenman et al. |
| 4,582,492 A | 4/1986 | Etter et al. |
| 4,592,339 A | 6/1986 | Kuzmak et al. |
| 4,615,697 A | 10/1986 | Robinson |
| 4,637,405 A | 1/1987 | Brenman et al. |
| 4,641,653 A | 2/1987 | Rockey |
| 4,650,218 A | 3/1987 | Hawke |
| 4,686,624 A | 8/1987 | Blum et al. |
| 4,689,235 A | 8/1987 | Barnes et al. |
| 4,694,827 A | 9/1987 | Weiner et al. |
| 4,738,259 A | 4/1988 | Brown et al. |
| 4,740,365 A | 4/1988 | Yukimatsu et al. |
| 4,764,378 A | 8/1988 | Keith et al. |
| 4,796,182 A | 1/1989 | Duboff |
| 4,822,597 A | 4/1989 | Faust et al. |
| 4,823,808 A | 4/1989 | Clegg et al. |
| 4,875,533 A | 10/1989 | Mihara et al. |
| 4,911,256 A | 3/1990 | Attikiouzel |
| 4,914,819 A | 4/1990 | Ash |
| 4,925,446 A | 5/1990 | Garay et al. |
| 4,935,225 A | 6/1990 | Curtis et al. |
| 4,951,197 A | 8/1990 | Mellinger |
| 4,965,553 A | 10/1990 | DelBiondo et al. |
| 4,975,682 A | 12/1990 | Kerr et al. |
| 5,011,472 A | 4/1991 | Aebischer et al. |
| 5,013,716 A | 5/1991 | Cherukuri et al. |
| 5,033,561 A | 7/1991 | Hettinger |
| 5,067,488 A | 11/1991 | Fukada et al. |
| 5,074,868 A | 12/1991 | Kuzmak |
| 5,173,588 A | 12/1992 | Harrah |
| 5,188,104 A | 2/1993 | Wernicke et al. |
| 5,194,003 A | 3/1993 | Garay et al. |
| 5,226,429 A | 7/1993 | Kuzmak |
| 5,233,520 A | 8/1993 | Kretsch et al. |
| 5,234,454 A | 8/1993 | Bangs |
| 5,259,399 A | 11/1993 | Brown |
| 5,263,480 A | 11/1993 | Wernicke et al. |
| 5,263,491 A | 11/1993 | Thornton |
| 5,284,132 A | 2/1994 | Geier |
| 5,290,808 A | 3/1994 | Sofia |
| 5,292,344 A | 3/1994 | Douglas |
| 5,299,356 A | 4/1994 | Maxwell |
| 5,301,679 A | 4/1994 | Taylor |
| 5,318,519 A | 6/1994 | Wilk |
| 5,388,043 A | 2/1995 | Hettinger |
| 5,398,688 A | 3/1995 | Laniado |
| 5,405,641 A | 4/1995 | Kurihara et al. |
| 5,412,564 A | 5/1995 | Ecer |
| 5,421,089 A | 6/1995 | Dubus et al. |
| 5,423,872 A | 6/1995 | Cigaina |
| 5,424,719 A | 6/1995 | Ravid |
| 5,449,368 A | 9/1995 | Kuzmak |
| 5,456,677 A | 10/1995 | Spector |
| 5,472,685 A | 12/1995 | Gaffar |
| 5,478,989 A | 12/1995 | Shepley |
| 5,497,772 A | 3/1996 | Schulman et al. |
| 5,540,730 A | 7/1996 | Terry et al. |
| 5,542,420 A | 8/1996 | Goldman et al. |
| 5,563,850 A | 10/1996 | Hanapole |
| 5,601,604 A | 2/1997 | Vincent |
| 5,603,971 A | 2/1997 | Porzio et al. |
| 5,605,698 A | 2/1997 | Ueno |
| 5,643,207 A | 7/1997 | Rise |
| 5,673,691 A | 10/1997 | Abrams et al. |
| 5,690,691 A | 11/1997 | Chen et al. |
| 5,691,927 A | 11/1997 | Gump |
| 5,704,350 A | 1/1998 | Williams |
| 5,716,385 A | 2/1998 | Mittal et al. |
| 5,720,771 A | 2/1998 | Snell |
| 5,729,479 A | 3/1998 | Golan |
| 5,730,722 A | 3/1998 | Wilk |
| 5,782,798 A | 7/1998 | Rise |
| 5,792,210 A | 8/1998 | Wamubu et al. |
| 5,795,304 A | 8/1998 | Sun et al. |
| 5,817,006 A | 10/1998 | Bergh et al. |
| 5,819,735 A | 10/1998 | Mansfield et al. |
| 5,836,312 A | 11/1998 | Moore |
| 5,836,994 A | 11/1998 | Bourgeois |
| 5,839,901 A | 11/1998 | Karkanen |
| 5,841,115 A | 11/1998 | Shepley |
| 5,858,967 A | 1/1999 | Weigle et al. |
| 5,861,014 A | 1/1999 | Familoni |
| 5,868,141 A | 2/1999 | Ellias |
| 5,890,128 A | 3/1999 | Diaz et al. |
| 5,891,185 A | 4/1999 | Freed et al. |
| 5,908,301 A | 6/1999 | Lutz |
| 5,924,422 A | 7/1999 | Gustafson |
| 5,942,244 A | 8/1999 | Friedman et al. |
| 5,979,449 A | 11/1999 | Steer |
| 5,989,188 A | 11/1999 | Birkhoelzer |
| 5,993,473 A | 11/1999 | Chan et al. |
| 5,995,872 A | 11/1999 | Bourgeois |
| 6,024,281 A | 2/2000 | Shepley |
| 6,032,676 A | 3/2000 | Moore |
| 6,040,531 A | 3/2000 | Miller-Kovach |
| 6,067,991 A | 5/2000 | Forsell |
| 6,083,006 A | 7/2000 | Coffman |
| 6,083,249 A | 7/2000 | Familoni |
| 6,091,992 A | 7/2000 | Bourgeois et al. |
| 6,093,167 A | 7/2000 | Houben et al. |
| 6,095,949 A | 8/2000 | Arai |
| 6,104,955 A | 8/2000 | Bourgeois |
| 6,112,749 A | 9/2000 | Hall et al. |
| 6,115,635 A | 9/2000 | Bourgeois |
| 6,123,980 A | 9/2000 | Pearson et al. |
| 6,135,950 A | 10/2000 | Adams |
| 6,145,503 A | 11/2000 | Smith |
| 6,154,676 A | 11/2000 | Levine |
| 6,159,145 A | 12/2000 | Satoh |
| 6,183,775 B1 | 2/2001 | Ventouras |
| 6,185,452 B1 | 2/2001 | Schulman et al. |
| 6,207,638 B1 | 3/2001 | Portman |
| 6,216,039 B1 | 4/2001 | Bourgeois |
| 6,218,358 B1 | 4/2001 | Firestein et al. |
| 6,224,873 B1 | 5/2001 | Jones |
| 6,230,052 B1 | 5/2001 | Wolff et al. |
| 6,235,274 B1 | 5/2001 | Lou et al. |
| 6,243,607 B1 | 6/2001 | Mintchev et al. |
| 6,248,390 B1 | 6/2001 | Stillman |
| 6,280,761 B1 | 8/2001 | Santus |
| 6,283,914 B1 | 9/2001 | Mansfield et al. |
| 6,285,897 B1 | 9/2001 | Kilcoyne et al. |
| 6,319,523 B1 | 11/2001 | Zhou |
| 6,327,503 B1 | 12/2001 | Familoni |
| 6,334,073 B1 | 12/2001 | Levine |
| 6,336,136 B1 | 1/2002 | Harris |
| 6,341,295 B1 | 1/2002 | Stotler |
| 6,365,128 B1 | 4/2002 | Bennett-Guerrero |
| 6,376,657 B1 | 4/2002 | Van Heerden et al. |
| 6,387,329 B1 | 5/2002 | Lewis et al. |
| 6,387,408 B1 | 5/2002 | Illum et al. |
| 6,413,545 B1 | 7/2002 | Alviar et al. |
| 6,419,903 B1 | 7/2002 | Xu et al. |
| 6,422,243 B1 | 7/2002 | Daram |
| 6,425,862 B1 | 7/2002 | Brown |
| 6,454,785 B2 | 9/2002 | De Hoyos Garza |
| 6,473,368 B1 | 10/2002 | Stanfield |
| 6,478,736 B1 | 11/2002 | Mault |
| 6,485,710 B2 | 11/2002 | Zuckerman |
| 6,488,953 B2 | 12/2002 | Halliday et al. |
| 6,506,152 B1 | 1/2003 | Lackey et al. |
| 6,508,762 B2 | 1/2003 | Karnieli |
| 6,513,532 B2 | 2/2003 | Mault et al. |
| 6,535,764 B2 | 3/2003 | Imran et al. |
| 6,547,801 B1 | 4/2003 | Dargent et al. |
| 6,551,235 B2 | 4/2003 | Forsell |
| 6,553,386 B1 | 4/2003 | Alabaster |
| 6,558,400 B2 | 5/2003 | Deem et al. |
| 6,564,101 B1 | 5/2003 | Zikria |
| 6,571,127 B1 | 5/2003 | Ben-Haim et al. |

(56) References Cited

U.S. PATENT DOCUMENTS

| | | |
|---|---|---|
| 6,571,200 B1 | 5/2003 | Mault |
| 6,572,629 B2 | 6/2003 | Kalloo et al. |
| 6,579,301 B1 | 6/2003 | Bales et al. |
| 6,587,719 B1 | 7/2003 | Barrett et al. |
| 6,591,137 B1 | 7/2003 | Fischell et al. |
| 6,595,929 B2 | 7/2003 | Stivoric et al. |
| 6,600,953 B2 | 7/2003 | Flesler et al. |
| 6,605,038 B1 | 8/2003 | Teller et al. |
| 6,609,025 B2 | 8/2003 | Barrett et al. |
| 6,610,277 B2 | 8/2003 | Zuckerman |
| 6,610,367 B2 | 8/2003 | Lewis et al. |
| 6,627,206 B2 | 9/2003 | Lloyd |
| 6,635,015 B2 | 10/2003 | Sagel |
| 6,675,041 B2 | 1/2004 | Dickinson |
| 6,675,809 B2 | 1/2004 | Stack et al. |
| 6,684,104 B2 | 1/2004 | Gordon et al. |
| 6,694,182 B1 | 2/2004 | Yamazaki et al. |
| 6,715,485 B1 | 4/2004 | Djupesland |
| 6,733,512 B2 | 5/2004 | Mcghan |
| 6,735,477 B2 | 5/2004 | Levine |
| 6,735,479 B2 | 5/2004 | Fabian et al. |
| 6,745,214 B2 | 6/2004 | Inoue et al. |
| 6,760,626 B1 | 7/2004 | Boveja |
| 6,765,488 B2 | 7/2004 | Stanfield |
| 6,826,428 B1 | 11/2004 | Chen et al. |
| 6,832,114 B1 | 12/2004 | Whitehurst et al. |
| 6,856,938 B2 | 2/2005 | Kurtz |
| 6,861,405 B2 | 3/2005 | Desir et al. |
| 6,878,885 B2 | 4/2005 | Miller-Kovach |
| 6,879,859 B1 | 4/2005 | Boveja |
| 6,893,406 B2 | 5/2005 | Takeuchi et al. |
| 6,893,654 B2 | 5/2005 | Pinney et al. |
| 6,902,751 B1 | 6/2005 | Schleifenbaum et al. |
| 6,917,897 B2 | 7/2005 | Mork |
| 6,922,590 B1 | 7/2005 | Whitehurst |
| 6,942,848 B2 | 9/2005 | Nelson et al. |
| 6,949,264 B1 | 9/2005 | Mcgrew et al. |
| 6,950,707 B2 | 9/2005 | Whitehurst |
| 6,966,875 B1 | 11/2005 | Longobardi |
| 6,981,980 B2 | 1/2006 | Sampson et al. |
| 6,993,391 B2 | 1/2006 | Flesler et al. |
| 7,006,871 B1 | 2/2006 | Darvish et al. |
| 7,020,508 B2 | 3/2006 | Stivoric et al. |
| 7,020,531 B1 | 3/2006 | Colliou et al. |
| 7,025,984 B1 | 4/2006 | Jandacek et al. |
| 7,033,373 B2 | 4/2006 | DeLaTorre et al. |
| 7,037,343 B2 | 5/2006 | Imran |
| 7,037,344 B2 | 5/2006 | Kagan et al. |
| 7,041,311 B2 | 5/2006 | Grainger et al. |
| 7,043,295 B2 | 5/2006 | Starkebaum |
| 7,044,739 B2 | 5/2006 | Matson |
| 7,054,690 B2 | 5/2006 | Imran |
| 7,066,945 B2 | 6/2006 | Hashiba et al. |
| 7,072,720 B2 | 7/2006 | Puskas |
| 7,076,305 B2 | 7/2006 | Imran et al. |
| 7,108,680 B2 | 9/2006 | Rohr et al. |
| 7,112,186 B2 | 9/2006 | Shah |
| 7,115,297 B2 | 10/2006 | Stillman |
| 7,120,498 B2 | 10/2006 | Imran et al. |
| 7,121,283 B2 | 10/2006 | Stack et al. |
| 7,122,152 B2 | 10/2006 | Lewis et al. |
| 7,138,107 B2 | 11/2006 | Adams et al. |
| 7,141,071 B2 | 11/2006 | Imran |
| 7,152,607 B2 | 12/2006 | Stack et al. |
| 7,167,750 B2 | 1/2007 | Knudson et al. |
| 7,177,693 B2 | 2/2007 | Starkebaum |
| 7,220,284 B2 | 5/2007 | Kagan et al. |
| 7,229,658 B1 | 6/2007 | Inoue et al. |
| 7,236,822 B2 | 6/2007 | Dobak |
| 7,238,380 B2 | 7/2007 | Stillman |
| 7,239,912 B2 | 7/2007 | Dobak |
| 7,241,880 B2 | 7/2007 | Adler et al. |
| 7,247,023 B2 | 7/2007 | Peplinski et al. |
| 7,247,323 B2 | 7/2007 | George et al. |
| 7,261,690 B2 | 8/2007 | Teller et al. |
| 7,276,229 B1 | 10/2007 | Baker et al. |
| 7,285,090 B2 | 10/2007 | Stivoric et al. |
| 7,288,099 B2 | 10/2007 | Deem et al. |
| 7,288,101 B2 | 10/2007 | Deem et al. |
| 7,299,091 B2 | 11/2007 | Barrett et al. |
| 7,330,753 B2 | 2/2008 | Policker et al. |
| 7,354,454 B2 | 4/2008 | Stack et al. |
| 7,361,141 B2 | 4/2008 | Nissila et al. |
| 7,402,400 B2 | 7/2008 | Zuker et al. |
| 7,409,647 B2 | 8/2008 | Elber et al. |
| 7,430,450 B2 | 9/2008 | Imran |
| 7,437,195 B2 | 10/2008 | Policker et al. |
| 7,440,806 B1 | 10/2008 | Whitehurst et al. |
| 7,454,002 B1 | 11/2008 | Gardner et al. |
| 7,470,251 B2 | 12/2008 | Shah |
| 7,477,944 B1 | 1/2009 | Whitehurst et al. |
| 7,477,947 B2 | 1/2009 | Pines et al. |
| 7,483,746 B2 | 1/2009 | Lee et al. |
| 7,493,171 B1 | 2/2009 | Whitehurst et al. |
| 7,500,937 B2 | 3/2009 | Hercules |
| 7,502,649 B2 | 3/2009 | Ben-Haim et al. |
| 7,503,922 B2 | 3/2009 | Deem et al. |
| 7,509,174 B2 | 3/2009 | Imran et al. |
| 7,510,559 B2 | 3/2009 | Deem et al. |
| 7,512,442 B2 | 3/2009 | Flesler et al. |
| 7,524,877 B2 | 4/2009 | Rosenfeld et al. |
| 7,529,582 B1 | 5/2009 | Dilorenzo |
| 7,541,356 B2 | 6/2009 | Rosenfeld et al. |
| 7,551,964 B2 | 6/2009 | Dobak |
| 7,558,629 B2 | 7/2009 | Keimel et al. |
| 7,580,751 B2 | 8/2009 | Starkebaum |
| 7,590,452 B2 | 9/2009 | Imran et al. |
| 7,595,023 B2 | 9/2009 | Lewis et al. |
| 7,599,736 B2 | 10/2009 | Dilorenzo |
| 7,601,178 B2 | 10/2009 | Imran |
| 7,620,454 B2 | 11/2009 | Dinsmoor et al. |
| 7,632,517 B2 | 12/2009 | Dugger et al. |
| 7,643,887 B2 | 1/2010 | Imran |
| 7,648,479 B2 | 1/2010 | Solovay et al. |
| 7,651,868 B2 | 1/2010 | Mcdevitt et al. |
| 7,657,310 B2 | 2/2010 | Buras |
| 7,664,551 B2 | 2/2010 | Cigaina |
| 7,682,306 B2 | 3/2010 | Shah |
| 7,689,276 B2 | 3/2010 | Dobak |
| 7,689,277 B2 | 3/2010 | Dobak |
| 7,689,437 B1 | 3/2010 | Teller et al. |
| 7,695,446 B2 | 4/2010 | Levine et al. |
| 7,699,863 B2 | 4/2010 | Marco et al. |
| 7,702,386 B2 | 4/2010 | Dobak et al. |
| 7,702,394 B2 | 4/2010 | Imran |
| 7,717,843 B2 | 5/2010 | Balbierz et al. |
| 7,727,147 B1 | 6/2010 | Osorio et al. |
| 7,727,546 B2 | 6/2010 | Moneymaker et al. |
| 7,729,771 B2 | 6/2010 | Knudson et al. |
| 7,738,961 B2 | 6/2010 | Sharma |
| 7,740,624 B2 | 6/2010 | Klein et al. |
| 7,742,818 B2 | 6/2010 | Dinsmoor et al. |
| 7,753,870 B2 | 7/2010 | Demarais et al. |
| 7,756,582 B2 | 7/2010 | Imran et al. |
| 7,758,493 B2 | 7/2010 | Gingras |
| 7,769,635 B2 | 8/2010 | Simons-Nikolova |
| 7,771,382 B2 | 8/2010 | Levine et al. |
| 7,775,966 B2 | 8/2010 | Dlugos et al. |
| 7,775,967 B2 | 8/2010 | Gertner |
| 7,785,291 B2 | 8/2010 | Marco et al. |
| 7,790,671 B2 | 9/2010 | Stojanovic-Susulic |
| 7,794,425 B2 | 9/2010 | Gobel |
| 7,794,447 B2 | 9/2010 | Dann et al. |
| 7,798,954 B2 | 9/2010 | Birk et al. |
| 7,803,195 B2 | 9/2010 | Levy et al. |
| 7,815,629 B2 | 10/2010 | Klein et al. |
| 7,820,208 B2 | 10/2010 | Hirsch |
| 7,832,407 B2 | 11/2010 | Gertner |
| 7,833,279 B2 | 11/2010 | Knudson et al. |
| 7,833,280 B2 | 11/2010 | Stack et al. |
| 7,835,796 B2 | 11/2010 | Maschino et al. |
| 7,837,643 B2 | 11/2010 | Levine et al. |
| 7,837,669 B2 | 11/2010 | Dann et al. |
| 7,840,269 B2 | 11/2010 | Policker et al. |

(56) References Cited

U.S. PATENT DOCUMENTS

| | | | |
|---|---|---|---|
| 7,840,278 B1 | 11/2010 | Puskas | |
| 7,841,978 B2 | 11/2010 | Gertner | |
| 7,846,138 B2 | 12/2010 | Dann et al. | |
| 7,851,000 B2 | 12/2010 | Boghani et al. | |
| 7,851,005 B2 | 12/2010 | Bingley et al. | |
| 7,851,006 B2 | 12/2010 | Bingley et al. | |
| 7,854,745 B2 | 12/2010 | Brister et al. | |
| 7,857,730 B2 | 12/2010 | Dugan | |
| 7,862,574 B2 | 1/2011 | Deem et al. | |
| 7,879,068 B2 | 2/2011 | Dlugos et al. | |
| 7,879,376 B2 | 2/2011 | Boghani et al. | |
| 7,881,797 B2 | 2/2011 | Griffin et al. | |
| 7,882,150 B2 | 2/2011 | Badyal | |
| 7,909,754 B2 | 3/2011 | Hassler et al. | |
| 7,909,838 B2 | 3/2011 | Deem et al. | |
| 7,909,839 B2 | 3/2011 | Fields | |
| 7,914,468 B2 | 3/2011 | Shalon et al. | |
| 7,931,694 B2 | 4/2011 | Imran | |
| 7,935,065 B2 | 5/2011 | Martin et al. | |
| 7,935,073 B2 | 5/2011 | Levine et al. | |
| 7,937,145 B2 | 5/2011 | Dobak | |
| 7,938,769 B2 | 5/2011 | Gertner | |
| 7,941,221 B2 | 5/2011 | Foley | |
| 7,945,323 B2 | 5/2011 | Jaax et al. | |
| 7,949,506 B1 | 5/2011 | Hill et al. | |
| 7,959,567 B2 | 6/2011 | Stivoric et al. | |
| 7,963,907 B2 | 6/2011 | Gertner | |
| 7,967,780 B2 | 6/2011 | Goebel | |
| 7,972,346 B2 | 7/2011 | Bachmann et al. | |
| 7,972,618 B2 | 7/2011 | Fuisz et al. | |
| 7,974,672 B2 | 7/2011 | Shults et al. | |
| 7,977,060 B2 | 7/2011 | Zuker et al. | |
| 7,979,127 B2 | 7/2011 | Imran | |
| 7,981,162 B2 | 7/2011 | Stack et al. | |
| 7,986,995 B2 | 7/2011 | Knudson et al. | |
| 7,988,617 B2 | 8/2011 | Gertner | |
| 7,988,630 B1 | 8/2011 | Osorio et al. | |
| 7,999,674 B2 | 8/2011 | Kamen | |
| 8,001,974 B2 | 8/2011 | Makower et al. | |
| 8,002,758 B2 | 8/2011 | Kamen et al. | |
| 8,010,204 B2 | 8/2011 | Knudson et al. | |
| 8,012,140 B1 | 9/2011 | Kagan et al. | |
| 8,016,744 B2 | 9/2011 | Dlugos et al. | |
| 8,016,745 B2 | 9/2011 | Hassler et al. | |
| 8,019,421 B2 | 9/2011 | Darvish et al. | |
| 8,029,455 B2 | 10/2011 | Stack et al. | |
| 8,034,065 B2 | 10/2011 | Coe et al. | |
| 8,034,118 B2 | 10/2011 | Imran | |
| 8,043,206 B2 | 10/2011 | Birk | |
| 8,048,169 B2 | 11/2011 | Burnett et al. | |
| 8,057,420 B2 | 11/2011 | Meade et al. | |
| 8,060,220 B2 | 11/2011 | Liebergesell et al. | |
| 8,062,285 B2 | 11/2011 | Langloss et al. | |
| 8,066,689 B2 | 11/2011 | Mitelberg et al. | |
| 8,066,780 B2 | 11/2011 | Chen et al. | |
| 8,067,185 B2 | 11/2011 | Zoller et al. | |
| 8,070,673 B2 | 12/2011 | Gertner et al. | |
| 8,070,743 B2 | 12/2011 | Kagan et al. | |
| 8,070,768 B2 | 12/2011 | Kim et al. | |
| 8,073,707 B2 | 12/2011 | Teller et al. | |
| 8,075,451 B2 | 12/2011 | Dugan | |
| 8,075,577 B2 | 12/2011 | Deem et al. | |
| 8,080,022 B2 | 12/2011 | Deem et al. | |
| 8,080,025 B2 | 12/2011 | Deem et al. | |
| 8,082,039 B2 | 12/2011 | Kim et al. | |
| 8,083,756 B2 | 12/2011 | Gannoe et al. | |
| 8,083,757 B2 | 12/2011 | Gannoe et al. | |
| 8,087,937 B2 | 1/2012 | Peplinski et al. | |
| 8,095,218 B2 | 1/2012 | Gross et al. | |
| 8,095,219 B2 | 1/2012 | Lee et al. | |
| 8,100,870 B2 | 1/2012 | Marcotte et al. | |
| 8,109,895 B2 | 2/2012 | Williams et al. | |
| 8,109,920 B2 | 2/2012 | Boyden et al. | |
| 8,112,281 B2 | 2/2012 | Yeung et al. | |
| 8,119,359 B2 | 2/2012 | Adler et al. | |
| 8,123,765 B2 | 2/2012 | Deem et al. | |
| 8,135,470 B2 | 3/2012 | Keimel et al. | |
| 8,137,261 B2 | 3/2012 | Kierath et al. | |
| 8,137,301 B2 | 3/2012 | Levine et al. | |
| 8,137,366 B2 | 3/2012 | Deem et al. | |
| 8,137,367 B2 | 3/2012 | Deem et al. | |
| 8,142,469 B2 | 3/2012 | Sosnowski et al. | |
| 8,142,513 B2 | 3/2012 | Shalon et al. | |
| 8,143,062 B2 | 3/2012 | Hirsch | |
| 8,143,215 B2 | 3/2012 | Hirsch | |
| 8,145,299 B2 | 3/2012 | Dobak | |
| 8,147,441 B2 | 4/2012 | Gannoe et al. | |
| 8,150,508 B2 | 4/2012 | Craig | |
| 8,157,731 B2 | 4/2012 | Teller et al. | |
| 8,158,082 B2 | 4/2012 | Imran | |
| 8,162,871 B2 | 4/2012 | Levine et al. | |
| 8,162,969 B2 | 4/2012 | Brister et al. | |
| 8,173,113 B1 | 5/2012 | Scholz et al. | |
| 8,177,853 B2 | 5/2012 | Stack et al. | |
| 8,180,592 B2 | 5/2012 | Yuen et al. | |
| 8,181,655 B2 | 5/2012 | Bardach et al. | |
| 8,182,459 B2 | 5/2012 | Dann et al. | |
| 8,185,206 B2 | 5/2012 | Starkebaum et al. | |
| 8,187,289 B2 | 5/2012 | Tacchino et al. | |
| 8,187,297 B2 | 5/2012 | Makower et al. | |
| 8,192,350 B2 | 6/2012 | Ortiz et al. | |
| 8,192,455 B2 | 6/2012 | Brazzini et al. | |
| 8,197,498 B2 | 6/2012 | Coleman et al. | |
| 8,198,048 B2 | 6/2012 | Zuker et al. | |
| 8,202,291 B1 | 6/2012 | Brister et al. | |
| 8,206,456 B2 | 6/2012 | Stack et al. | |
| 8,209,037 B2 | 6/2012 | Laufer et al. | |
| 8,211,128 B1 | 7/2012 | Facundus et al. | |
| 8,211,186 B2 | 7/2012 | Belhe et al. | |
| 8,214,049 B2 | 7/2012 | Brynelsen et al. | |
| 8,216,158 B2 | 7/2012 | Johnson | |
| 8,217,001 B2 | 7/2012 | Cowley et al. | |
| 8,219,171 B2 | 7/2012 | Benoist | |
| 8,226,593 B2 | 7/2012 | Graham et al. | |
| 8,226,602 B2 | 7/2012 | Quijana et al. | |
| 8,229,676 B2 | 7/2012 | Hyde et al. | |
| 8,230,865 B2 | 7/2012 | Shalon | |
| 8,233,954 B2 | 7/2012 | Kling et al. | |
| 8,236,023 B2 | 8/2012 | Birk et al. | |
| 8,236,242 B2 | 8/2012 | Drucker et al. | |
| 8,236,285 B2 | 8/2012 | Dugger et al. | |
| 8,236,348 B2 | 8/2012 | Gin et al. | |
| 8,239,027 B2 | 8/2012 | Imran | |
| 8,241,202 B2 | 8/2012 | Balbierz et al. | |
| 8,251,888 B2 | 8/2012 | Roslin et al. | |
| 8,252,009 B2 | 8/2012 | Weller et al. | |
| 8,252,744 B2 | 8/2012 | Stojanovic-Susulic et al. | |
| 8,265,758 B2 | 9/2012 | Policker et al. | |
| 8,267,888 B2 | 9/2012 | Marco et al. | |
| 8,275,438 B2 | 9/2012 | Simpson et al. | |
| 8,280,505 B2 | 10/2012 | Craig | |
| 8,282,598 B2 | 10/2012 | Belhe et al. | |
| 8,282,623 B2 | 10/2012 | Klein et al. | |
| 8,282,666 B2 | 10/2012 | Birk | |
| 8,285,488 B2 | 10/2012 | Hyde et al. | |
| 8,287,453 B2 | 10/2012 | Li et al. | |
| 8,287,554 B2 | 10/2012 | Cerier et al. | |
| 8,287,898 B2 | 10/2012 | Jandacek et al. | |
| 8,290,712 B2 | 10/2012 | Hyde et al. | |
| 8,292,800 B2 | 10/2012 | Stone et al. | |
| 8,292,911 B2 | 10/2012 | Brister et al. | |
| 8,295,926 B2 | 10/2012 | Dobak | |
| 8,295,932 B2 | 10/2012 | Bitton et al. | |
| 8,298,142 B2 | 10/2012 | Simpson et al. | |
| 8,299,930 B2 | 10/2012 | Schmid-Schonbein | |
| 8,301,256 B2 | 10/2012 | Policker et al. | |
| 8,303,573 B2 | 11/2012 | Boyden et al. | |
| 8,303,669 B2 | 11/2012 | Meade et al. | |
| 8,308,630 B2 | 11/2012 | Birk et al. | |
| 8,310,368 B2 | 11/2012 | Hoover et al. | |
| 8,311,769 B2 | 11/2012 | Yuen et al. | |
| 8,311,770 B2 | 11/2012 | Yuen et al. | |
| 8,314,224 B2 | 11/2012 | Adler et al. | |
| 8,317,677 B2 | 11/2012 | Bertolote et al. | |

(56) References Cited

U.S. PATENT DOCUMENTS

| | | |
|---|---|---|
| 8,321,030 B2 | 11/2012 | Maniak et al. |
| 8,321,141 B2 | 11/2012 | Hyde et al. |
| 8,323,180 B2 | 12/2012 | Birk et al. |
| 8,328,420 B2 | 12/2012 | Abreu |
| 8,333,754 B2 | 12/2012 | Boyden et al. |
| 8,334,367 B2 | 12/2012 | Adler |
| 8,337,566 B2 | 12/2012 | Stack et al. |
| 8,340,772 B2 | 12/2012 | Vase et al. |
| 8,345,930 B2 | 1/2013 | Tamrakar et al. |
| 8,346,363 B2 | 1/2013 | Darvish et al. |
| 8,355,875 B2 | 1/2013 | Hyde et al. |
| 8,363,913 B2 | 1/2013 | Boushey et al. |
| 2001/0037127 A1 | 11/2001 | De Hoyos Garza |
| 2001/0049470 A1 | 12/2001 | Mault et al. |
| 2002/0022774 A1 | 2/2002 | Karnieli |
| 2002/0027164 A1 | 3/2002 | Mault et al. |
| 2002/0047867 A1 | 4/2002 | Mault et al. |
| 2002/0049482 A1 | 4/2002 | Fabian et al. |
| 2002/0072780 A1 | 6/2002 | Foley |
| 2002/0109600 A1 | 8/2002 | Mault et al. |
| 2002/0124017 A1 | 9/2002 | Mault |
| 2002/0133378 A1 | 9/2002 | Mault et al. |
| 2002/0156351 A1 | 10/2002 | Sagel |
| 2002/0187204 A1 | 12/2002 | Alviar et al. |
| 2003/0009202 A1 | 1/2003 | Levine |
| 2003/0021822 A1 | 1/2003 | Lloyd |
| 2003/0059737 A1 | 3/2003 | Hall |
| 2003/0065257 A1 | 4/2003 | Mault et al. |
| 2003/0076983 A1 | 4/2003 | Cox |
| 2003/0095936 A1 | 5/2003 | Light |
| 2003/0113310 A1 | 6/2003 | Van Laere et al. |
| 2003/0152607 A1 | 8/2003 | Mault |
| 2003/0163354 A1 | 8/2003 | Shamoun |
| 2003/0165799 A1 | 9/2003 | Bisogno |
| 2003/0167024 A1 | 9/2003 | Imran et al. |
| 2003/0171711 A1 | 9/2003 | Rohr et al. |
| 2003/0208110 A1 | 11/2003 | Mault et al. |
| 2003/0219513 A1 | 11/2003 | Gordon |
| 2004/0034289 A1 | 2/2004 | Teller et al. |
| 2004/0044376 A1 | 3/2004 | Flesler et al. |
| 2004/0059393 A1 | 3/2004 | Policker et al. |
| 2004/0071801 A1 | 4/2004 | Edell et al. |
| 2004/0073142 A1 | 4/2004 | Takeuchi et al. |
| 2004/0088023 A1 | 5/2004 | Imran et al. |
| 2004/0109886 A1 | 6/2004 | Rigby |
| 2004/0122452 A1 | 6/2004 | Deem et al. |
| 2004/0122453 A1 | 6/2004 | Deem et al. |
| 2004/0131661 A1 | 7/2004 | Auffret et al. |
| 2004/0133081 A1 | 7/2004 | Teller et al. |
| 2004/0147816 A1 | 7/2004 | Policker et al. |
| 2004/0151771 A1 | 8/2004 | Gin et al. |
| 2004/0152957 A1 | 8/2004 | Stivoric et al. |
| 2004/0156920 A1 | 8/2004 | Kane |
| 2004/0162595 A1 | 8/2004 | Foley |
| 2004/0167583 A1 | 8/2004 | Knudson et al. |
| 2004/0172142 A1 | 9/2004 | Stack et al. |
| 2004/0186528 A1 | 9/2004 | Ries et al. |
| 2004/0192760 A1 | 9/2004 | Whittle et al. |
| 2004/0231299 A1 | 11/2004 | Yakushigawa et al. |
| 2004/0243195 A1 | 12/2004 | Imran et al. |
| 2004/0247669 A1 | 12/2004 | Gin et al. |
| 2004/0247702 A1 | 12/2004 | Rajendran et al. |
| 2005/0004436 A1 | 1/2005 | Nissila et al. |
| 2005/0008994 A1 | 1/2005 | Bisogno |
| 2005/0014111 A1 | 1/2005 | Matson |
| 2005/0037031 A1 | 2/2005 | Jackson |
| 2005/0038415 A1 | 2/2005 | Rohr et al. |
| 2005/0053555 A1 | 3/2005 | Pederson |
| 2005/0065571 A1 | 3/2005 | Imran |
| 2005/0090873 A1 | 4/2005 | Imran |
| 2005/0096514 A1 | 5/2005 | Starkebaum |
| 2005/0096637 A1* | 5/2005 | Heruth ............... G01N 33/5088 604/891.1 |
| 2005/0112149 A1 | 5/2005 | Belote et al. |
| 2005/0113649 A1 | 5/2005 | Bergantino |
| 2005/0113650 A1 | 5/2005 | Pacione et al. |
| 2005/0146419 A1 | 7/2005 | Porter |
| 2005/0149142 A1 | 7/2005 | Starkebaum |
| 2005/0222638 A1 | 10/2005 | Foley et al. |
| 2005/0240253 A1 | 10/2005 | Tyler et al. |
| 2005/0247213 A1 | 11/2005 | Slilaty |
| 2005/0263160 A1 | 12/2005 | Utley et al. |
| 2005/0266385 A1 | 12/2005 | Bisogno |
| 2005/0277900 A1 | 12/2005 | Klein et al. |
| 2005/0283096 A1 | 12/2005 | Chau et al. |
| 2005/0287495 A1 | 12/2005 | Longley |
| 2006/0015016 A1 | 1/2006 | Thornton |
| 2006/0020298 A1 | 1/2006 | Camilleri et al. |
| 2006/0031102 A1 | 2/2006 | Teller et al. |
| 2006/0036395 A1 | 2/2006 | Shaya et al. |
| 2006/0064037 A1 | 3/2006 | Shalon et al. |
| 2006/0074459 A1 | 4/2006 | Flesler et al. |
| 2006/0074716 A1 | 4/2006 | Tilles et al. |
| 2006/0079944 A1 | 4/2006 | Imran |
| 2006/0089571 A1 | 4/2006 | Gertner |
| 2006/0089699 A1 | 4/2006 | Imran |
| 2006/0105068 A1 | 5/2006 | Fleischner |
| 2006/0106332 A1 | 5/2006 | Knudson et al. |
| 2006/0122468 A1 | 6/2006 | Tavor |
| 2006/0122474 A1 | 6/2006 | Teller et al. |
| 2006/0129201 A1 | 6/2006 | Lee et al. |
| 2006/0173238 A1 | 8/2006 | Starkebaum |
| 2006/0173508 A1 | 8/2006 | Stone et al. |
| 2006/0189853 A1 | 8/2006 | Brown |
| 2006/0193795 A1 | 8/2006 | Zuckerman |
| 2006/0197670 A1 | 9/2006 | Breibart |
| 2006/0199997 A1 | 9/2006 | Hassler et al. |
| 2006/0206169 A1 | 9/2006 | Schuler |
| 2006/0229504 A1 | 10/2006 | Johnson |
| 2006/0235448 A1 | 10/2006 | Roslin et al. |
| 2006/0235487 A1 | 10/2006 | Meyer et al. |
| 2006/0252983 A1 | 11/2006 | Lembo et al. |
| 2006/0263750 A1 | 11/2006 | Gordon |
| 2006/0264699 A1 | 11/2006 | Gertner |
| 2006/0264730 A1 | 11/2006 | Stivoric et al. |
| 2007/0016262 A1 | 1/2007 | Gross et al. |
| 2007/0021979 A1 | 1/2007 | Cosentino et al. |
| 2007/0027366 A1 | 2/2007 | Osburn |
| 2007/0027493 A1 | 2/2007 | Ben-Haim et al. |
| 2007/0027498 A1 | 2/2007 | Maschino et al. |
| 2007/0028453 A1 | 2/2007 | Crow |
| 2007/0030339 A1 | 2/2007 | Findlay et al. |
| 2007/0042058 A1 | 2/2007 | George et al. |
| 2007/0048369 A1 | 3/2007 | Foreman et al. |
| 2007/0050058 A1 | 3/2007 | Zuziak et al. |
| 2007/0059672 A1 | 3/2007 | Shaw |
| 2007/0060812 A1 | 3/2007 | Harel et al. |
| 2007/0077300 A1 | 4/2007 | Wynn et al. |
| 2007/0082843 A1 | 4/2007 | Stojanovic-Susulic |
| 2007/0089335 A1 | 4/2007 | Smith et al. |
| 2007/0093910 A1 | 4/2007 | Imran |
| 2007/0098856 A1 | 5/2007 | LePine |
| 2007/0104783 A1 | 5/2007 | Domb et al. |
| 2007/0104805 A1 | 5/2007 | Udell |
| 2007/0106129 A1 | 5/2007 | Srivathsa et al. |
| 2007/0106138 A1 | 5/2007 | Beiski et al. |
| 2007/0135846 A1 | 6/2007 | Knudson et al. |
| 2007/0149994 A1 | 6/2007 | Sosnowski et al. |
| 2007/0150021 A1 | 6/2007 | Chen et al. |
| 2007/0156013 A1 | 7/2007 | Birk |
| 2007/0160735 A1 | 7/2007 | Stillman |
| 2007/0162085 A1 | 7/2007 | DiLorenzo |
| 2007/0173703 A1 | 7/2007 | Lee et al. |
| 2007/0179355 A1 | 8/2007 | Rosen |
| 2007/0179556 A1 | 8/2007 | Ben-Haim et al. |
| 2007/0196436 A1 | 8/2007 | Abrahamse et al. |
| 2007/0203521 A1 | 8/2007 | Dobak et al. |
| 2007/0207199 A1 | 9/2007 | Sogin |
| 2007/0208593 A1 | 9/2007 | Hercules |
| 2007/0250083 A1 | 10/2007 | Deem et al. |
| 2007/0255334 A1 | 11/2007 | Keimel et al. |
| 2007/0265598 A1 | 11/2007 | Karasik |
| 2007/0265645 A1 | 11/2007 | Birk et al. |
| 2007/0265646 A1 | 11/2007 | Mccoy et al. |

(56) References Cited

U.S. PATENT DOCUMENTS

| | | |
|---|---|---|
| 2007/0276293 A1 | 11/2007 | Gertner |
| 2007/0293885 A1 | 12/2007 | Binmoeller |
| 2007/0299320 A1 | 12/2007 | Policker et al. |
| 2008/0014327 A1 | 1/2008 | Stillman |
| 2008/0021512 A1 | 1/2008 | Knudson et al. |
| 2008/0033345 A1 | 2/2008 | Langloss et al. |
| 2008/0033364 A1 | 2/2008 | Kamen et al. |
| 2008/0033365 A1 | 2/2008 | Solovay et al. |
| 2008/0039809 A1 | 2/2008 | Kamen et al. |
| 2008/0044797 A1 | 2/2008 | Bardach et al. |
| 2008/0046013 A1 | 2/2008 | Lozano |
| 2008/0051824 A1 | 2/2008 | Gertner |
| 2008/0058887 A1 | 3/2008 | Griffin et al. |
| 2008/0065168 A1 | 3/2008 | Bitton et al. |
| 2008/0075813 A1 | 3/2008 | Smith et al. |
| 2008/0086179 A1 | 4/2008 | Sharma |
| 2008/0091146 A1 | 4/2008 | Solovay et al. |
| 2008/0102143 A1 | 5/2008 | Freis et al. |
| 2008/0137486 A1 | 6/2008 | Czarenk et al. |
| 2008/0138447 A1 | 6/2008 | Riggins et al. |
| 2008/0141282 A1 | 6/2008 | Elber et al. |
| 2008/0147002 A1 | 6/2008 | Gertner |
| 2008/0152705 A1 | 6/2008 | Udell et al. |
| 2008/0154191 A1 | 6/2008 | Gobel |
| 2008/0161654 A1 | 7/2008 | Teller et al. |
| 2008/0161655 A1 | 7/2008 | Teller et al. |
| 2008/0161717 A1 | 7/2008 | Gertner |
| 2008/0167536 A1 | 7/2008 | Teller et al. |
| 2008/0167537 A1 | 7/2008 | Teller et al. |
| 2008/0167538 A1 | 7/2008 | Teller et al. |
| 2008/0167539 A1 | 7/2008 | Teller et al. |
| 2008/0171920 A1 | 7/2008 | Teller et al. |
| 2008/0171921 A1 | 7/2008 | Teller et al. |
| 2008/0171922 A1 | 7/2008 | Teller et al. |
| 2008/0172072 A1 | 7/2008 | Pool et al. |
| 2008/0183238 A1 | 7/2008 | Chen |
| 2008/0188766 A1 | 8/2008 | Gertner |
| 2008/0195171 A1 | 8/2008 | Sharma |
| 2008/0208240 A1 | 8/2008 | Paz |
| 2008/0221644 A1 | 9/2008 | Vallapureddy et al. |
| 2008/0243071 A1 | 10/2008 | Quijano et al. |
| 2008/0255093 A1 | 10/2008 | Tam et al. |
| 2008/0255955 A1 | 10/2008 | Simons-Nikolova |
| 2008/0262411 A1 | 10/2008 | Dobak |
| 2008/0262557 A1 | 10/2008 | Brown |
| 2008/0267444 A1 | 10/2008 | Simons-Nikolova |
| 2008/0270947 A1 | 10/2008 | Elber et al. |
| 2008/0275309 A1 | 11/2008 | Stivoric et al. |
| 2008/0275484 A1 | 11/2008 | Gertner |
| 2008/0276461 A1 | 11/2008 | Gold |
| 2008/0319471 A1 | 12/2008 | Sosnowski et al. |
| 2009/0012433 A1 | 1/2009 | Fernstrom et al. |
| 2009/0018594 A1 | 1/2009 | Laufer et al. |
| 2009/0018605 A1 | 1/2009 | Imran et al. |
| 2009/0018606 A1 | 1/2009 | Sparks et al. |
| 2009/0030474 A1 | 1/2009 | Brynelsen et al. |
| 2009/0030475 A1 | 1/2009 | Brynelsen et al. |
| 2009/0062725 A1 | 3/2009 | Goebel |
| 2009/0062881 A1 | 3/2009 | Gross et al. |
| 2009/0081291 A1 | 3/2009 | Gin et al. |
| 2009/0088816 A1 | 4/2009 | Harel et al. |
| 2009/0093767 A1 | 4/2009 | Kelleher |
| 2009/0112800 A1 | 4/2009 | Athsani |
| 2009/0118797 A1 | 5/2009 | Kliger et al. |
| 2009/0123380 A1 | 5/2009 | Hirsch |
| 2009/0123524 A1 | 5/2009 | Hirsch |
| 2009/0123579 A1 | 5/2009 | Hirsch |
| 2009/0130178 A1 | 5/2009 | Oronsky et al. |
| 2009/0131968 A1 | 5/2009 | Birk |
| 2009/0149910 A1 | 6/2009 | Imran et al. |
| 2009/0157106 A1 | 6/2009 | Marcotte et al. |
| 2009/0171375 A1 | 7/2009 | Coe et al. |
| 2009/0176526 A1 | 7/2009 | Altman |
| 2009/0177068 A1 | 7/2009 | Stivoric et al. |
| 2009/0182303 A1* | 7/2009 | Walak ............... A61F 5/0013 514/1.1 |
| 2009/0191514 A1 | 7/2009 | Barnow |
| 2009/0192534 A1 | 7/2009 | Ortiz et al. |
| 2009/0192535 A1 | 7/2009 | Kasic |
| 2009/0197963 A1 | 8/2009 | Llewellyn |
| 2009/0204131 A1 | 8/2009 | Ortiz et al. |
| 2009/0204132 A1 | 8/2009 | Ortiz et al. |
| 2009/0214445 A1 | 8/2009 | Boghani et al. |
| 2009/0216255 A1 | 8/2009 | Coe et al. |
| 2009/0219159 A1 | 9/2009 | Morgenstern |
| 2009/0240194 A1 | 9/2009 | Keimel et al. |
| 2009/0240340 A1 | 9/2009 | Levine et al. |
| 2009/0247992 A1 | 10/2009 | Shalon et al. |
| 2009/0248171 A1 | 10/2009 | Levine et al. |
| 2009/0253105 A1 | 10/2009 | Lepine |
| 2009/0259246 A1 | 10/2009 | Eskaros et al. |
| 2009/0259274 A1 | 10/2009 | Simon et al. |
| 2009/0259279 A1 | 10/2009 | Dobak |
| 2009/0261987 A1 | 10/2009 | Sun |
| 2009/0264951 A1 | 10/2009 | Sharma |
| 2009/0270904 A1 | 10/2009 | Birk et al. |
| 2009/0275973 A1 | 11/2009 | Chen et al. |
| 2009/0281449 A1 | 11/2009 | Thrower et al. |
| 2009/0299434 A1 | 12/2009 | Imran et al. |
| 2009/0306462 A1 | 12/2009 | Lechner |
| 2009/0312785 A1 | 12/2009 | Stone et al. |
| 2009/0312817 A1 | 12/2009 | Hogle et al. |
| 2010/0004755 A1 | 1/2010 | Imran |
| 2010/0049274 A1 | 2/2010 | Cholette |
| 2010/0055245 A1 | 3/2010 | Havekotte et al. |
| 2010/0057564 A1 | 3/2010 | Godsey et al. |
| 2010/0062119 A1 | 3/2010 | Miller-Kovach |
| 2010/0062402 A1 | 3/2010 | Miller-Kovach |
| 2010/0076345 A1 | 3/2010 | Soffer et al. |
| 2010/0079291 A1 | 4/2010 | Kroll et al. |
| 2010/0080875 A1 | 4/2010 | Miller-Kovach |
| 2010/0087706 A1 | 4/2010 | Syed et al. |
| 2010/0094374 A1 | 4/2010 | Imran |
| 2010/0094375 A1 | 4/2010 | Donders et al. |
| 2010/0098783 A1 | 4/2010 | Sommerfeld et al. |
| 2010/0100116 A1 | 4/2010 | Brister et al. |
| 2010/0100117 A1 | 4/2010 | Brister et al. |
| 2010/0106130 A1 | 4/2010 | Solovay et al. |
| 2010/0106131 A1 | 4/2010 | Klein et al. |
| 2010/0109876 A1 | 5/2010 | Schmid-Schonbein |
| 2010/0111383 A1 | 5/2010 | Boushey et al. |
| 2010/0114125 A1 | 5/2010 | Albrecht et al. |
| 2010/0114150 A1 | 5/2010 | Magal |
| 2010/0125176 A1 | 5/2010 | Hyde et al. |
| 2010/0125177 A1 | 5/2010 | Hyde et al. |
| 2010/0125178 A1 | 5/2010 | Hyde et al. |
| 2010/0125179 A1 | 5/2010 | Hyde et al. |
| 2010/0125180 A1 | 5/2010 | Hyde et al. |
| 2010/0125181 A1 | 5/2010 | Hyde et al. |
| 2010/0125417 A1 | 5/2010 | Hyde et al. |
| 2010/0125418 A1 | 5/2010 | Hyde et al. |
| 2010/0125419 A1 | 5/2010 | Hyde et al. |
| 2010/0125420 A1 | 5/2010 | Hyde et al. |
| 2010/0130998 A1 | 5/2010 | Alverdy |
| 2010/0135945 A1 | 6/2010 | Murdock et al. |
| 2010/0137897 A1 | 6/2010 | Brister et al. |
| 2010/0145301 A1* | 6/2010 | Magal ............... A61F 5/0003 604/503 |
| 2010/0145378 A1 | 6/2010 | Gertner |
| 2010/0152532 A1 | 6/2010 | Marcotte |
| 2010/0152764 A1 | 6/2010 | Merkle |
| 2010/0160745 A1 | 6/2010 | Hills et al. |
| 2010/0168815 A1 | 7/2010 | Knudson et al. |
| 2010/0173269 A1 | 7/2010 | Puri et al. |
| 2010/0183700 A1 | 7/2010 | Stojanovic-Susulic |
| 2010/0191155 A1 | 7/2010 | Kim et al. |
| 2010/0194573 A1 | 8/2010 | Hoover et al. |
| 2010/0204669 A1 | 8/2010 | Knight |
| 2010/0204723 A1 | 8/2010 | Gertner |
| 2010/0205209 A1 | 8/2010 | Jokinen |
| 2010/0209897 A1 | 8/2010 | Utley et al. |
| 2010/0215584 A1 | 8/2010 | Passe |
| 2010/0217194 A1 | 8/2010 | Pang |

(56) References Cited

U.S. PATENT DOCUMENTS

| | | |
|---|---|---|
| 2010/0228080 A1 | 9/2010 | Tavori et al. |
| 2010/0228160 A1 | 9/2010 | Schweizer |
| 2010/0234682 A1 | 9/2010 | Gertner |
| 2010/0234917 A1 | 9/2010 | Imran |
| 2010/0240962 A1 | 9/2010 | Contant |
| 2010/0241090 A1 | 9/2010 | Klein et al. |
| 2010/0256775 A1 | 10/2010 | Belhe et al. |
| 2010/0267643 A1 | 10/2010 | Baron et al. |
| 2010/0268306 A1 | 10/2010 | Maniak et al. |
| 2010/0274274 A1 | 10/2010 | Roslin et al. |
| 2010/0286660 A1 | 11/2010 | Gross |
| 2010/0286745 A1 | 11/2010 | Imran |
| 2010/0291515 A1 | 11/2010 | Pinnisi et al. |
| 2010/0298631 A1 | 11/2010 | Stack et al. |
| 2010/0298632 A1 | 11/2010 | Levine et al. |
| 2010/0298812 A1 | 11/2010 | Wolkenstorfer |
| 2010/0305468 A1 | 12/2010 | Policker et al. |
| 2010/0305656 A1 | 12/2010 | Imran et al. |
| 2010/0312049 A1 | 12/2010 | Forsell |
| 2010/0312050 A1 | 12/2010 | Forsell |
| 2010/0312147 A1 | 12/2010 | Gertner |
| 2010/0316768 A1 | 12/2010 | Stillman |
| 2010/0324358 A1 | 12/2010 | Birk et al. |
| 2010/0324361 A1 | 12/2010 | Forsell |
| 2010/0324432 A1 | 12/2010 | Bjorling et al. |
| 2010/0331616 A1 | 12/2010 | Forsell |
| 2010/0331617 A1 | 12/2010 | Forsell |
| 2010/0332000 A1 | 12/2010 | Forsell |
| 2010/0332571 A1 | 12/2010 | Healey et al. |
| 2011/0004266 A1 | 1/2011 | Sharma |
| 2011/0009690 A1 | 1/2011 | Belhe et al. |
| 2011/0009887 A1 | 1/2011 | Harris et al. |
| 2011/0009895 A1 | 1/2011 | Gertner |
| 2011/0009896 A1 | 1/2011 | Forsell |
| 2011/0009980 A1 | 1/2011 | Levy et al. |
| 2011/0015665 A1 | 1/2011 | Marco et al. |
| 2011/0015666 A1 | 1/2011 | Marco et al. |
| 2011/0021968 A1 | 1/2011 | Knudson et al. |
| 2011/0022072 A1 | 1/2011 | Marco et al. |
| 2011/0034760 A1 | 2/2011 | Brynelsen et al. |
| 2011/0034967 A1 | 2/2011 | Chen et al. |
| 2011/0034968 A1 | 2/2011 | Knudson et al. |
| 2011/0040232 A1 | 2/2011 | Magal |
| 2011/0040318 A1 | 2/2011 | Marco et al. |
| 2011/0060308 A1 | 3/2011 | Stokes et al. |
| 2011/0060358 A1 | 3/2011 | Stokes et al. |
| 2011/0065660 A1 | 3/2011 | Baron et al. |
| 2011/0066207 A1 | 3/2011 | Imran |
| 2011/0082407 A1 | 4/2011 | Aronne |
| 2011/0082442 A1 | 4/2011 | Solovay et al. |
| 2011/0087076 A1 | 4/2011 | Brynelsen et al. |
| 2011/0087137 A1 | 4/2011 | Hanoun |
| 2011/0087146 A1 | 4/2011 | Ryan et al. |
| 2011/0092998 A1 | 4/2011 | Hirszowicz et al. |
| 2011/0098725 A1 | 4/2011 | Cox et al. |
| 2011/0104336 A1 | 5/2011 | Stillman |
| 2011/0106129 A1 | 5/2011 | Gertner |
| 2011/0106273 A1 | 5/2011 | Belhe et al. |
| 2011/0125063 A1 | 5/2011 | Shalon et al. |
| 2011/0125211 A1 | 5/2011 | Griffin et al. |
| 2011/0130626 A1 | 6/2011 | Hassler et al. |
| 2011/0136909 A1 | 6/2011 | Imada et al. |
| 2011/0152899 A1 | 6/2011 | Deem et al. |
| 2011/0160129 A1 | 6/2011 | Imran |
| 2011/0160699 A1 | 6/2011 | Imran |
| 2011/0166065 A1 | 7/2011 | Bhanot et al. |
| 2011/0166582 A1 | 7/2011 | Syed et al. |
| 2011/0172693 A1 | 7/2011 | Forsell |
| 2011/0178480 A1 | 7/2011 | Solovay et al. |
| 2011/0178544 A1 | 7/2011 | Sosnowski et al. |
| 2011/0182477 A1 | 7/2011 | Tamrakar et al. |
| 2011/0184229 A1 | 7/2011 | Raven et al. |
| 2011/0184247 A1 | 7/2011 | Contant et al. |
| 2011/0190719 A1 | 8/2011 | Kamen et al. |
| 2011/0196411 A1 | 8/2011 | Forsell |
| 2011/0196504 A1 | 8/2011 | Imran |
| 2011/0201874 A1 | 8/2011 | Birk et al. |
| 2011/0207994 A1 | 8/2011 | Burrell et al. |
| 2011/0207995 A1 | 8/2011 | Snow et al. |
| 2011/0208209 A1 | 8/2011 | Ewers et al. |
| 2011/0208216 A1 | 8/2011 | Fobi et al. |
| 2011/0213385 A1 | 9/2011 | Ewers et al. |
| 2011/0213448 A1 | 9/2011 | Kim |
| 2011/0213469 A1 | 9/2011 | Chin et al. |
| 2011/0218407 A1 | 9/2011 | Haberman et al. |
| 2011/0224155 A1 | 9/2011 | Tachdjian et al. |
| 2011/0224714 A1 | 9/2011 | Gertner |
| 2011/0230502 A1 | 9/2011 | Tachdjian et al. |
| 2011/0230938 A1 | 9/2011 | Simon et al. |
| 2011/0238035 A1 | 9/2011 | Jaax et al. |
| 2011/0244514 A1 | 10/2011 | Zuker et al. |
| 2011/0245598 A1 | 10/2011 | Gertner |
| 2011/0245752 A1 | 10/2011 | Levine et al. |
| 2011/0251495 A1 | 10/2011 | Province et al. |
| 2011/0269711 A1 | 11/2011 | Adden et al. |
| 2011/0270025 A1 | 11/2011 | Fridez et al. |
| 2011/0270030 A1 | 11/2011 | Birk et al. |
| 2011/0270344 A1 | 11/2011 | Knudson et al. |
| 2011/0270410 A1 | 11/2011 | Stack et al. |
| 2011/0275887 A1 | 11/2011 | Birk |
| 2011/0276112 A1 | 11/2011 | Simon et al. |
| 2011/0276312 A1 | 11/2011 | Shalon et al. |
| 2011/0282411 A1 | 11/2011 | Knudson et al. |
| 2011/0295055 A1 | 12/2011 | Albrecht et al. |
| 2011/0295056 A1 | 12/2011 | Aldridge et al. |
| 2011/0295057 A1 | 12/2011 | Aldridge et al. |
| 2011/0295335 A1 | 12/2011 | Sharma et al. |
| 2011/0295336 A1 | 12/2011 | Sharma et al. |
| 2011/0306824 A1 | 12/2011 | Perron et al. |
| 2011/0307023 A1 | 12/2011 | Tweden et al. |
| 2011/0307027 A1 | 12/2011 | Sharma et al. |
| 2011/0307028 A1 | 12/2011 | Sharma et al. |
| 2011/0307075 A1 | 12/2011 | Sharma |
| 2011/0313240 A1 | 12/2011 | Phillips et al. |
| 2011/0314849 A1 | 12/2011 | Park et al. |
| 2011/0318717 A1 | 12/2011 | Adamowicz |
| 2011/0319924 A1 | 12/2011 | Cole et al. |
| 2011/0319969 A1 | 12/2011 | Dobak |
| 2012/0004590 A1 | 1/2012 | Stack et al. |
| 2012/0004676 A1 | 1/2012 | Vargas |
| 2012/0009551 A1 | 1/2012 | Pinnisi |
| 2012/0010459 A1 | 1/2012 | Lau et al. |
| 2012/0010590 A1 | 1/2012 | Imran |
| 2012/0015021 A1 | 1/2012 | Mizrahi et al. |
| 2012/0015432 A1 | 1/2012 | Adler |
| 2012/0016287 A1 | 1/2012 | Stack et al. |
| 2012/0016392 A1 | 1/2012 | Silverman et al. |
| 2012/0021388 A1 | 1/2012 | Arbuckle et al. |
| 2012/0022319 A1 | 1/2012 | Muller |
| 2012/0022322 A1 | 1/2012 | Pasricha |
| 2012/0022430 A1 | 1/2012 | Stack et al. |
| 2012/0029550 A1 | 2/2012 | Forsell |
| 2012/0029591 A1 | 2/2012 | Simon et al. |
| 2012/0029601 A1 | 2/2012 | Simon et al. |
| 2012/0031805 A1 | 2/2012 | Stolarczyk |
| 2012/0036875 A1 | 2/2012 | Yun et al. |
| 2012/0040893 A1 | 2/2012 | Cowley et al. |
| 2012/0041463 A1 | 2/2012 | Forsell |
| 2012/0041465 A1 | 2/2012 | Shalon |
| 2012/0041509 A1 | 2/2012 | Knudson et al. |
| 2012/0046674 A1 | 2/2012 | Augarten et al. |
| 2012/0053426 A1 | 3/2012 | Webster et al. |
| 2012/0053504 A1 | 3/2012 | Kagan et al. |
| 2012/0053613 A1 | 3/2012 | Weitzner et al. |
| 2012/0053653 A1 | 3/2012 | Hiernaux et al. |
| 2012/0053660 A1 | 3/2012 | Dobak |
| 2012/0055718 A1 | 3/2012 | Chen |
| 2012/0058217 A1 | 3/2012 | Patty |
| 2012/0059216 A1 | 3/2012 | Perron |
| 2012/0065571 A1 | 3/2012 | Thompson et al. |
| 2012/0065706 A1 | 3/2012 | Vallapureddy et al. |
| 2012/0067937 A1 | 3/2012 | Menzel |
| 2012/0071812 A1 | 3/2012 | Mitelberg et al. |
| 2012/0071900 A1 | 3/2012 | Vahid et al. |

(56) References Cited

U.S. PATENT DOCUMENTS

| | | |
|---|---|---|
| 2012/0071947 A1 | 3/2012 | Gupta et al. |
| 2012/0072233 A1 | 3/2012 | Hanlon et al. |
| 2012/0077154 A1 | 3/2012 | Highet et al. |
| 2012/0078071 A1 | 3/2012 | Bohm et al. |
| 2012/0083650 A1 | 4/2012 | Raven |
| 2012/0083669 A1 | 4/2012 | Abujbara |
| 2012/0083705 A1 | 4/2012 | Yuen et al. |
| 2012/0083714 A1 | 4/2012 | Yuen et al. |
| 2012/0083715 A1 | 4/2012 | Yuen et al. |
| 2012/0083716 A1 | 4/2012 | Yuen et al. |
| 2012/0083855 A1 | 4/2012 | Gross et al. |
| 2012/0084053 A1 | 4/2012 | Yuen et al. |
| 2012/0084054 A1 | 4/2012 | Yuen et al. |
| 2012/0088962 A1 | 4/2012 | Franklin et al. |
| 2012/0089168 A1 | 4/2012 | Baker et al. |
| 2012/0089170 A1 | 4/2012 | Dominguez |
| 2012/0089172 A1 | 4/2012 | Babkes et al. |
| 2012/0094942 A1 | 4/2012 | Baron et al. |
| 2012/0095288 A1 | 4/2012 | Snow et al. |
| 2012/0095384 A1 | 4/2012 | Babkes et al. |
| 2012/0095492 A1 | 4/2012 | Babkes et al. |
| 2012/0095494 A1 | 4/2012 | Dominguez et al. |
| 2012/0095495 A1 | 4/2012 | Babkes et al. |
| 2012/0095496 A1 | 4/2012 | Dominguez et al. |
| 2012/0095497 A1 | 4/2012 | Babkes et al. |
| 2012/0095499 A1 | 4/2012 | Babkes et al. |
| 2012/0096405 A1 | 4/2012 | Seo |
| 2012/0101594 A1 | 4/2012 | Fogel |
| 2012/0101874 A1 | 4/2012 | Ben-Haim et al. |
| 2012/0108921 A1 | 5/2012 | Raven et al. |
| 2012/0109051 A1 | 5/2012 | Harrell |
| 2012/0115111 A1 | 5/2012 | Lepine |
| 2012/0115778 A1 | 5/2012 | Karsenty et al. |
| 2012/0116182 A1 | 5/2012 | Wong et al. |
| 2012/0116285 A1 | 5/2012 | Duggirala |
| 2012/0116286 A1 | 5/2012 | Williams et al. |
| 2012/0116536 A1 | 5/2012 | Imran |
| 2012/0123465 A1 | 5/2012 | Nihalani |
| 2012/0126983 A1 | 5/2012 | Breibart |
| 2012/0130273 A1 | 5/2012 | Hassler et al. |
| 2012/0143021 A1 * | 6/2012 | Nagar ............... A61B 5/14532 600/301 |
| 2012/0143279 A1 | 6/2012 | Ekchian et al. |
| 2012/0144912 A1 | 6/2012 | Kates et al. |
| 2012/0149996 A1 | 6/2012 | Stivoric et al. |
| 2012/0150316 A1 | 6/2012 | Carvalho |
| 2012/0157409 A1 | 6/2012 | Cherkassky |
| 2012/0160893 A1 | 6/2012 | Harris et al. |
| 2012/0165792 A1 | 6/2012 | Ortiz et al. |
| 2012/0165793 A1 | 6/2012 | Ortiz et al. |
| 2012/0165794 A1 | 6/2012 | Ortiz et al. |
| 2012/0165796 A1 | 6/2012 | Ortiz et al. |
| 2012/0165843 A1 | 6/2012 | Gannoe et al. |
| 2012/0165845 A1 | 6/2012 | Harris et al. |
| 2012/0165855 A1 | 6/2012 | Shalon et al. |
| 2012/0170801 A1 | 7/2012 | De Oliveira et al. |
| 2012/0172782 A1 | 7/2012 | Thompson |
| 2012/0177730 A1 | 7/2012 | Baron et al. |
| 2012/0179665 A1 | 7/2012 | Baarman et al. |
| 2012/0184893 A1 | 7/2012 | Thompson et al. |
| 2012/0190919 A1 | 7/2012 | Phillips et al. |
| 2012/0191123 A1 | 7/2012 | Brister et al. |
| 2012/0191124 A1 | 7/2012 | Brister et al. |
| 2012/0191125 A1 | 7/2012 | Babkes et al. |
| 2012/0191126 A1 | 7/2012 | Pecor et al. |
| 2012/0195954 A1 | 8/2012 | Maynard |
| 2012/0197069 A1 | 8/2012 | Lau et al. |
| 2012/0201725 A1 | 8/2012 | Imran |
| 2012/0203061 A1 | 8/2012 | Birk |
| 2012/0203081 A1 | 8/2012 | Leboeuf et al. |
| 2012/0208748 A1 | 8/2012 | Chen et al. |
| 2012/0209354 A1 | 8/2012 | Raykhman |
| 2012/0209400 A1 | 8/2012 | Schurr |
| 2012/0214140 A1 | 8/2012 | Brynelsen et al. |
| 2012/0215061 A1 | 8/2012 | Fridez et al. |
| 2012/0215062 A1 | 8/2012 | Coe |
| 2012/0215152 A1 | 8/2012 | Levine et al. |
| 2012/0215249 A1 | 8/2012 | Brazzini et al. |
| 2012/0221037 A1 | 8/2012 | Birk et al. |
| 2012/0221495 A1 | 8/2012 | Landers |
| 2012/0226471 A1 | 9/2012 | Yuen et al. |
| 2012/0226472 A1 | 9/2012 | Yuen et al. |
| 2012/0232361 A1 | 9/2012 | Birk |
| 2012/0232459 A1 | 9/2012 | Dann et al. |
| 2012/0232460 A1 | 9/2012 | Raven et al. |
| 2012/0232576 A1 | 9/2012 | Brister et al. |
| 2012/0232577 A1 | 9/2012 | Birk et al. |
| 2012/0245553 A1 | 9/2012 | Raven et al. |
| 2012/0253259 A1 | 10/2012 | Belhe et al. |
| 2012/0253260 A1 | 10/2012 | Belhe et al. |
| 2012/0253378 A1 | 10/2012 | Makower et al. |
| 2012/0259389 A1 | 10/2012 | Starkebaum et al. |
| 2012/0259427 A1 | 10/2012 | Graham et al. |
| 2012/0265030 A1 | 10/2012 | Li |
| 2012/0265224 A1 | 10/2012 | Coleman et al. |
| 2012/0265234 A1 | 10/2012 | Brister et al. |
| 2012/0271217 A1 | 10/2012 | Stack et al. |
| 2012/0277619 A1 | 11/2012 | Starkebaum et al. |
| 2012/0277661 A1 | 11/2012 | Bernard et al. |
| 2012/0277814 A1 | 11/2012 | Schuler |
| 2012/0277837 A1 | 11/2012 | Schuler |
| 2012/0283766 A1 | 11/2012 | Makower et al. |
| 2012/0289992 A1 | 11/2012 | Quijano et al. |
| 2012/0295233 A1 | 11/2012 | Cooperman |
| 2012/0296157 A1 | 11/2012 | Tozzi et al. |
| 2012/0296348 A1 | 11/2012 | Saadat et al. |
| 2012/0296354 A1 | 11/2012 | Hsu et al. |
| 2012/0299723 A1 | 11/2012 | Hafezi et al. |
| 2012/0302936 A1 | 11/2012 | Belhe et al. |
| 2012/0310295 A1 | 12/2012 | Libbus et al. |
| 2012/0313776 A1 | 12/2012 | Utter |
| 2012/0316387 A1 | 12/2012 | Volker |
| 2012/0316451 A1 | 12/2012 | Province et al. |
| 2012/0316459 A1 | 12/2012 | Abreu |
| 2012/0316932 A1 | 12/2012 | Rahman et al. |
| 2012/0317167 A1 | 12/2012 | Rahman et al. |
| 2012/0323099 A1 | 12/2012 | Mothilal et al. |
| 2012/0326873 A1 | 12/2012 | Utter |
| 2013/0002435 A1 | 1/2013 | Utter |
| 2013/0004923 A1 | 1/2013 | Utter |
| 2013/0006063 A1 | 1/2013 | Wang |
| 2013/0006125 A1 | 1/2013 | Kroll et al. |
| 2013/0006807 A1 | 1/2013 | Bai et al. |
| 2013/0027060 A1 | 1/2013 | Tralshawala et al. |
| 2013/0029807 A1 | 1/2013 | Amsel |

FOREIGN PATENT DOCUMENTS

| | | |
|---|---|---|
| EP | 2072048 | 6/2009 |
| WO | WO 02082968 | 10/2002 |
| WO | WO 02085428 | 10/2002 |
| WO | WO 03004034 | 1/2003 |

* cited by examiner

DEVICE FOR SELECTIVELY REDUCING ABSORPTION OF UNHEALTHY FOOD

CROSS-REFERENCE TO RELATED APPLICATIONS

This patent application claims the priority benefit of U.S. Provisional Patent Application No. 61/729,494 entitled "Device for Selectively Reducing Absorption of Unhealthy Food" filed on Nov. 23, 2012 by Robert A. Connor of Medibotics, LLC.

FEDERALLY SPONSORED RESEARCH

Not applicable

SEQUENCE LISTING OR PROGRAM

Not applicable

BACKGROUND

Field of Invention

This invention relates to energy balance, weight loss, and proper nutrition.

Introduction to Energy Balance and Proper Nutrition

The United States population has some of the highest prevalence rates of obese and overweight people in the world. Further, these rates have increased dramatically during recent decades. In the late 1990's, around one in five Americans was obese. Today, that figure has increased to around one in three. It is estimated that around one in five American children is now obese. The prevalence of Americans who are generally overweight is estimated to be as high as two out of three.

This increase in the prevalence of Americans who are overweight or obese has become one of the most common causes of health problems in the United States. Potential adverse health effects from obesity include: cancer (especially endometrial, breast, prostate, and colon cancers); cardiovascular disease (including heart attack and arterial sclerosis); diabetes (type 2); digestive diseases; gallbladder disease; hypertension; kidney failure; obstructive sleep apnea; orthopedic complications; osteoarthritis; respiratory problems; stroke; metabolic syndrome (including hypertension, abnormal lipid levels, and high blood sugar); impairment of quality of life in general including stigma and discrimination; and even death.

There are estimated to be over a quarter-million obesity-related deaths each year in the United States. The tangible costs to American society of obesity have been estimated at over $100 billion dollars per year. This does not include the intangible costs of human pain and suffering. Despite the considerable effort that has been focused on developing new approaches for preventing and treating obesity, the problem is growing. There remains a serious unmet need for new ways to help people to moderate their consumption of unhealthy food, better manage their energy balance, and lose weight in a healthy and sustainable manner.

Obesity is a complex disorder with multiple interacting causal factors including genetic factors, environmental factors, and behavioral factors. A person's behavioral factors include the person's caloric intake (the types and quantities of food which the person consumes) and caloric expenditure (the calories that the person burns in regular activities and exercise). Energy balance is the net difference between caloric intake and caloric expenditure. Other factors being equal, energy balance surplus (caloric intake greater than caloric expenditure) causes weight gain and energy balance deficit (caloric intake less than caloric expenditure) causes weight loss.

Since many factors contribute to obesity, good approaches to weight management are comprehensive in nature. Proper nutrition and management of caloric intake are key parts of a comprehensive approach to weight management. Consumption of "junk food" that is high in simple sugars and saturated fats has increased dramatically during the past couple decades, particularly in the United States. This has contributed significantly to the obesity epidemic. For many people, relying on willpower and dieting is not sufficient to moderate their consumption of unhealthy "junk food." The results are dire consequences for their health and well-being.

The invention that is disclosed herein directly addresses this problem by helping a person to selectively reduce absorption of nutrients from unhealthy food. The invention that is disclosed herein is an innovative technology that can be a key part of a comprehensive system that helps a person to reduce their consumption of unhealthy food, to better manage their energy balance, and to lose weight in a healthy and sustainable manner. In the following sections, we categorize and review the prior art, provide a summary of this invention and its advantages over the prior art, and then provide some detailed examples of how this invention can be embodied to help a person to improve their nutrition and to manage their weight.

Categorization and Review of the Prior Art

It can be challenging to classify prior art into discrete categories. This is the certainly the case in the field of energy balance, weight management, and proper nutrition. There are numerous examples of potentially-relevant prior art. However, classification of the prior art into categories, even if imperfect, is an invaluable tool for reviewing the prior art, identifying its limitations, and setting the stage for discussion of the advantages of the invention that is disclosed in subsequent sections. Towards this end, I now identify 50 general categories of prior art and list examples of prior art which appear to be best classified into each category. This categorization and discussion of the prior art helps to identify limitations of the prior art which are corrected by the invention disclosed herein in subsequent sections. The categories of prior art that are most relevant to this invention are marked with an asterisk "*".

The 50 categories of prior art that I will now discuss are as follows: (1) little or no automated measurement of food consumption, (2) consumed manufactured compound or specifically-isolated natural substance, (3) substance sprinkled on food, (4) manually-ingested spray or pulse, (5) substance-emitting lipstick or toothpaste, (6) substance-emitting adhesive patch in the mouth, (7) dissolving film in mouth, (8) tablet or gum in mouth, (9) intraoral drug delivery, (10*) motion guided or directed pill, (11*) general implanted drug pump, (12) food purchasing monitoring or modification, (13) food scale, (14) portion size control, (15) mouth size or function modification, (16*) chewing and swallowing monitoring, (17) hand and/or arm motion monitoring and modification (wrist), (18) hand and/or arm motion monitoring and modification (utensil), (19) utensil with sensor other than motion sensor, (20) other modification of eating speed, (21) photo identification of food (bar code or other packaging-based code), (22) photo identification of food (manual picture taking and identification), (23) photo identification of food (manual picture taking and automated identification), (24) photo identification of food (automated picture taking and identification), (25*) gastric band, (26*) gastric band with sensor, (27*) gastrointestinal (GI) bypass and tissue plication, (28*) pumping food out of the stomach through an intra-abdominal pathway, (29*) gastric tube, (30*) enzyme flow modification, (31) gastrointestinal (GI) volume or pressure or flow modification, (32*) gastrointestinal (GI) volume or pressure or flow modification (with drug), (33) gastrointestinal (GI) sleeve or liner, (34*) gastrointestinal (GI) sleeve or liner (with drug), (35*) electrical stimulation (general), (36*) electrical stimulation (with glucose sensor), (37*) electrical stimulation (with general sensor), (38) electrical stimulation (with taste modification), (39*) electrical stimulation (with drug), (40*) electrical stimulation (with drug and sensor), (41) salivation stimulation, (42*) general sensor (glucose), (43*) general sensor (electromagnetic), (44*) general sensor (chemical), (45*) general sensor (microwave), (46*) sensor (intraoral), (47*) sensor (general), (48) blood analysis, (49) general energy balance feedback, and (50) miscellaneous energy balance related.

1. Little (or No) Automatic Measurement of Food Consumption

This category includes prior art with little (or no) automatic measurement of food consumption. The vast majority of art in this category requires a person to take specific action (apart from the actual act of eating) in order to record food consumption. For many years, people did this using pencil and paper. Now they can do it with computer assistance (such as an application on a mobile electronic device), but even the computer-assisted methods in this category still rely on specific human action to record food consumption.

Interfaces for the human action required to record food consumption can include: touch screen; voice and/or speech recognition; keyboard, keypad, or buttons; and mouse, trackball, or touchpad. Gesture recognition may become a more popular interface in future years. Devices comprising art in this category can be worn on a person (e.g. a wrist-mounted band or necklace), carried by a person (e.g. a mobile phone or electronic tablet), or stationary (e.g. a desktop computer). Some wrist-mounted bands and food-serving utensils that do not explicitly track caloric intake are nonetheless included in this category because of their innovative measurement of caloric output and their general relevance to energy balance.

Recent art in this category makes manual recording of food consumption easier with computer-assisted features such as menu-driven user interfaces and voice recognition. These can definitely make it easier for someone to associate specific nutrients or calorie amounts with specific common foods through the use of a food-nutrient database. However, even recent art in this category still requires specific action by a person associated with each eating event apart from the actual act of eating. They offer little (or no) automatic monitoring of food consumption. If a person does not record each food consumption event, then such a device is unaware that food has been consumed. Long-term compliance with manual food logs is notoriously low. People tend to underestimate calories consumed (especially for unstructured snacking). The accuracy of caloric intake monitoring with art in this category still depends largely, or entirely, on the voluntary compliance of the person whose actions are needed to manually record food consumption. Also, even if food consumption is properly recorded, the success of such art in actually modifying food consumption further depends on the effectiveness of its behavioral modification methods.

Examples of prior art that appear to be best classified in this category include U.S. patents: U.S. Pat. No. 4,100,401 (Jul. 11, 1978 Tutt et al.) "Calorie Calculator-Chronometer", U.S. Pat. No. 4,212,079 (Jul. 8, 1980 Segar et al.) "Electronic Calorie Counter", U.S. Pat. No. 4,218,611 (Aug. 19, 1980 Cannon) "Method and Apparatus for Controlling Eating Behavior", U.S. Pat. No. 4,221,959 (Sep. 9, 1980 Sessler) "Checking Device for Checking the Food Intake", U.S. Pat. No. 4,310,316 (Jan. 12, 1982 Thomann) "Diet Control Apparatus", U.S. Pat. No. 4,321,674 (Mar. 23, 1982 Krames et al.) "Nutritional Value Accumulating and Display Device", U.S. Pat. No. 4,650,218 (Mar. 17, 1987 Hawke) "Method and Apparatus for Controlling Caloric Intake", U.S. Pat. No. 4,686,624 (Aug. 11, 1987 Blum et al.) "Portable Apparatus for Acquiring and Processing Data Relative to the Dietetics and/or the Health of a Person", U.S. Pat. No. 4,796,182 (Jan. 3, 1989 Duboff) "Diet Monitor and Display Device", U.S. Pat. No. 5,173,588 (Dec. 22, 1992 Harrah) "Food Consumption Monitor", U.S. Pat. No. 5,478,989 (Dec. 26, 1995 Shepley) "Nutritional Information System for Shoppers", U.S. Pat. No. 5,542,420 (Aug. 6, 1996 Goldman et al.) "Personalized Method and System for Storage, Communication, Analysis, and Processing of Health-Related Data", U.S. Pat. No. 5,673,691 (Oct. 7, 1997 Abrams et al.) "Apparatus to Control Diet and Weight Using Human Behavior Modification Techniques", U.S. Pat. No. 5,691,927 (Nov. 25, 1997 Gump) "Nutritional Aid and Method", U.S. Pat. No. 5,704,350 (Jan. 6, 1998 Williams) "Nutritional Microcomputer and Method", U.S. Pat. No. 5,729,479 (Mar. 17, 1998 Golan) "Multifunctional Diet Calculator", U.S. Pat. No. 5,836,312 (Nov. 17, 1998 Moore) "Computer-Assisted System and Method for Adjudging the Effect of Consumable Intakes on Physiological Parameters", U.S. Pat. No. 5,839,901 (Nov. 24, 1998 Karkanen) "Integrated Weight Loss Control Method", U.S. Pat. No. 5,841,115 (Nov. 24, 1998 Shepley) "Nutritional Information System for Shoppers", U.S. Pat. No. 5,890,128 (Mar. 30, 1999 Diaz et al.) "Personalized Hand Held Calorie Computer (ECC)", U.S. Pat. No. 5,989,188 (Nov. 23, 1999 Birkhoelzer) "Method and Apparatus for Determining the Energy Balance of a Living Subject on the Basis of Energy Used and Nutrition Intake", U.S. Pat. No. 6,024,281 (Feb. 15, 2000 Shepley) "Nutritional Information System for Shoppers", and U.S. Pat. No. 6,032,676 (Mar. 7, 2000 Moore) "Method for Correlating Consumable Intakes with Physiological Parameters".

Examples of prior art that appear to be best classified in this category also include U.S. patents: U.S. Pat. No. 6,040,531 (Mar. 21, 2000 Miller-Kovach) "Process For Controlling Body Weight", U.S. Pat. No. 6,083,006 (Jul. 4, 2000 Coffman) "Personalized Nutrition Planning", U.S. Pat. No. 6,095,949 (Aug. 1, 2000 Arai) "Health Management Device", U.S. Pat. No. 6,336,136 (Jan. 1, 2002 Harris) "Internet Weight Reduction System", U.S. Pat. No. 6,341,295 (Jan. 22, 2002 Stotler) "Virtual Reality Integrated Caloric Tabulator", U.S. Pat. No. 6,478,736 (Nov. 12, 2002 Mault) "Integrated Calorie Management System", U.S. Pat. No. 6,506,152 (Jan. 14, 2003 Lackey et al.) "Caloric Energy Balance Monitor", U.S. Pat. No. 6,553,386 (Apr. 22, 2003 Alabaster) "System and Method for Computerized Visual Diet Behavior Analysis and Training", U.S. Pat. No. 6,571,200 (May 27, 2003 Mault) "Monitoring Caloric Expenditure Resulting from Body Activity", U.S. Pat. No. 6,595,929 (Jul. 22, 2003 Stivoric et al.) "System for Monitoring Health Wellness and Fitness Having a Method and Apparatus for Improved Measurement of Heat Flow", U.S. Pat. No. 6,605,038 (Aug. 12, 2003 Teller et al.) "System for Monitoring Health, Wellness and Fitness", U.S. Pat. No. 6,635,015 (Oct. 21, 2003 Sagel) "Body Weight Management System", U.S. Pat. No. 6,675,041 (Jan. 6, 2004 Dickinson) "Electronic Apparatus and Method for Monitoring Net Calorie Intake", U.S. Pat. No. 6,694,182 (Feb. 17, 2004 Yamazaki et al.) "Wearable Calorie Calculator", U.S. Pat. No. 6,745,214 (Jun. 1, 2004 Inoue et al.) "Calorie Control Apparatus with Voice Recognition", U.S. Pat. No. 6,856,938 (Feb. 15, 2005 Kurtz) "Weight Monitoring Computer", U.S. Pat. No. 6,878,885 (Apr. 12, 2005 Miller-Kovach) "Process for Controlling Body Weight", U.S. Pat. No. 6,917,897 (Jul. 12, 2005 Mork) "Food and Exercise Calculator", U.S. Pat. No. 7,020,508 (Mar. 28, 2006 Stivoric et al.) "Apparatus for Detecting Human Physiological and Contextual Information", U.S. Pat. No. 7,261,690 (Aug. 28, 2007 Teller et al.) "Apparatus for Monitoring Health, Wellness and Fitness", U.S. Pat. No. 7,285,090 (Oct. 23, 2007 Stivoric et al.) "Apparatus for Detecting, Receiving, Deriving and Displaying Human Physiological and Contextual Information", and U.S. Pat. No. 7,361,141 (Apr. 22, 2008 Nissila et al.) "Method and Device for Weight Management of Humans".

Examples of prior art that appear to be best classified in this category also include U.S. patents: U.S. Pat. No. 7,454,002 (Nov. 18, 2008 Gardner et al.) "Integrating Personal Data Capturing Functionality into a Portable Computing Device and a Wireless Communication Device", U.S. Pat. No. 7,500,937 (Mar. 10, 2009 Hercules) "Diet Compliance System", U.S. Pat. No. 7,689,437 (Mar. 30, 2010 Teller et al.) "System for Monitoring Health, Wellness and Fitness", U.S. Pat. No. 7,857,730 (Dec. 28, 2010 Dugan) "Methods and Apparatus for Monitoring and Encouraging Health and Fitness", U.S. Pat. No. 7,949,506 (May 24, 2011 Hill et al.) "Method for Determining and Compensating for a Weight Loss Energy Gap", U.S. Pat. No. 7,959,567 (Jun. 14, 2011 Stivoric et al.) "Device to Enable Quick Entry of Caloric Content", U.S. Pat. No. 8,073,707 (Dec. 6, 2011 Teller et al.) "System for Detecting Monitoring and Reporting an Individual's Physiological or Contextual Status", U.S. Pat. No. 8,075,451 (Dec. 13, 2011 Dugan) "Methods and Apparatus for Monitoring and Encouraging Health and Fitness", U.S. Pat. No. 8,087,937 (Jan. 3, 2012 Peplinski et al.) "System and Method for Monitoring Weight and Nutrition", U.S. Pat. No. 8,157,731 (Apr. 17, 2012 Teller et al.) "Method and Apparatus for Auto Journaling of Continuous or Discrete Body States Utilizing Physiological and/or Contextual Parameters", U.S. Pat. No. 8,180,592 (May 15, 2012 Yuen et al.) "Portable Monitoring Devices and Methods of Operating Same", U.S. Pat. No. 8,311,769 (Nov. 13, 2012 Yuen et al.) "Portable Monitoring Devices and Methods of Operating Same", and U.S. Pat. No. 8,311,770 (Nov. 13, 2012 Yuen et al.) "Portable Monitoring Devices and Methods of Operating Same".

Examples of prior art that appear to be best classified in this category also include U.S. patent applications: 20020133378 (Sep. 19, 2002 Mault et al.) "System and Method of Integrated Calorie Management", 20020156351 (Oct. 24, 2002 Sagel) "Body Weight Management System", 20030152607 (Aug. 14, 2003 Mault) "Caloric Management System and Method with Voice Recognition", 20030165799 (Sep. 4, 2003 Bisogno) "Computer Program, Method, and System for Monitoring Nutrition Content of Consumables and for Facilitating Menu Planning", 20030219513 (Nov. 27, 2003 Gordon) "Personal Nutrition Control Method", 20040034289 (Feb. 19, 2004 Teller et al.) "System for Monitoring Health, Wellness and Fitness", 20040133081 (Jul. 8, 2004 Teller et al.) "Method and Apparatus for Auto Journaling of Continuous or Discrete Body States Utilizing Physiological and/or Contextual Parameters", 20040133081 (Jul. 8, 2004 Teller et al.) "Method and Apparatus for Auto Journaling of Continuous or Discrete Body States Utilizing Physiological and/or Contextual Parameters", 20040152957 (Aug. 5, 2004 Stivoric et al.) "Apparatus for Detecting, Receiving, Deriving and Displaying Human Physiological and Contextual Information", 20050004436 (Jan. 6, 2005 Nissila et al.) "Method and Device for Weight Management of Humans", 20050008994 (Jan. 13, 2005 Bisogno) "Computer Program, Method, and System for Monitoring Nutrition Content of Consumables and for Facilitating Menu Planning", 20050113650 (May 26, 2005 Pacione et al.) "System for Monitoring and Managing Body Weight and Other Physiological Conditions Including Iterative and Personalized Planning . . . ", 20050247213 (Nov. 10, 2005 Slilaty) "Method of Identifying Particular Attributes of Food Products Consistent with Consumer Needs and/or Desires", 20050266385 (Dec. 1, 2005 Bisogno) "Computer Program, Method, and System for Monitoring Nutrition Content of Consumables and for Facilitating Menu Planning", 20060031102 (Feb. 9, 2006 Teller et al.) "System for Detecting Monitoring and Reporting an Individual's Physiological or Contextual Status", 20060036395 (Feb. 16, 2006 Shaya et al.) "Method and Apparatus for Measuring and Controlling Food Intake of an Individual", 20060074716 (Apr. 6, 2006 Tilles et al.) "System and Method for Providing Customized Interactive and Flexible Nutritional Counseling", and 20060122474 (Jun. 8, 2006 Teller et al.) "Apparatus for Monitoring Health Wellness and Fitness".

Examples of prior art that appear to be best classified in this category also include U.S. patent applications: 20060264730 (Nov. 23, 2006 Stivoric et al.) "Apparatus for Detecting Human Physiological and Contextual Information", 20070027366 (Feb. 1, 2007 Osburn) "Device and System for Entering and Monitoring Dietary Data", 20070089335 (Apr. 26, 2007 Smith et al.) "Nutrient Consumption/Expenditure Planning and Tracking Apparatus System and Method", 20070106129 (May 10, 2007 Srivathsa et al.) "Dietary Monitoring System for Comprehensive Patient Management", 20070179355 (Aug. 2, 2007 Rosen) "Mobile Self-Management Compliance and Notification Method, System and Computer Program Product", 20070208593 (Sep. 6, 2007 Hercules) "Diet Compliance System", 20080161654 (Jul. 3, 2008 Teller et al.) "Method and Apparatus for Auto Journaling of Body States and Providing Derived Physiological States Utilizing Physiological and/or Contextual Parameter", 20080161655 (Jul. 3, 2008 Teller et al.) ibid, 20080167536 (Jul. 10, 2008 Teller et al.) ibid, 20080167537 (Jul. 10, 2008 Teller et al.) ibid, 20080167538 (Jul. 10, 2008 Teller et al.) ibid, 20080167539 (Jul. 10, 2008 Teller et al.) ibid, 20080171920 (Jul. 17, 2008 Teller et al.) ibid, 20080171921 (Jul. 17, 2008 Teller et al.) ibid, 20080171922 (Jul. 17, 2008 Teller et al.) ibid, 20080275309 (Nov. 6, 2008 Stivoric et al.) "Input Output Device for Use with Body Monitor", 20090177068 (Jul. 9, 2009 Stivoric et al.) "Method and Apparatus for Providing Derived Glucose Information Utilizing Physiological and/or Contextual Parameters", 20090191514 (Jul. 30, 2009 Barnow) "Calorie Counter", 20100057564 (Mar. 4, 2010 Godsey et al.) "System and Method for Fitness Motivation", 20100062119 (Mar. 11, 2010 Miller-Kovach) "Processes and Systems for Achieving and Assisting in Improved Nutrition", 20100062402 (Mar. 11, 2010 Miller-Kovach) "Processes and Systems Using and Producing Food Healthfulness Data Based on Linear Combinations of Nutrients", 20100079291 (Apr. 1, 2010 Kroll et al.) "Personalized Activity Monitor and Weight Management System", 20100080875 (Apr. 1, 2010 Miller-Kovach) "Processes and Systems for Achieving and Assisting in Improved Nutrition Based on Food Energy Data and Relative Healthfulness Data", and 20100228160 (Sep. 9, 2010 Schweizer) "Apparatus for Activity Monitoring".

Examples of prior art that appear to be best classified in this category also include U.S. patent applications: 20110087137 (Apr. 14, 2011 Hanoun) "Mobile Fitness and Personal Caloric Management System", 20120031805 (Feb. 9, 2012 Stolarczyk) "Daily Meal Planning System", 20120072233 (Mar. 22, 2012 Hanlon et al.) "Medical Health Information System for Health Assessment, Weight Management and Meal Planning", 20120083669 (Apr. 5, 2012 Abujbara) "Personal Nutrition and Wellness Advisor", 20120083705 (Apr. 5, 2012 Yuen et al.) "Activity Monitoring Systems and Methods of Operating Same", 20120083714 (Apr. 5, 2012 Yuen et al.) "Activity Monitoring Systems and Methods of Operating Same", 20120083715 (Apr. 5, 2012 Yuen et al.) "Portable Monitoring Devices and Methods of Operating Same", 20120083716 (Apr. 5, 2012 Yuen et al.) "Portable Monitoring Devices and Methods of Operating Same", 20120084053 (Apr. 5, 2012 Yuen et al.) "Portable Monitoring Devices and Methods of Operating Same", 20120084054 (Apr. 5, 2012 Yuen et al.) "Portable Monitoring Devices and Methods of Operating Same", 20120096405 (Apr. 19, 2012 Seo) "Apparatus and Method for Diet Management", 20120126983 (May 24, 2012 Breibart) "Method and Associated Device for Personal Weight Control or Weight Loss", 20120221495 (Aug. 30, 2012 Landers) "Digital Weight Loss Aid", 20120226471 (Sep. 6, 2012 Yuen et al.) "Portable Monitoring Devices and Methods of Operating Same", 20120226472 (Sep. 6, 2012 Yuen et al.) "Portable Monitoring Devices and Methods of Operating Same", 20120295233 (Nov. 22, 2012 Cooperman) "Computerized System and Method for Monitoring Food Consumption", 20120316932 (Dec. 13, 2012 Rahman et al.) "Wellness Application for Data-Capable Band", 20120317167 (Dec. 13, 2012 Rahman et al.) "Wellness Application for Data-Capable Band", 20130002435 (Jan. 3, 2013 Utter) "Sleep Management Method and Apparatus for a Wellness Application Using Data from a Data-Capable Band", 20130006063 (Jan. 3, 2013 Wang) "Physiological Condition, Diet and Exercise Plan Recommendation and Management System", 20130006125 (Jan. 3, 2013 Kroll et al.) "Personalized Activity Monitor and Weight Management System", and 20130029807 (Jan. 31, 2013 Amsel) "Health Tracking Program".

2. Consumed Manufactured Compound or Specifically-Isolated Natural Substance

Prior art in this category includes manufactured compounds and specifically-isolated natural substances that are either added to food as an ingredient during food preparation or are consumed independently of food consumption in order to modify a person's food consumption. This category includes pharmaceuticals and specific food ingredients that are intended as appetite suppressants. For many years people have been seeking a "magic" pill that can address obesity with good results and tolerable side effects.

There are many examples of prior art in this category and we have only included those which appear to be most relevant. For the purposes of this categorization, we have created a separate subsequent category for substances which a person can sprinkle on food at the time of consumption. We have also included separate categories for inventions whose primary therapeutic modality is a device, but which also emit or elude a drug as a secondary mode of action. The success of art in this category for modifying food consumption depends on the substance's ability to actually modify the person's food consumption without intolerable side effects. Compliance and effectiveness can be problematic, especially if a drug's side effects are very unpleasant.

Examples of prior art that appear to be best classified in this category include U.S. patents: U.S. Pat. No. 4,159,347 (Jun. 26, 1979 Yoshida et al.) "Flavoring with Cyclic Acetals of 2-Methyl-2-Pentenal", U.S. Pat. No. 4,210,637 (Jul. 1, 1980 Wurtman et al.) "Composition and Method for Suppressing Appetite for Calories as Carbohydrates", U.S. Pat. No. 4,491,578 (Jan. 1, 1985 Peikin) "Method of Stimulating Satiety in Mammals", U.S. Pat. No. 4,497,798 (Feb. 5, 1985 Lambert) "Appetite Suppressant", U.S. Pat. No. 4,689,235 (Aug. 25, 1987 Barnes et al.) "Encapsulation Matrix Composition and Encapsulate Containing Same", U.S. Pat. No. 4,740,365 (Apr. 26, 1988 Yukimatsu et al.) "Sustained-Release Preparation Applicable to Mucous Membrane in Oral Cavity", U.S. Pat. No. 5,013,716 (May 7, 1991 Cherukuri et al.) "Unpleasant Taste Masking Compositions and Methods for Preparing Same", U.S. Pat. No. 5,290,808 (Mar. 1, 1994 Sofia) "Method to Control the Intake of Food", U.S. Pat. No. 5,405,641 (Apr. 11, 1995 Kurihara et al.) "Taste-Modification Composition and Method for Stabilizing Taste-Modifier", U.S. Pat. No. 5,472,685 (Dec. 5, 1995 Gaffar) "Antiplaque Oral Compositions", U.S. Pat. No. 5,605,698 (Feb. 25, 1997 Ueno) "Oral Composition", U.S. Pat. No. 5,858,967 (Jan. 12, 1999 Weigle et al.) "Appetite Suppression Factor and Related Methods", U.S. Pat. No. 6,123,980 (Sep. 26, 2000 Pearson et al.) "Preparing Granulated Sugar Blends and Products", U.S. Pat. No. 6,207,638 (Mar. 27, 2001 Portman) "Nutritional Intervention Composition for Enhancing and Extending Satiety", U.S. Pat. No. 6,224,873 (May 1, 2001 Jones) "Regulation of Appetite Body Weight and Athletic Function with Materials Derived from Citrus Varieties", U.S. Pat. No. 6,235,274 (May 22, 2001 Lou et al.) "Microparticles Which Controllably Release Olfactorily Active Substances Methods of Using Same and Processes for Preparing Same", U.S. Pat. No. 6,248,390 (Jun. 19, 2001 Stillman) "Fiber-Water: Water Containing Soluble Fiber", U.S. Pat. No. 6,319,523 (Nov. 20, 2001 Zhou) "Composition and Method for Inhibiting Oral Bacteria", U.S. Pat. No. 6,376,657 (Apr. 23, 2002 Van Heerden et al.) "Pharmaceutical Compositions Having Appetite Suppressant Activity", U.S. Pat. No. 6,413,545 (Jul. 2, 2002 Alviar et al.) "Diet Composition and Method of Weight Management", U.S. Pat. No. 6,610,277 (Aug. 26, 2003 Zuckerman) "Appetite Suppressant Toothpaste", and U.S. Pat. No. 6,861,405 (Mar. 1, 2005 Desir et al.) "Compositions and Methods Relating to Glucose Metabolism, Weight Control, and Food Intake".

Examples of prior art that appear to be best classified in this category also include U.S. patents: U.S. Pat. No. 6,942,848 (Sep. 13, 2005 Nelson et al.) "Cyclodextrins in Dental Products", U.S. Pat. No. 7,025,984 (Apr. 11, 2006 Jandacek et al.) "Compositions and Methods for Body Weight Management", U.S. Pat. No. 7,115,297 (Oct. 3, 2006 Stillman) "Nutritionally Fortified Liquid Composition with Added Value Delivery Systems/Elements/Additives", U.S. Pat. No. 7,138,107 (Nov. 21, 2006 Adams et al) "Inhibition of Olfactory Neurosensory Function to Treat Eating Disorders and Obesity", U.S. Pat. No. 7,229,658 (Jun. 12, 2007 Inoue et al.) "Compositions Containing Sucralose and Application Thereof", U.S. Pat. No. 7,238,380 (Jul. 3, 2007 Stillman)

"Water Containing Soluble Fiber", U.S. Pat. No. 7,276,229 (Oct. 2, 2007 Baker et al.) "Oral Compositions", U.S. Pat. No. 7,402,400 (Jul. 22, 2008 Zuker et al.) "Mammalian Sweet Taste Receptors", U.S. Pat. No. 7,524,877 (Apr. 28, 2009 Rosenfeld et al.) "Compounds for Use in Weight Loss and Appetite Suppression in Humans", U.S. Pat. No. 7,541,356 (Jun. 2, 2009 Rosenfeld et al.) "Compounds for Use in Weight Loss and Appetite Suppression in Humans", U.S. Pat. No. 7,632,517 (Dec. 15, 2009 Dugger et al.) "Buccal Polar and Non-Polar Spray Containing Zolpidem", U.S. Pat. No. 7,851,005 (Dec. 14, 2010 Bingley et al.) "Taste Potentiator Compositions and Beverages Containing Same", U.S. Pat. No. 7,851,006 (Dec. 14, 2010 Bingley et al.) "Taste Potentiator Compositions and Beverages Containing Same", U.S. Pat. No. 7,879,376 (Feb. 1, 2011 Boghani et al.) "Taste Potentiator Compositions and Edible Confectionery and Chewing Gum Products Containing Same", U.S. Pat. No. 7,977,060 (Jul. 12, 2011 Zuker et al.) "Mammalian Sweet Taste Receptors", U.S. Pat. No. 8,119,359 (Feb. 21, 2012 Adler et al.) "Methods of Identifying Sweet Taste Modulators", U.S. Pat. No. 8,143,215 (Mar. 27, 2012 Hirsch) "Method of Promoting Weight Loss", U.S. Pat. No. 8,198,048 (Jun. 12, 2012 Zuker et al.) "Mammalian Sweet Taste Receptors", U.S. Pat. No. 8,217,001 (Jul. 10, 2012 Cowley et al.) "Modification of Feeding Behavior", U.S. Pat. No. 8,236,285 (Aug. 7, 2012 Dugger et al.) "Buccal, Polar and Non-Polar Spray Containing Zolpidem", and U.S. Pat. No. 8,287,898 (Oct. 16, 2012 Jandacek et al.) "Compositions and Methods for Body Weight Management".

Examples of prior art that appear to be best classified in this category also include U.S. patent applications: 20020187204 (Dec. 12, 2002 Alviar et al.) "Diet Composition and Method of Weight Management", 20030113310 (Jun. 19, 2003 Van Laere et al.) "Method for the Treatment of Obesity, Overweight and Fluctuations in Blood Insuline and/or Glucose Levels", 20040071801 (Apr. 15, 2004 Edell et al.) "Herbal Formulation of Gymnema Sylvestre as a Dietary Aid", 20040156920 (Aug. 12, 2004 Kane) "Extracts From Plant and Non-Plant Biomass and Uses Thereof", 20040192760 (Sep. 30, 2004 Whittle et al.) "Pharmaceutical Formulations", 20040247702 (Dec. 9, 2004 Rajendran et al.) "Caralluma Extract Products and Processes for Making the Same", 20050053555 (Mar. 10, 2005 Pederson) "Appetite Control Compositions and Methods of Use", 20060105068 (May 18, 2006 Fleischner) "Dietary Supplement Formulations Containing Hoodia Gordonii", 20060193795 (Aug. 31, 2006 Zuckerman) "Appetite Suppressant Mouth Spray", 20070104805 (May 10, 2007 Udell) "Compositions of Hoodia Gordonii and Pinolenic Acid Derivatives", 20070160735 (Jul. 12, 2007 Stillman) "Water Containing Soluble Fiber", 20070196436 (Aug. 23, 2007 Abrahams et al.) "Process for Preparing an Edible Composition Comprising Steroidal Glycosides", 20080014327 (Jan. 17, 2008 Stillman) "Water Containing Soluble Fiber", 20080102143 (May 1, 2008 Freis et al.) "Uses for the Extract of a Plant of the Family Asclepiadaceae", 20080138447 (Jun. 12, 2008 Riggins et al.) "Method for Administering Appetite Suppressant and Composition Thereof", 20080152705 (Jun. 26, 2008 Udell et al.) "Corosolic Acid Formulation and Its Application for Weight-Loss Management and Blood Sugar Balance", and 20080255093 (Oct. 16, 2008 Tam et al.) "Compositions and Methods for Treating Obesity and Related Disorders".

Examples of prior art that appear to be best classified in this category also include U.S. patent applications: 20100098783 (Apr. 22, 2010 Sommerfeld et al.) "Appetite Suppressant Composition", 20100215584 (Aug. 26, 2010 Passe) "Compositions and Methods of Modulating the Taste and Smell Receptors and Screening Methods Therefore", 20100267643 (Oct. 21, 2010 Baron et al.) "Chemosensory Receptor Ligand-Based Therapies", 20100316768 (Dec. 16, 2010 Stillman) "Nutritionally Fortified Liquid Composition with Added Value Delivery Systems/Elements/Additives", 20110065660 (Mar. 17, 2011 Baron et al.) "Chemosensory Receptor Ligand-Based Therapies", 20110082407 (Apr. 7, 2011 Aronne) "Combination Therapies for the Treatment of Obesity", 20110104336 (May 5, 2011 Stillman) "Water Containing Soluble Fiber", 20110136909 (Jun. 9, 2011 Imada et al.) "Method for Suppressing Excessive Appetite", 20110166065 (Jul. 7, 2011 Bhanot et al.) "Modulation Of Glucose-6-Phosphatase Translocase Expression", 20110224155 (Sep. 15, 2011 Tachdjian et al.) "Modulation of Chemosensory Receptors and Ligands Associated Therewith", 20110230502 (Sep. 22, 2011 Tachdjian et al.) "Modulation of Chemosensory Receptors and Ligands Associated Therewith", 20110244514 (Oct. 6, 2011 Zuker et al.) "Mammalian Sweet Taste Receptors", 20120040893 (Feb. 16, 2012 Cowley et al.) "Modification of Feeding Behaviour", 20120094942 (Apr. 19, 2012 Baron et al.) "Chemosensory Receptor Ligand-Based Therapies", 20120115778 (May 10, 2012 Karsenty et al.) "Methods of Suppressing Appetite by the Administration of Antagonists of the Serotonin HTR1a or HTR2b Receptors or Inhibitors of TPH2", 20120157409 (Jun. 21, 2012 Cherkassky) "Appetite Suppressant Product and Method", 20120177730 (Jul. 12, 2012 Baron et al.) "Chemosensory Receptor Ligand-Based Therapies", and 20120208748 (Aug. 16, 2012 Chen et al.) "Peptide Compositions and Methods for Treating Patients". Examples of prior art that appear to be best classified in this category also include EP 1685834 "Use of Pinolenic Acid for the Treatment Of Obesity" and EP 2072048 "Use of Pinolenic Acid for the Treatment Of Obesity".

3. Substance Sprinkled on Food

Prior art in this category includes manufactured and specifically-isolated substances or compounds that a person voluntarily adds to their food slightly before or during food consumption in order to modify their food consumption. For example, this category includes substances that a person sprinkles on their food with the intent of suppressing their appetite. In various examples, such a substance can change the flavor, smell, or appearance of food with the intent of dampening a person's appetite.

The success of art in this category in modifying food consumption depends on the ability of the sprinkled substance to actually modify the person's food consumption and the consistency with which the person regularly sprinkles the substance on food each time they eat. This can be problematic, especially if the substance makes food taste less appealing or if a specific food has a surface to which the sprinkled substance does not adhere. Also, if a person does not have enough willpower and discipline to avoid eating unhealthy food in the first place, then it is not clear that this person would have enough willpower and discipline to always sprinkle an appetite-suppressing additive on their food each time that they eat.

Examples of prior art that appear to be best classified in this category include: U.S. Pat. No. 5,603,971 (Feb. 18, 1997 Porzio et al.) "Encapsulation Compositions", U.S. Pat. No. 6,112,749 (Sep. 5, 2000 Hall et al.) "Flavor Dot Odorizer and Method", U.S. Pat. No. 6,902,751 (Jun. 7, 2005 Schleifenbaum et al.) "Encapsulated Flavorings", U.S. Pat. No. 7,727,546 (Jun. 1, 2010 Moneymaker et al.) "Nutrient System for Individualized Responsive Dosing Regimens", U.S. Pat. No. 7,820,208 (Oct. 26, 2010 Hirsch) "Method of Assaying Satiety Enhancing Tastants (Alan Hirsch)", U.S.

Pat. No. 8,143,062 (Mar. 27, 2012 Hirsch) "Method and Composition for Enhancing Weight Loss", and U.S. Pat. No. 8,143,215 (Mar. 27, 2012 Hirsch) "Method of Promoting Weight Loss"; and U.S. patent applications 20040231299 (Nov. 25, 2004 Yakushigawa et al.) "Flavoring System and Method", 20080075813 (Mar. 27, 2008 Smith et al.) "Seasoning and Method for Enhancing and Potentiating Food Flavor Utilizing Microencapsulation While Reducing Dietary Sodium Intake", 20090123380 (May 14, 2009 Hirsch) "Method of Assaying Satiety Enhancing Tastants (Alan Hirsch)", 20090123524 (May 14, 2009 Hirsch) "Packaged Satiety Enhancing Composition (Alan Hirsch)", 20090123579 (May 14, 2009 Hirsch) "Method of Promoting Weight Loss (Alan Hirsh)", 20090214445 (Aug. 27, 2009 Boghani et al.) "Delivery Systems for Managing Release of Functional Ingredients in an Edible Composition", and 20120058217 (Mar. 8, 2012 Patty) "Taste Deterrent and Diet Method".

4. Manually-Administered Spray or Pulse

This category of prior art includes oral and nasal sprays, mists, and pulses that contain a consumption-modifying substance. As was the case with art involving a sprinkled food additive, the success of art in this category depends on the ability of the sprayed substance to actually modify a person's food consumption and the regularity with which the person sprays the substance into their mouth or nose every time that they eat. In an example, a sprayed substance can be absorbed into tissue for a systemic (pharmacologic) appetite-suppressant effect. In another example, a sprayed substance can be released into a person's oral cavity or nasal cavities for a localized anesthetic effect. In an example, this substance can mask or block the taste or smell of food.

In order for this approach to work, a person must exercise consistent voluntary compliance in spraying the substance into their mouth or nose prior to consumption of (selected types of) food. However, if a person does not have enough willpower and discipline to avoid eating unhealthy food in the first place, then it is not clear that this person would have enough willpower and discipline to consistently spray something into their nose or mouth before every meal or snack.

Examples of prior art that appear to be best classified in this category include U.S. patents: U.S. Pat. No. 4,935,225 (Jun. 19, 1990 Curtis et al.) "Appetite Suppressant Dentifrice", U.S. Pat. No. 5,284,132 (Feb. 8, 1994 Geier) "Device for the Transnasal or Oral Administration of Drugs or the Like", U.S. Pat. No. 5,456,677 (Oct. 10, 1995 Spector) "Method for Oral Spray Administration of Caffeine", U.S. Pat. No. 6,715,485 (Apr. 6, 2004 Djupesland) "Nasal Delivery Device", U.S. Pat. No. 7,935,065 (May 3, 2011 Martin et al.) "Oral Device", and patent application 20050037031 (Feb. 17, 2005 Jackson) "Methods for Diet and Weight Control by Altering the Senses of Smell and Taste".

5. Substance-Emitting Lipstick or Toothpaste

This category of prior art includes lipstick or toothpaste that releases a consumption-modifying substance. In order to be effective, the lipstick or toothpaste must release a genuinely consumption-modifying substance in sufficient amounts over a long-enough duration to affect food consumption. If it only releases the substance for a short time or tapers off rapidly, then the lipstick or toothpaste must be applied frequently which relies heavily on the person's voluntary compliance. If it releases the substance for a long time, then the prior art does not disclose how this approach would enable selective modification of unhealthy food consumption; it would affect consumption of healthy foods as well as unhealthy foods. In order for this approach to be effective: the substance in the lipstick or toothpaste must really reduce food consumption when used; the substance must be released from the lipstick or toothpaste in sufficient quantity, and over a sufficient duration, to be effective; and the person must have consistent voluntary compliance in using the lipstick or toothpaste. Also, many people do not wear lipstick. For these reasons, art in this category is limited for consistent modification of food consumption.

Examples of prior art that appear to be best classified in this category include: U.S. patent: U.S. Pat. No. 6,485,710 (Nov. 26, 2002 Zuckerman) "Appetite Suppressant Toothpaste" and U.S. Pat. No. 7,247,323 (Jul. 24, 2007 George et al.) "Delivery System for Appetite Suppressant"; and U.S. patent applications 20030095936 (May 22, 2003 Light) "Lip Gloss Composition", 20070042058 (Feb. 22, 2007 George et al.) "Delivery System for Appetite Suppressant", and 20100135945 (Jun. 3, 2010 Murdock et al.) "Gymnema-Containing Lip Balm Compositions and Associated Method".

6. Substance-Emitting Adhesive Patch in the Mouth

Prior art in this category includes temporary substance-emitting patches that a person attaches (e.g. through adhesion) within their oral cavity in order to modify their food consumption. In various examples, such a patch can be attached to a person's upper palate or teeth. In an example, this substance can be absorbed into tissue (such as through mucosal delivery) to cause a systemic (pharmacological) appetite-suppressant effect. In an example, this substance can be released into the person's oral cavity or nasal cavity to cause a localized anesthetic effect. The intent is to reduce a person's appetite by gradual emission of an appetite-suppressing substance.

The success of this approach depends on: whether the person regularly uses and replaces the patch, whether the patch emits the substance for a sufficiently long time and in a sufficiently consistent dosage to affect all of a person's meals throughout the day, and whether the substance actually reduces the person's appetite even when consistently emitted. If the effect of the patch lasts for a short time, then the patch must be replaced frequently, which requires high voluntary compliance by the person. If the effect lasts for a long time, then the prior art does not disclose how this approach would enable selective consumption modification (allowing healthy food but discouraging unhealthy food). All of these factors make this approach problematic.

Examples of prior art that appear to be best classified in this category include: U.S. Pat. No. 3,972,995 (Aug. 3, 1976 Tsuk et al.) "Dosage Form", U.S. Pat. No. 4,059,686 (Nov. 22, 1977 Tanaka et al.) "Pharmaceutical Preparation for Oral Cavity Administration", U.S. Pat. No. 4,292,299 (Sep. 29, 1981 Suzuki et al.) "Slow-Releasing Medical Preparation to be Administered by Adhering to a Wet Mucous Surface", U.S. Pat. No. 4,615,697 (Oct. 7, 1986 Robinson) "Bioadhesive Compositions and Methods of Treatment Therewith", U.S. Pat. No. 4,764,378 (Aug. 16, 1988 Keith et al.) "Buccal Drug Dosage Form", U.S. Pat. No. 6,387,408 (May 14, 2002 Illum et al.) "Adhesive Drug Delivery Composition", U.S. Pat. No. 6,488,953 (Dec. 3, 2002 Halliday et al.) "Oral Transmucosal Delivery", and U.S. Pat. No. 8,173,113 (May 8, 2012 Scholz et al.) "Bioadhesive Composition and Patch"; and U.S. patent applications 20040109886 (Jun. 10, 2004 Rigby) "Methods and Apparatus for Transdermal Delivery of Abusable Drugs with a Deterrent Agent", 20070104783 (May 10, 2007 Domb et al.) "Double-Layered Absorbable Solid Compositions for the Topical Treatment of Oral Mucosal Disorders", 20090130178 (May 21, 2009 Oronsky et al.) "Formulation for Decreasing Tobacco, Alcohol, Drug or Food Consumption", and 20120015021 (Jan. 19, 2012 Mizrahi et al.) "Anti-Appetite Adhesive Compositions".

7. Dissolving Film in Mouth

This category of prior art includes dissolvable films which a person inserts into their mouth and which slowly release a consumption-modifying substance. Unlike art in the prior category, these films are not attached to tissue within a person's oral cavity. Since inserting and ingesting the film can interfere with the process of food consumption, a person must have sufficient willpower and discipline to insert the film in advance of eating. Further, if the substance in the mouth is diluted by food consumption, then the person may have to insert a dissolvable film multiple times during the same meal.

In order for this approach to work, the person must exercise consistent voluntary compliance in inserting the film into their mouth before eating (selected types of) food. However, if a person does not have enough willpower and discipline to avoid eating unhealthy food in the first place, then it is not clear that this person would have enough willpower and discipline to consistently insert a dissolvable film into their mouth before each snack or meal.

Examples of prior art that appear to be best classified in this category include U.S. patents: U.S. Pat. No. 6,419,903 (Jul. 16, 2002 Xu et al.) "Breath Freshening Film" and U.S. Pat. No. 7,972,618 (Jul. 5, 2011 Fuisz et al.) "Edible Water-Soluble Film Containing a Foam Reducing Flavoring Agent"; and patent application 20040131661 (Jul. 8, 2004 Auffret et al.) "Process for Making Orally Consumable Dosage Forms".

8. Tablet or Gum in Mouth

This category of prior art includes tablets, lozenges, and chewing gum that are inserted into the mouth and slowly release a consumption-modifying substance. Since inserting and ingesting a tablet, lozenge, or chewing gum can interfere with the process of food consumption, the person must have sufficient willpower and discipline to insert the tablet, lozenge, or chewing gum well in advance of eating. Further, if the substance in the mouth is diluted by food consumption, then the person may have to insert a tablet, lozenge, or chewing gum multiple times during the same meal.

In order for this approach to work, the person must exercise consistent voluntary compliance in inserting the tablet, lozenge, or chewing gum into their mouth before eating (selected types of) food. However, if a person does not have enough willpower and discipline to avoid eating unhealthy food in the first place, then it is not clear that this person would have enough willpower and discipline to consistently pop a tablet, lozenge, or chewing gum into their mouth before each snack or meal.

Examples of prior art that appear to be best classified in this category include: U.S. Pat. No. 3,856,942 (Dec. 24, 1974 Murphy) "Appetite Control Composition", U.S. Pat. No. 3,911,099 (Oct. 7, 1975 Defoney et al.) "Long-Acting Articles for Oral Delivery and Process", U.S. Pat. No. 4,039,653 (Aug. 2, 1977 Defoney et al.) "Long-Acting Articles for Oral Delivery and Process", U.S. Pat. No. 4,822,597 (Apr. 18, 1989 Faust et al.) "Anesthetic-Containing Chewing Gum Compositions", U.S. Pat. No. 5,942,244 (Aug. 24, 1999 Friedman et al.) "Local Oral Herbal Slow Release Tablets", U.S. Pat. No. 6,183,775 (Feb. 6, 2001 Ventouras) "Buccal Delivery System", U.S. Pat. No. 6,280,761 (Aug. 28, 2001 Santus) "Nicotine Lozenge (Santus)", U.S. Pat. No. 6,893,654 (May 17, 2005 Pinney et al.) "Two-Stage Transmucosal Medicine Delivery System for Symptom Relief", U.S. Pat. No. 6,949,264 (Sep. 27, 2005 Mcgrew et al.) "Nutraceuticals or Nutritional Supplements and Method of Making", U.S. Pat. No. 7,851,000 (Dec. 14, 2010 Boghani et al.) "Taste Potentiator Compositions and Edible Confectionery and Chewing Gum Products Containing Same", and U.S. Pat. No. 8,236,348 (Aug. 7, 2012 Gin et al.) "Long-Lasting, Flavored Dosage Forms for Sustained Release of Beneficial Agents within the Mouth"; and U.S. patent applications 20040151771 (Aug. 5, 2004 Gin et al.) "Long-Lasting, Flavored Dosage Forms for Sustained Release of Beneficial Agents Within the Mouth", 20040247669 (Dec. 9, 2004 Gin et al.) "Long-Lasting Flavored Dosage Forms for Sustained Release of Beneficial Agents within the Mouth", 20050112149 (May 26, 2005 Belote et al.) "Single-Dose Taste Inhibitor Units", 20070048369 (Mar. 1, 2007 Foreman et al.) "Mucosal Delivery Tablet", 20090081291 (Mar. 26, 2009 Gin et al.) "Sustained Release Dosage Forms for Delivery of Agents to an Oral Cavity of a User", and 20120195954 (Aug. 2, 2012 Maynard) "Method of Reducing Appetite".

9. Intraoral Drug Delivery

Prior art in this category includes pharmaceutical compounds that are delivered intra-orally. In an example, a compound can be delivered locally (e.g. by injection) in order to selectively target intraoral tissue. In another example, a compound can be delivered systemically via mucosal absorption. This approach depends on the ability of the pharmaceutical compound to actually reduce a person's appetite and on patient compliance with intra-oral drug administration.

Examples of prior art that appear to be best classified in this category include: U.S. Pat. No. 5,194,003 (Mar. 16, 1993 Garay et al.) "Removable Device for Delivering Beneficial Agents Orally" and U.S. Pat. No. 8,181,655 (May 22, 2012 Bardach et al.) "Therapeutic and Protective Dental Device Useful as an Intra-Oral Delivery System"; and patent application 20080044797 (Feb. 21, 2008 Bardach et al.) "Inserts for Use with Oral Appliances".

10. Motion Guided or Directed Pill

Prior art in this category includes "smart pills" whose movement, placement, attachment, and/or activation within specific body structures can be remotely guided and controlled. In an example, such pills can be guided to a particular location along a person's gastrointestinal tract and then activated when they reach this location. Such activation can include remote-controlled attachment to specific body tissue and/or remote-controlled localized emission of a pharmaceutical compound. In an example, local intragastric drug delivery can be more targeted and effective than systemic drug delivery.

Examples of prior art that appear to be best classified in this category include: U.S. Pat. No. 8,109,920 (Feb. 7, 2012 Boyden et al.) "Medical or Veterinary Digestive Tract Utilization Systems and Methods", U.S. Pat. No. 8,219,171 (Jul. 10, 2012 Benoist) "Delivery Device for Implantable Monitor", U.S. Pat. No. 8,303,573 (Nov. 6, 2012 Boyden et al.) "Medical or Veterinary Digestive Tract Utilization Systems and Methods", and U.S. Pat. No. 8,333,754 (Dec. 18, 2012 Boyden et al.) "Medical or Veterinary Digestive Tract Utilization Systems and Methods"; and U.S. patent applications 20110160129 (Jun. 30, 2011 Imran) "Therapeutic Agent Preparations for Delivery Into a Lumen of the Intestinal Tract Using a Swallowable Drug Delivery Device", 20110160699 (Jun. 30, 2011 Imran) "Swallowable Drug Delivery Device and Methods of Drug Delivery", 20120010590 (Jan. 12, 2012 Imran) "Swallowable Drug Delivery Device and Method of Delivery", 20120165792 (Jun. 28, 2012 Ortiz et al.) "Pill Catchers", 20120165793

(Jun. 28, 2012 Ortiz et al.) "Pill Catchers", 20120165794 (Jun. 28, 2012 Ortiz et al.) "Pill Catchers", and 20120165796 (Jun. 28, 2012 Ortiz et al.) "Pill Catchers".

11. General Implanted Drug Pump

This category of prior art includes implantable drug pumps that are used to achieve a consumption-modifying effect. Not all implantable drug pumps are reviewed here, only those which are particularly relevant to modification of food consumption and related metabolic processes. In an example, an implantable pump can pump a drug into a location along the person's digestive tract. In an example, an implantable drug pump can pump a pharmaceutical agent into a person's brain. In an example, an implantable pump can deliver a pharmaceutical agent into a person's blood stream. For implanted medical devices for which drug delivery appears to be the secondary mode of action, we have included such art in separate categories which follow that are primarily identified by their primary (non-drug device) mode of action.

It is not clear from the prior art how such drug pumps can be selectively used to allow consumption of healthy food, but discourage consumption of unhealthy food. Also, the prior art does not disclose how such devices could be used to allow moderate consumption, but limit excess consumption, of certain foods. Prior art in this category is much less dependent on patient compliance than art in many of the previous categories, but still critically depends on the effectiveness of a drug in modifying food consumption and/or absorption without intolerable side effects.

Examples of prior art that appear to be best classified in this category include: U.S. Pat. No. 4,925,446 (May 15, 1990 Garay et al.) "Removable Inflatable Intragastrointestinal Device for Delivering Beneficial Agents", U.S. Pat. No. 5,011,472 (Apr. 30, 1991 Aebischer et al.) "Implantable Delivery System for Biological Factors", U.S. Pat. No. 5,318,519 (Jun. 7, 1994 Wilk) "Method and Apparatus for Supplying Nutrition", U.S. Pat. No. 5,643,207 (Jul. 1, 1997 Rise) "Implantable Techniques for Infusing a Therapeutic Agent with Endogenous Bodily Fluid", U.S. Pat. No. 5,730,722 (Mar. 24, 1998 Wilk) "Method and Apparatus for Supplying a Medical Treatment Composition to a Patient", U.S. Pat. No. 7,043,295 (May 9, 2006 Starkebaum) "Methods and Apparatus for Delivering a Drug Influencing Appetite for Treatment of Eating Disorders", U.S. Pat. No. 7,108,680 (Sep. 19, 2006 Rohr et al.) "Closed-Loop Drug Delivery System", U.S. Pat. No. 7,790,671 (Sep. 7, 2010 Stojanovic-Susulic et al.) "Implantable Pump for Protein Delivery for Obesity Control by Drug Infusion into the Brain", U.S. Pat. No. 8,066,689 (Nov. 29, 2011 Mitelberg et al.) "Methods and Systems for Submucosal Implantation of a Device for Diagnosis and Treatment with a Therapeutic Agent", and U.S. Pat. No. 8,252,744 (Aug. 28, 2012 Stojanovic-Susulic et al.) "Implantable Pump for Protein Delivery for Obesity Control by Drug Infusion into the Brain"; and U.S. patent applications 20030171711 (Sep. 11, 2003 Rohr et al.) "Closed-Loop Drug Delivery System", 20050038415 (Feb. 17, 2005 Rohr et al.) "Method and Apparatus for the Treatment of Obesity", 20050096514 (May 5, 2005 Starkebaum) "Gastric Activity Notification", 20070082843 (Apr. 12, 2007 Stojanovic-Susulic et al.) "Implantable Pump for Protein Delivery for Obesity Control by Drug Infusion into the Brain", 20100145301 (Jun. 10, 2010 Magal) "Spray Administration of Compositions Including Active Agents Such as Peptides to the Gastrointestinal Tract", and 20120071812 (Mar. 22, 2012 Mitelberg et al.) "Methods and Systems for Submucosal Implantation of a Device for Diagnosis and Treatment with a Therapeutic Agent".

Examples of prior art that appear to be best classified in this category also include EP 1504778 "Implantable Pump for the Treatment of Obesity", WO 2002085428 ("Implantable Osmotic Pump"), and WO 2003004034 ("Method for Inducing Analgesia Comprising Administration Alternatively of an Opioid Receptor Agonist and an Opioid Receptor Like Receptor 1 Agonist . . . ").

12. Food Purchasing Monitoring

Prior art in this category includes devices and methods that monitor what types of food a person purchases at the point of sale. Although there can be overlap, in some respects most art in this category is based on information technology, not biomedical technology. It is relatively easy to track food purchase transactions at a given store or with a given credit card. It can also be relatively easy to record the many items in a store that are marked with a bar code (or other type of product identifier).

However, this approach depends on two large assumptions. First, it assumes that a person buys everything that they eat at participating locations or with a selected card. This is violated if a person buys food at a non-participating location or eats food that someone else has bought. Second, it assumes that a person eats everything that they buy. This is violated if the person buys food for others (such as their family) and/or does not eat all the food that they buy. Also, timing differences between when a person buys food and when they eat that food can confound analysis of the relationship between food consumption and achievement of weight management objectives.

Examples of prior art that appear to be best classified in this category include: U.S. Pat. No. 5,412,564 (May 2, 1995 Ecer) "System and Method for Diet Control", U.S. Pat. No. 7,769,635 (Aug. 3, 2010 Simons-Nikolova) "Weight Management System with Simple Data Input", and U.S. Pat. No. 7,999,674 (Aug. 16, 2011 Kamen) "Device and Method for Food Management"; and U.S. patent applications 20080255955 (Oct. 16, 2008 Simons-Nikolova) "Weight Management System with Simple Data Input", 20100205209 (Aug. 12, 2010 Jokinen) "Method and System for Monitoring a Personal Intake", and 20130006807 (Jan. 3, 2013 Bai et al.) "Guideline-Based Food Purchase Management".

13. Food Scale

Prior art in this category includes automated food scales with a computer interface that records the weight of a specific portion of food before it is consumed. Sometimes such food scales are stand-alone devices. Sometimes such food scales are incorporated into place settings (such as a specialized food-weighing plate, glass, or utensil). The vast majority of prior art in this category depends on some type of specific action by the person to record the type of food that is on the scale. Once the type of food is manually entered, converting it into estimates of specific nutrients or calories can then be done in a relatively straight-forward manner using a computerized database.

Prior art in this category has the same compliance problems that plague other manual food logging methods. Will a person really weigh each bit of food on which they snack throughout the day? Will they bring a food scale to social eating situations and use it there? Will a person consistently identify each type of food that they eat and enter this information into the scale device? These questions highlight some of the potential disadvantages of this category of art for monitoring food consumption.

Examples of prior art that appear to be best classified in this category include: U.S. Pat. No. 4,387,777 (Jun. 14, 1983 Ash) "Calorie Counting Method and Apparatus", U.S. Pat. No. 4,875,533 (Oct. 24, 1989 Mihara et al.) "Automatic Weight Detecting Device", U.S. Pat. No. 4,911,256 (Mar. 27, 1990 Attikiouzel) "Dietetic Measurement Apparatus", U.S. Pat. No. 5,033,561 (Jul. 23, 1991 Hettinger) "Diet Control Device", U.S. Pat. No. 5,233,520 (Aug. 3, 1993 Kretsch et al.) "Method and System for Measurement of Intake of Foods, Nutrients and Other Food Components in the Diet", U.S. Pat. No. 5,388,043 (Feb. 7, 1995 Hettinger) "Diet and Behavioral Control Device", U.S. Pat. No. 5,817,006 (Oct. 6, 1998 Bergh et al.) "Method and Apparatus for Measurement of Eating Speed", and U.S. Pat. No. 6,425,862 (Jul. 30, 2002 Brown) "Interactive Furniture for Dieters"; and U.S. patent applications 20020124017 (Sep. 5, 2002 Mault) "Personal Digital Assistant with Food Scale Accessory", 20060263750 (Nov. 23, 2006 Gordon) "Personal Nutrition Control Devices", 20070028453 (Feb. 8, 2007 Crow) "Portion Control Serving Utensils", 20070050058 (Mar. 1, 2007 Zuziak et al.) "Placemat for Calculating and Monitoring Calorie Intake", 20070173703 (Jul. 26, 2007 Lee et al.) "Method, Apparatus, and Medium for Managing Weight by Using Calorie Consumption Information", and 20120055718 (Mar. 8, 2012 Chen) "Electronic Scale for Recording Health Administration Data".

14. Portion Size Control

Prior art in this category includes specific-size food containers, place settings, and/or serving utensils that standardize the portion sizes and/or bite sizes of food that a person consumes. Such prior art is heavily dependent on specific human actions (apart from the actual act of eating) to be successful. Food must be consistently stored, apportioned, served, and eaten using the specific containers, place settings, and/or serving utensils. Hand-held snacks consumed from a bag, for example, are not easily monitored by this approach. Also, a person can easily prepare food without using the specific containers. Further, such art by itself is not useful for food identification. Food identification requires further specific human action. For these reasons, this approach has significant limitations for consistent measurement and modification of food intake.

Examples of prior art that appear to be best classified in this category include: U.S. Pat. No. 4,075,769 (Feb. 28, 1978 Young) "Method and Article for Weight Reduction" and U.S. Pat. No. 7,044,739 (May 16, 2006 Matson) "System for Controlled Nutrition Consumption"; and U.S. patent applications 20050014111 (Jan. 20, 2005 Matson) "System for Controlled Nutrition Consumption", 20100125181 (May 20, 2010 Hyde et al.) "Food Content Detector", 20120031805 (Feb. 9, 2012 Stolarczyk) "Daily Meal Planning System", 20120077154 (Mar. 29, 2012 Highet et al.) "Incrementally-Sized Standard-Sized Eating-Ware System for Weight Management", and 20120144912 (Jun. 14, 2012 Kates et al.) "Portion Control System for Weight Loss and Maintenance".

15. Mouth Size or Function Modification

This category of prior art includes devices and methods that limit mouth capacity or function so that a person eats less. In an example, a bulky device can be attached within a person's oral cavity in order to reduce the size of the cavity so that a person eats less food with each mouthful. This assumes that the person will not simply eat more mouthfuls to compensate. In another example, a device can be attached within the person's mouth to create resistance to chewing motion so that eating takes more work. The intent is that the person will eat less if eating requires more effort. In an example, a device can block consumption of solid food. This assumes that blocking solid food is an effective way to modify a person's diet to manage their weight. In an example, a device can physically cover or shield a person's tongue and taste buds so that they eat less. This assumes that such a device will be tolerated and will not be removed.

It is not clear from the prior art how such devices could be selectively used to allow consumption of healthy food, but discourage consumption of unhealthy food. Also, the prior art does not disclose how such devices would allow moderate consumption of certain foods but limit excess consumption of those foods. Also, if such a device is removable, then it requires consistent voluntary compliance by the person in order to be effective.

Examples of prior art that appear to be best classified in this category include: U.S. Pat. No. 3,818,906 (Jun. 25, 1974 Stubbs) "Apparatus for Controlling Eating and Smoking Habits", U.S. Pat. No. 4,471,771 (Sep. 18, 1984 Brown) "Oral Weight Control Device", U.S. Pat. No. 4,738,259 (Apr. 19, 1988 Brown et al.) "Dental Appliance for Weight Control", U.S. Pat. No. 5,924,422 (Jul. 20, 1999 Gustafson) "Oral Device to Aid Weight Control", U.S. Pat. No. 5,979,449 (Nov. 9, 1999 Steer) "Oral Appliance Device and Method for use Thereof for Appetite Suppression", U.S. Pat. No. 6,422,243 (Jul. 23, 2002 Daram) "Taste Bud Shield and Method of Using Same", and U.S. Pat. No. 8,230,865 (Jul. 31, 2012 Shalon) "Palatal Implant"; and U.S. patent applications 20030059737 (Mar. 27, 2003 Hall) "Obesity Treatment Aid", 20050287495 (Dec. 29, 2005 Longley) "Dental Appliance for Weight Management", and 20120109051 (May 3, 2012 Harrell) "Devices, Methods, and Kits for Taste Modification and Controlling Food Intake".

16. Chewing and Swallowing Monitoring

Prior art in this category includes devices that monitor the chewing and/or swallowing actions that are associated with food consumption. In various examples, such devices can monitor chewing and/or swallowing by a method selected from the group consisting of: monitoring and analyzing sounds from a person's body to differentiate chewing and/or swallowing sounds from other sounds such as speaking; monitoring electromagnetic energy from a person's mouth muscles or internal gastrointestinal organs; and monitoring movement of a person's mouth or internal gastrointestinal organs.

Prior art in this category can be more automatic than art in many of the prior categories with respect to detecting when a person consumes food. Some art in this category can even generally differentiate between consumption of solid food vs. liquid food based on differences in sonic energy or electromagnetic energy. However, art in this category is generally very limited with respect to more-specific identification of what type of food a person is consuming. Also, a person can confuse or circumvent such a device by putting generally-solid food in a blender or by freezing generally-liquid food. Art in this category still relies on specific human actions to record food type apart from the actual action of eating. Also, since there can be different amounts of food per swallow, determination of food quantity based on the number of swallows can be problematic. Accordingly, prior art in this category has a number of limitations for measuring and modifying the types and quantities of food consumed.

Examples of prior art that appear to be best classified in this category include: U.S. Pat. No. 4,355,645 (Oct. 26, 1982 Mitani et al.) "Device for Displaying Masticatory Muscle Activities", U.S. Pat. No. 5,067,488 (Nov. 26, 1991 Fukada et al.) "Mastication Detector and Measurement Apparatus and Method of Measuring Mastication", U.S. Pat. No.

5,263,491 (Nov. 23, 1993 Thornton) "Ambulatory Metabolic Monitor", U.S. Pat. No. 6,135,950 (Oct. 24, 2000 Adams) "E-fit Monitor", U.S. Pat. No. 7,330,753 (Feb. 12, 2008 Policker et al.) "Analysis of Eating Habits", U.S. Pat. No. 7,840,269 (Nov. 23, 2010 Policker et al.) "Analysis of Eating Habits", U.S. Pat. No. 7,840,269 (Nov. 23, 2010 Policker et al.) "Analysis of Eating Habits", and U.S. Pat. No. 7,914,468 (Mar. 29, 2011 Shalon et al.) "Systems and Methods for Monitoring and Modifying Behavior"; and U.S. patent applications 20040147816 (Jul. 29, 2004 Policker et al.) "Analysis of Eating Habits", 20050283096 (Dec. 22, 2005 Chau et al.) "Apparatus and Method for Detecting Swallowing Activity", 20060064037 (Mar. 23, 2006 Shalon et al.) "Systems and Methods for Monitoring and Modifying Behavior", 20060064037 (Mar. 23, 2006 Shalon et al.) "Systems and Methods for Monitoring and Modifying Behavior", 20060064037 (Mar. 23, 2006 Shalon et al.) "Systems and Methods for Monitoring and Modifying Behavior", 20070299320 (Dec. 27, 2007 Policker et al.) "Analysis of Eating Habits", 20070299320 (Dec. 27, 2007 Policker et al.) "Analysis of Eating Habits", 20100076345 (Mar. 25, 2010 Soffer et al.) "Method, Device and System for Automatic Detection of Eating and Drinking", 20110125063 (May 26, 2011 Shalon et al.) "Systems and Methods for Monitoring and Modifying Behavior", 20110276312 (Nov. 10, 2011 Shalon et al.) "Device for Monitoring and Modifying Eating Behavior", 20120101874 (Apr. 26, 2012 Ben-Haim et al.) "Charger With Data Transfer Capabilities", and 20120203081 (Aug. 9, 2012 Leboeuf et al.) "Physiological and Environmental Monitoring Apparatus and Systems". Another example of prior art that appears to be best classified in this category is WO 2002082968 (Policker) "Analysis of Eating Habits."

17. Hand and/or Arm Motion Monitoring and Modification (Wrist)

This is the first of two categories of prior art wherein the intent is to detect and estimate food consumption by monitoring and analyzing hand and/or arm motion. This first category includes devices that are worn on a person's wrist or arm to directly monitor hand or arm motion. The second category (that follows this one) includes food utensils that indirectly monitor hand or arm motion when the utensil is held by a person and is used to bring food up to the person's mouth.

We have separated these devices into two categories because, even though they both monitor hand and arm motion, they have some different advantages and disadvantages. Devices worn on a person's wrist or arm have the advantage that they can be worn relatively continuously to monitor food consumption on a relatively continuous basis. Wrist-worn devices do not require that a person carry a specific motion-sensing food utensil everywhere that they go. However, a device that is worn on a person's wrist or arm can be subject to more false alarms (compared to a food utensil) due to non-food-consumption motions such as covering one's mouth when coughing, bringing a cigarette to one's mouth, or other hand-to-face gestures.

Many examples of devices in this category monitor hand and/or arm motion with an accelerometer. To the extent that there is a distinctive pattern of hand and/or arm movement associated with bringing food up to one's mouth, such a device can detect when food consumption is occurring. Such a device can also measure how rapidly or often the person brings their hand up to their mouth. A common use of such information is to encourage a person to eat at a slower pace. The idea that a person will eat less if they eat at a slower pace is based on the lag between food consumption and the feeling of satiety from internal gastric organs. If a person eats slower, then they will tend to not overeat past the point of internal identification of satiety. Detection of food consumption and approximate measurement of food consumption quantity that is based on hand or arm motion can also be useful for purposes other than slowing the pace of eating.

However, there are significant limitations to devices and methods in this category. First, such devices and methods do not provide good information concerning the types of food consumed. In this respect, they generally still rely on manual food identification methods. Second, although progress has been made to differentiate hand and/or arm motions that indicate food consumption from other types of hand and/or arm motions (such as covering one's mouth or brushing one's teeth), there remains imprecision with respect to quantification of food consumed based on analysis of hand-to-mouth movements. Third, it is tough to make such devices and methods tamper-resistant. A person can use non-conventional hand movements to eat, use a non-monitored hand to eat, eat larger bite sizes with each hand movement, remove the device from their wrist, or just ignore feedback from the device when they eat.

Examples of prior art that appear to be best classified in this category include: U.S. Pat. No. 3,885,576 (May 27, 1975 Symmes) "Wrist Band Including a Mercury Switch to Induce an Electric Shock", U.S. Pat. No. 4,965,553 (Oct. 23, 1990 DelBiondo et al.) "Hand-Near-Mouth Warning Device", U.S. Pat. No. 5,424,719 (Jun. 13, 1995 Ravid) "Consumption Control", U.S. Pat. No. 5,563,850 (Oct. 8, 1996 Hanapole) "Food Intake Timer", U.S. Pat. No. 8,112,281 (Feb. 7, 2012 Yeung et al.) "Accelerometer-Based Control of Wearable Audio Recorders", and U.S. Pat. No. 8,310,368 (Nov. 13, 2012 Hoover et al.) "Weight Control Device"; and U.S. patent applications 20060197670 (Sep. 7, 2006 Breibart) "Method and Associated Device for Personal Weight Control", 20080137486 (Jun. 12, 2008 Czarenk et al.) "Diet Watch", and 20100194573 (Aug. 5, 2010 Hoover et al.) "Weight Control Device".

18. Hand and/or Arm Motion Monitoring and Modification (Utensil)

Prior art in this category includes hand-held food serving utensils (such as forks or spoons) that indirectly monitor hand and/or arm motion to detect and estimate food consumption. Compared to the wrist-worn motion-detection devices that were discussed in the previous category, motion-detecting utensils can be less subject to false alarms because they are only used when the person consumes food. There are some recent examples of sophisticated food-analyzing utensils with sensors other than motion-sensors. Since they are qualitatively different than utensils with only motion sensors, we have put these more-sophisticated food-analyzing utensils in a separate category that follows in this categorization scheme.

Many examples of utensils in this category monitor motion with an accelerometer. Since the utensil is only used for food consumption, analysis of complex motion and differentiation of food consumption actions vs. other hand gestures is less important with a utensil than it is with a wrist-mounted device. Accordingly, some of the utensils in this category are quite simple. In the extreme, although crude, a single-axis accelerometer can be used. Other simple methods of measuring hand-to-mouth movement by a utensil are based on a simple holder or button on which the utensil is placed between mouthfuls. Another simple method is an internal fluid "horizontal level" or "lava lamp" feature attached to the utensil that is used to regulate the timing of hand-to-mouth motions.

The idea is that a person will eat less if they eat slower because there can be a lag between food consumption and identification of satiety by internal organs. If the person eats slower, then they will tend to not overeat past the point of internal identification of satiety. Detection of food consumption and approximate measurement of food consumption quantity based on hand or arm motion can also be useful for purposes other than slowing the pace of eating.

However, utensils with just a motion sensor do not provide good information concerning the type of food consumed. Also, compliance can be a huge issue for this approach. In order to be successful, a person has to bring the special utensil with them constantly and use it consistently whenever they eat. What happens when they are eating out in a social setting or eating a snack with their hands? For these reasons, special eating utensils with just a motion sensor are limited in their ability to consistently monitor and modify a person's food consumption.

Examples of prior art that appear to be best classified in this category include: U.S. Pat. No. 4,207,673 (Jun. 17, 1980 DiGirolamo et al.) "Cuttlery", U.S. Pat. No. 4,914,819 (Apr. 10, 1990 Ash) "Eating Utensil for Indicating When Food May be Eaten Therewith and a Method for Using the Utensil", U.S. Pat. No. 4,975,682 (Dec. 4, 1990 Kerr et al.) "Meal Minder Device", U.S. Pat. No. 5,299,356 (Apr. 5, 1994 Maxwell) "Diet Eating Utensil", U.S. Pat. No. 5,421,089 (Jun. 6, 1995 Dubus et al.) "Fork with Timer", and U.S. Pat. No. 8,299,930 (Oct. 30, 2012 Schmid-Schonbein et al.) "Devices, Systems and Methods to Control Caloric Intake"; and U.S. patent applications 20070098856 (May 3, 2007 LePine) "Mealtime Eating Regulation Device", 20080276461 (Nov. 13, 2008 Gold) "Eating Utensil Capable of Automatic Bite Counting", 20090253105 (Oct. 8, 2009 Lepine) "Device for Regulating Eating by Measuring Potential", 20100109876 (May 6, 2010 Schmid-Schonbein et al.) "Devices, Systems and Methods to Control Caloric Intake", 20100240962 (Sep. 23, 2010 Contant) "Eating Utensil to Monitor and Regulate Dietary Intake", and 20120115111 (May 10, 2012 Lepine) "Mealtime Eating Regulation Device".

19. Utensil with Sensor Other than Motion Sensor

Prior art in this category includes food utensils with sensors other than motion sensors that are used to measure food consumption. Such art in this category is relatively innovative and there are relatively few examples to date. Prior art in this category represents an important step toward automated measurement of food consumption. In various examples, a utensil in this category can measure the volume, mass, density, or general composition of a bite-size portion of food that is transported by the utensil to a person's mouth.

However, a significant limitation of art in this category is that it relies on a person's compliance. The person must use the utensil each time that they eat anything in order for the system to successfully monitor food consumption. If a person eats food without using the utensil (e.g. when dining in a social setting or when eating a snack by hand), then the system is unaware of this food consumption. This can be problematic and the prior art does not offer a solution to this problem.

Examples of prior art that appear to be best classified in this category include: U.S. Pat. No. 8,229,676 (Jul. 24, 2012 Hyde et al.) "Food Content Detector", U.S. Pat. No. 8,285,488 (Oct. 9, 2012 Hyde et al.) ibid., U.S. Pat. No. 8,290,712 (Oct. 16, 2012 Hyde et al.) ibid., U.S. Pat. No. 8,321,141 (Nov. 27, 2012 Hyde et al.) ibid., and U.S. Pat. No. 8,355,875 (Jan. 15, 2013 Hyde et al.) ibid.; and U.S. patent applications 20100125176 (May 20, 2010 Hyde et al.) ibid., 20100125177 (May 20, 2010 Hyde et al.) ibid., 20100125178 (May 20, 2010 Hyde et al.) ibid., 20100125179 (May 20, 2010 Hyde et al.) ibid., 20100125180 (May 20, 2010 Hyde et al.) ibid., 20100125181 (May 20, 2010 Hyde et al.) ibid., 20100125417 (May 20, 2010 Hyde et al.) ibid., 20100125418 (May 20, 2010 Hyde et al.) ibid., 20100125419 (May 20, 2010 Hyde et al.) ibid., 20100125420 (May 20, 2010 Hyde et al.) ibid., and 20110184247 (Jul. 28, 2011 Contant et al.) "Comprehensive Management of Human Health".

20. Other Modification of Eating Speed

This category is a catch-all for other prior art that seeks to modify eating speed using methods that are not covered by prior categories. Examples of prior art in this category include "bite traffic light" devices and sound-activating timers that signal when a person can take another bite of food. Such devices differ from earlier devices because they are not incorporated into a utensil or a wrist-worn band.

Compliance issues are a major issue with this approach. Will a person consistently use and obey a "bite traffic light" in order to time the speed at which they take bites of food? Will a person consistently tap an application on a touch screen to time the speed at which they take bites of food? Such art might be helpful for some people with strong self-discipline, but these people might have enough self-discipline to achieve the same effect by just watching a clock or just eating slowly without any automated guidance. Better methods for measuring and monitoring food consumption are needed for people without such strong self-discipline.

Examples of prior art that appear to be best classified in this category include U.S. patents: U.S. Pat. No. 5,908,301 (Jun. 1, 1999 Lutz) "Method and Device for Modifying Behavior", U.S. Pat. No. 6,473,368 (Oct. 29, 2002 Stanfield) "Consumption Controller", and U.S. Pat. No. 6,765,488 (Jul. 20, 2004 Stanfield) "Enhanced Consumption Controller"; and patent application 20120021388 (Jan. 26, 2012 Arbuckle et al.) "System and Method for Weight Management".

21. Photo Identification of Food (Bar Code or Other Packaging-Based Code)

Prior art in this category includes devices and methods for identifying food consumption based on photo identification of food using bar codes or other packaging-based codes. If consumed food has a bar code (or other packaging-based code) then it is relatively easy for a system to associate specific nutrients and/or total calories with that food.

However, there are several limitations to this approach. First, a person may eat food that is not identified by bar codes or other packaging-based codes. Food served in restaurants or in other people's homes is unlikely to be identified by such codes. Also, even in a grocery store, not all food is identified by such codes. Second, a person may not eat all of the food that is identified by such codes. Other people may eat some of the food in a given package. Also, some of the food in a given package may be thrown out. Also, depending on the longevity of the food, some food in a given package may be eaten soon after purchase and the rest may be eaten long afterwards. Accordingly, it can be problematic using such codes to make associations between food eaten by a specific person in a specific time period and the person's success in achieving weight management goals during that time period.

Examples of prior art that appear to be best classified in this category include: U.S. Pat. No. 5,819,735 (Oct. 13, 1998 Mansfield et al.) "Device and Method for Monitoring Dietary Intake of Calories And Nutrients" and U.S. Pat. No.

6,283,914 (Sep. 4, 2001 Mansfield et al.) "Device and Method for Monitoring Dietary Intake of Calories and Nutrients"; and U.S. patent applications 20030163354 (Aug. 28, 2003 Shamoun) "Device for Collecting and Analyzing Nutritional Data and Method Therefor", 20030208110 (Nov. 6, 2003 Mault et al.) "Physiological Monitoring using Wrist-Mounted Device", 20060189853 (Aug. 24, 2006 Brown) "Method and System for Improving Adherence with a Diet Program or Other Medical Regimen", 20060229504 (Oct. 12, 2006 Johnson) "Methods and Systems for Lifestyle Management", 20070059672 (Mar. 15, 2007 Shaw) "Nutrition Tracking Systems and Methods", and 20090176526 (Jul. 9, 2009 Altman) "Longitudinal Personal Health Management System Using Mobile Data Capture".

22. Photo Identification of Food (Manual Picture Taking and Identification)

Prior art in this category includes image-based devices and methods that require specific voluntary human action associated with each food consumption event (apart from the actual act of eating) in order: to take pictures of food during food consumption; and to identify the types and quantities of food consumed based on those pictures. In this category, neither picture taking nor food identification is automated. In an example, such art can include having a person aim a camera-equipped mobile electronic device toward food each time that the person eats and requiring that the person identify the type and quantity of food consumed based on the resulting pictures.

In an example, food identification by a person can occur in real-time (before, during, or immediately after a meal) using voice recognition or a menu-driven user interface. In another example, food identification by a person can occur later, long after the meal. In an example, food identification can be done by the person whose food consumption is being monitored and measured. In an example, food identification can be done by someone else.

Such image-based food logging systems are an improvement over recording food consumed with a pencil and paper. However, these devices and systems still require manual intervention to aim an imaging device toward a food source and to take at least one picture each time that the person eats something. Accordingly, they depend heavily on the person's compliance. These devices and methods can be time-consuming (having to aim the field of vision toward food), easy to circumvent (a person may simply not take pictures of some food consumed), and embarrassing to use social dining situations. This can lead to low long-term compliance.

Any approach that depends on voluntary human action each time that a person eats anything is difficult to make tamper-resistant. It is very easy for someone to "cheat" by simply not taking pictures of some consumed food items. Also, even if the person does consistently takes pictures of every meal or snack that they eat, then they may be tempted to postpone the manual task of food identification for hours or days after a meal has occurred. This can cause inaccuracy. How many chips were left in that bag in the picture? Is that a "before" or "after" picture of that gallon of ice cream? Delays in food identification can lead to imprecision in identification of the types and quantities of food consumed.

Examples of prior art that appear to be best classified in this category include U.S. patent applications: 20020047867 (Apr. 25, 2002 Mault et al.) "Image Based Diet Logging", 20020109600 (Aug. 15, 2002 Mault et al.) "Body Supported Activity and Condition Monitor", 20070030339 (Feb. 8, 2007 Findlay et al.) "Method, System and Software for Monitoring Compliance", 20090112800 (Apr. 30, 2009 Athsani) "System and Method for Visual Contextual Search", and 20090219159 (Sep. 3, 2009 Morgenstern) "Method and System for an Electronic Personal Trainer".

23. Photo Identification of Food (Manual Picture Taking and Automatic Identification)

Prior art in this category includes image-based devices and methods that require specific voluntary human actions associated with each food consumption event (apart from the actual act of eating) in order to take pictures of food during consumption. However, these devices and methods automatically identify the types and quantities of food consumed based on these pictures. In various examples, automatic identification of food types and quantities can be based on: color and texture analysis; image segmentation; image pattern recognition; volumetric analysis based on a fiduciary market or other object of known size; and/or three-dimensional modeling based on pictures from multiple perspectives. In an example, food identification can occur before or during a meal. In an example, a mobile phone application can transmit images to a remote location where automatic food identification occurs.

In some examples, food identification is an interactive process that combines automatic and manual methods of food identification. In this category, picture taking is not automated. In an example, such art can include having a person aim a camera-equipped mobile electronic device toward food to take pictures every time that the person eats food.

Such image-based consumption monitoring systems are useful, but still require specific actions by the person to aim an imaging device toward a food source and to take at least one picture of food each time that the person eats something. Accordingly, such art depends on the person's compliance. Such devices and methods can be time-consuming, easy to circumvent, and embarrassing in social dining situations. Any approach that depends on voluntary human action each time that a person eats anything is difficult to make tamper-resistant. It is very easy for someone to eat something without first taking a picture of it.

Examples of prior art that appear to be best classified in this category include: U.S. Pat. No. 6,513,532 (Feb. 4, 2003 Mault et al.) "Diet and Activity Monitoring Device", U.S. Pat. No. 8,345,930 (Jan. 1, 2013 Tamrakar et al.) "Method for Computing Food Volume in a Method for Analyzing Food", and U.S. Pat. No. 8,363,913 (Jan. 29, 2013 Boushey et al.) "Dietary Assessment System and Method"; and U.S. patent applications 20010049470 (Dec. 6, 2001 Mault et al.) "Diet and Activity Monitoring Device", 20020027164 (Mar. 7, 2002 Mault et al.) "Portable Computing Apparatus Particularly Useful in a Weight Management Program", 20030065257 (Apr. 3, 2003 Mault et al.) "Diet and Activity Monitoring Device", 20030076983 (Apr. 24, 2003 Cox) "Personal Food Analyzer", 20080267444 (Oct. 30, 2008 Simons-Nikolova) "Modifying a Person's Eating and Activity Habits", 20100111383 (May 6, 2010 Boushey et al.) "Dietary Assessment System and Method", 20100173269 (Jul. 8, 2010 Puri et al.) "Food Recognition Using Visual Analysis and Speech Recognition", 20100191155 (Jul. 29, 2010 Kim et al.) "Apparatus for Calculating Calories Balance by Classifying User's Activity", 20100332571 (Dec. 30, 2010 Healey et al.) "Device Augmented Food Identification", 20110182477 (Jul. 28, 2011 Tamrakar et al.) "Method for Computing Food Volume in a Method for Analyzing Food", 20110318717 (Dec. 29, 2011 Adamowicz) "Personalized Food Identification and Nutrition Guidance System", 20120170801 (Jul. 5, 2012 De Oliveira et al.) "System for Food Recognition Method Using Portable Devices Having Digital Cameras", 20120179665 (Jul. 12, 2012 Baarman et al.) "Health Monitoring System", 20120313776 (Dec. 13, 2012 Utter) "General Health and Wellness Management Method and Apparatus for a Wellness Application Using Data from a Data-Capable Band", 20120326873 (Dec. 27, 2012 Utter) "Activity Attainment Method and Apparatus for a Wellness Application Using Data from a Data-Capable Band", and 20130004923 (Jan. 3, 2013 Utter) "Nutrition Management Method and Apparatus for a Wellness Application Using Data from a Data-Capable Band".

24. Photo Identification of Food (Automatic Picture Taking and Identification)

Prior art in this category includes image-based devices and methods that automatically take and analyze pictures of food in order to identify the types and quantities of food consumed without the need for specific human action associated with each food consumption event (apart from the actual act of eating). In an example, automatic picture taking can occur using a camera that the person wears continually. In an example, a wearable camera can take pictures continually. In various examples, automatic identification of food types and quantities can be based on: color and texture analysis; image segmentation; image pattern recognition; volumetric analysis based on a fiduciary market or other object of known size; and/or three-dimensional modeling based on pictures from multiple perspectives. As an advantage over freestanding mobile imaging devices, wearable imaging devices offer a higher degree of automation.

Although art in this category is an innovative advance in the field, it still has at least three significant limitations that have not been fully addressed by the prior art. First, there is a trade-off between the measurement advantages of a continually-imaging wearable camera and the potential intrusion into a person's privacy. How can one achieve the measurement advantages of the wearable-imaging approach to food consumption monitoring with minimal intrusion into a person's privacy? Second, how does one address the possibility that a person can tamper with, or circumvent, such a device? Prior art in this category does not offer a tamper-resistant device.

Third, there are limitations to how accurately an image-based system can identify the composition of food. For example, many types of food, especially liquids, look similar. For example, if a beverage is not consumed in its original container, how can an image-based system know whether the beverage is high sugar vs. low sugar, or unhealthy vs. healthy? What is that sandwiched between two buns in a burger? Is it beef or turkey or a "veggie burger"? For these reasons, even though image-based prior art in this category is innovative and useful, there remains a need for better methods for automatically measuring the types and quantities of food consumption.

Examples of prior art that appear to be best classified in this category include U.S. Pat. No. 6,508,762 (Jan. 21, 2003 Karnieli) "Method for Monitoring Food Intake" and patent applications 20020022774 (Feb. 21, 2002 Karnieli) "Method for Monitoring Food Intake", and 20090012433 (Jan. 8, 2009 Fernstrom et al.) "Method, Apparatus and System for Food Intake and Physical Activity Assessment".

25. Gastric Band

With this category, we now move from devices and methods that are primarily used externally to the human body to devices and methods that are primarily implanted within the human body. Prior art in this particular category includes implantable devices that externally constrain the cross-sectional size of a member of a person's gastrointestinal tract (such as their stomach) to constrain the volume or amount of food that a person consumes. In an example, art in this category includes gastric bands that externally encircle and constrain expansion of the upper portion of a person's stomach in order to limit the volume or amount of food that passes into the person's stomach. Many of the devices in this category are adjustable in size, allowing post-operative adjustment of the external circumference of the portion of the gastrointestinal organ which the device encircles. We have separated out such devices which include sensors (and can self-adjust) in a category following this one.

Although devices in this category are innovative and have benefited many people, such devices still have limitations. First, such devices in the prior art are relatively food blind. They blindly reduce intake of all types of food. The prior art does not specify how they could be used to selectively reduce intake of unhealthy food while allowing normal consumption of healthy food. Second, such devices can irritate or harm the tissue of the gastrointestinal organ which they encircle. Third, although such devices can limit the size and flow of food entering a person's stomach, such devices do not limit the overall quantity of food that enters a person's stomach over time. For example, if a person wishes to melt an entire gallon of ice cream and then ingest it, a gastric band will not prevent this. There remains a need for better approaches for selectively modifying a person's food consumption.

Examples of prior art that appear to be best classified in this category include: U.S. Pat. No. 6,547,801 (Apr. 15, 2003 Dargent et al.) "Gastric Constriction Device", U.S. Pat. No. 6,551,235 (Apr. 22, 2003 Forsell) "Implantable Pump", U.S. Pat. No. 6,966,875 (Nov. 22, 2005 Longobardi) "Adjustable Gastric Implant", U.S. Pat. No. 7,775,967 (Aug. 17, 2010 Gertner) "Closed Loop Gastric Restriction Devices and Methods", U.S. Pat. No. 7,798,954 (Sep. 21, 2010 Birk et al.) "Hydraulic Gastric Band with Collapsible Reservoir", U.S. Pat. No. 7,909,754 (Mar. 22, 2011 Hassler et al.) "Non-Invasive Measurement of Fluid Pressure in an Adjustable Gastric Band", U.S. Pat. No. 7,972,346 (Jul. 5, 2011 Bachmann et al.) "Telemetrically Controlled Band for Regulating Functioning of a Body Organ or Duct, and Methods of Making, Implantation And Use", U.S. Pat. No. 8,034,065 (Oct. 11, 2011 Coe et al.) "Controlling Pressure in Adjustable Restriction Devices", U.S. Pat. No. 8,043,206 (Oct. 25, 2011 Birk) "Self-Regulating Gastric Band with Pressure Data Processing", U.S. Pat. No. 8,100,870 (Jan. 24, 2012 Marcotte et al.) "Adjustable Height Gastric Restriction Devices and Methods", U.S. Pat. No. 8,137,261 (Mar. 20, 2012 Kierath et al.) "Device for the Treatment of Obesity", U.S. Pat. No. 8,292,800 (Oct. 23, 2012 Stone et al.) "Implantable Pump System", U.S. Pat. No. 8,317,677 (Nov. 27, 2012 Bertolote et al.) "Mechanical Gastric Band with Cushions", and U.S. Pat. No. 8,323,180 (Dec. 4, 2012 Birk et al.) "Hydraulic Gastric Band with Collapsible Reservoir"; and U.S. patent applications 20070156013 (Jul. 5, 2007 Birk) "Self-Regulating Gastric Band with Pressure Data Processing", 20070265645 (Nov. 15, 2007 Birk et al.) "Hydraulic Gastric Band Collapsible Reservoir", 20070265646 (Nov. 15, 2007 Mccoy et al.) "Dynamically Adjustable Gastric Implants", and 20080275484 (Nov. 6, 2008 Gertner) "Per Os Placement of Extragastric Devices".

Examples of prior art that appear to be best classified in this category also include U.S. patent applications: 20090157106 (Jun. 18, 2009 Marcotte et al.) "Adjustable Height Gastric Restriction Devices and Methods", 20090171375 (Jul. 2, 2009 Coe et al.) "Controlling Pressure in Adjustable Restriction Devices", 20090204131 (Aug. 13, 2009 Ortiz et al.) "Automatically Adjusting Band System with MEMS Pump", 20090204132 (Aug. 13, 2009 Ortiz et al.) "Automatically Adjusting Band System", 20090216255 (Aug. 27, 2009 Coe et al.) "Controlling Pressure in Adjustable Restriction Devices", 20090270904 (Oct. 29, 2009 Birk et al.) "Remotely Adjustable Gastric Banding System", 20090312785 (Dec. 17, 2009 Stone et al.) "Implantable Pump System", 20100228080 (Sep. 9, 2010 Tavori et al.) "Apparatus and Methods for Corrective Guidance of Eating Behavior after Weight Loss Surgery", 20100234682 (Sep. 16, 2010 Gertner) "Closed Loop Gastric Restriction Devices and Methods", 20100324358 (Dec. 23, 2010 Birk et al.) "Hydraulic Gastric Band with Collapsible Reservoir", 20110130626 (Jun. 2, 2011 Hassler et al.) "Non-Invasive Measurement of Fluid Pressure in an Adjustable Gastric Band", 20110184229 (Jul. 28, 2011 Raven et al.) "Laparoscopic Gastric Band with Active Agents", 20110201874 (Aug. 18, 2011 Birk et al.) "Remotely Adjustable Gastric Banding System", 20110207994 (Aug. 25, 2011 Burrell et al.) "Methods and Devices for Treating Morbid Obesity Using Hydrogel", 20110207995 (Aug. 25, 2011 Snow et al.) "Inductively Powered Remotely Adjustable Gastric Banding System", 20110208216 (Aug. 25, 2011 Fobi et al.) "Gastric Bypass Band and Surgical Method", and 20110270025 (Nov. 3, 2011 Fridez et al.) "Remotely Powered Remotely Adjustable Gastric Band System".

Examples of prior art that appear to be best classified in this category also include U.S. patent applications: 20110270030 (Nov. 3, 2011 Birk et al.) "Hydraulic Gastric Band with Collapsible Reservoir", 20110275887 (Nov. 10, 2011 Birk) "Self-Regulating Gastric Band with Pressure Data Processing", 20110306824 (Dec. 15, 2011 Perron et al.) "Remotely Adjustable Gastric Banding System", 20110313240 (Dec. 22, 2011 Phillips et al.) "Flow Restrictor and Method for Automatically Controlling Pressure for a Gastric Band", 20120046674 (Feb. 23, 2012 Augarten et al.) "Power Regulated Implant", 20120059216 (Mar. 8, 2012 Perron) "Remotely Adjustable Gastric Banding System", 20120067937 (Mar. 22, 2012 Menzel) "Internal Gastric Bander for Obesity", 20120083650 (Apr. 5, 2012 Raven) "Systems and Methods for Adjusting Gastric Band Pressure", 20120088962 (Apr. 12, 2012 Franklin et al.) "Self-Adjusting Gastric Band", 20120095288 (Apr. 19, 2012 Snow et al.) "Self-Adjusting Gastric Band", 20120130273 (May 24, 2012 Hassler et al.) "Non-Invasive Measurement of Fluid Pressure in an Adjustable Gastric Band", 20120190919 (Jul. 26, 2012 Phillips et al.) "Assembly and Method for Automatically Controlling Pressure for a Gastric Band", 20120197069 (Aug. 2, 2012 Lau et al.) "Assembly and Method for Automatically Controlling Pressure for a Gastric Band", 20120215061 (Aug. 23, 2012 Fridez et al.) "Hydraulic Gastric Band with Reversible Self-Opening Mechanism", 20120215062 (Aug. 23, 2012 Coe) "Remotely Adjustable Gastric Banding Device", 20120296157 (Nov. 22, 2012 Tozzi et al.) "Medical Device Comprising an Artificial Contractile Structure", and 20120302936 (Nov. 29, 2012 Belhe et al.) "External Anchoring Configurations for Modular Gastrointestinal Prostheses".

26. Gastric Band with Sensor

Prior art in this category is similar to that of the previous category except for the addition of a sensor and the possibility of self-adjusting operation. The vast majority of sensors in this category are pressure sensors. The addition of a pressure sensor to a gastric band enables remote or automatic adjustment of the size of the constraining band in response to pressure from the external circumference of the encircled gastrointestinal organ. This can help to reduce irritation or harm of organ tissue by a constraining band, can enable post-operative refinement of therapy, and can help to reduce undesirable regurgitation. However, the other limitations that were identified with respect to gastric bands in the above category are still generally applicable to gastric bands in this category.

Examples of prior art that appear to be best classified in this category include: U.S. Pat. No. 7,775,966 (Aug. 17, 2010 Dlugos et al.) "Non-Invasive Pressure Measurement in a Fluid Adjustable Restrictive Device", U.S. Pat. No. 7,879,068 (Feb. 1, 2011 Dlugos et al.) "Feedback Sensing for a Mechanical Restrictive Device", U.S. Pat. No. 8,251,888 (Aug. 28, 2012 Roslin et al.) "Artificial Gastric Valve", and U.S. Pat. No. 8,308,630 (Nov. 13, 2012 Birk et al.) "Hydraulic Gastric Band with Collapsible Reservoir"; and U.S. patent applications 20060173238 (Aug. 3, 2006 Starkebaum) "Dynamically Controlled Gastric Occlusion Device", 20060199997 (Sep. 7, 2006 Hassler et al.) "Monitoring of a Food Intake Restriction Device", 20060235448 (Oct. 19, 2006 Roslin et al.) "Artificial Gastric Valve", 20080172072 (Jul. 17, 2008 Pool et al.) "Internal Sensors for Use with Gastric Restriction Devices", 20090192534 (Jul. 30, 2009 Ortiz et al.) "Sensor Trigger", 20100152532 (Jun. 17, 2010 Marcotte) "Gastric Band System with Esophageal Sensor", 20100274274 (Oct. 28, 2010 Roslin et al.) "Artificial Gastric Valve", 20110034760 (Feb. 10, 2011 Brynelsen et al.) "Feedback Systems and Methods to Enhance Obstructive and Other Obesity Treatments", 20110245598 (Oct. 6, 2011 Gertner) "Closed Loop Gastric Restriction Devices and Methods", and 20120108921 (May 3, 2012 Raven et al.) "Gastric Banding System Adjustment Based on a Satiety Agent Concentration Level".

27. Gastrointestinal (GI) Bypass and Tissue Plication

A gastrointestinal bypass is the creation of a new route for food to travel through a person's gastrointestinal tract that is shorter and involves less absorption of nutrients than the normal route which food travels. In some examples, the creation of a gastrointestinal bypass is primarily a surgical procedure involving reconfiguration of gastrointestinal tissue that is not primarily dependent on an implantable medical device. In other examples, the creation of a gastrointestinal bypass depends on implantation of a specific medical device. In this category, we focus primarily the role of implantable medical devices in creating a gastric bypass.

Tissue plication involves the folding and/or compartmentalization of gastrointestinal tissue in order to change the flow and/or absorption of food in a person's gastrointestinal tract. In an example, stomach walls can be folded or compartmentalized by suturing or stapling tissue to reduce the surface area of the stomach to which food is exposed. Although one could argue that GI bypass and tissue plication should be in separate categories, we have grouped them together because they both involve altering natural tissue to change the pathway and absorption of food traveling through a person's gastrointestinal tract.

Gastrointestinal (GI) bypass and tissue plication can be very effective in reducing a person's food consumption and/or absorption of nutrients from food that is consumed. However, these approaches have some significant limitations. First, some of these operations are relatively invasive, including the health risks associated with the surgery and relatively-long recovery times. Second, most of these operations are non-reversible, even if they are unsuccessful or have adverse side effects. Third, prior art in this category blindly reduces absorption of nutrients from both healthy and unhealthy food. This can result in deficiencies of key nutrients. This is particularly problematic for procedures that are non-reversible.

Examples of prior art that appear to be best classified in this category include U.S. patents: U.S. Pat. No. 6,558,400 (May 6, 2003 Deem et al.) "Obesity Treatment Tools and Methods", U.S. Pat. No. 6,572,629 (Jun. 3, 2003 Kalloo et al.) "Gastric Reduction Endoscopy", U.S. Pat. No. 7,037,343 (May 2, 2006 Imran) "Stomach Prosthesis", U.S. Pat. No. 7,037,344 (May 2, 2006 Kagan et al.) "Apparatus and Methods for Treatment of Morbid Obesity", U.S. Pat. No. 7,141,071 (Nov. 28, 2006 Imran) "Implantable Digestive Tract Organ", U.S. Pat. No. 7,288,099 (Oct. 30, 2007 Deem et al.) "Obesity Treatment Tools and Methods", U.S. Pat. No. 7,288,101 (Oct. 30, 2007 Deem et al.) "Obesity Treatment Tools and Methods", U.S. Pat. No. 7,503,922 (Mar. 17, 2009 Deem et al.) "Obesity Treatment Tools and Methods", U.S. Pat. No. 7,510,559 (Mar. 31, 2009 Deem et al.) "Obesity Treatment Tools and Methods", U.S. Pat. No. 7,601,178 (Oct. 13, 2009 Imran) "Stomach Peristalsis Device and Method", U.S. Pat. No. 7,803,195 (Sep. 28, 2010 Levy et al.) "Obesity Treatment and Device", U.S. Pat. No. 7,862,574 (Jan. 4, 2011 Deem et al.) "Obesity Treatment Tools and Methods", U.S. Pat. No. 7,909,838 (Mar. 22, 2011 Deem et al.) "Obesity Treatment Tools and Methods", U.S. Pat. No. 7,909,839 (Mar. 22, 2011 Fields) "Gastric Bypass Band and Surgical Method", U.S. Pat. No. 7,931,694 (Apr. 26, 2011 Imran) "Stomach Peristalsis Device and Method", U.S. Pat. No. 7,938,769 (May 10, 2011 Gertner) "Compressive Device for Percutaneous Treatment of Obesity", U.S. Pat. No. 7,988,617 (Aug. 2, 2011 Gertner) "Extragastric Minimally Invasive Methods and Devices to Treat Obesity", and U.S. Pat. No. 8,034,118 (Oct. 11, 2011 Imran) "Implantable Digestive Tract Organ".

Examples of prior art that appear to be best classified in this category also include U.S. patents: U.S. Pat. No. 8,070,673 (Dec. 6, 2011 Gertner et al.) "Devices and Methods to Treat A Patient", U.S. Pat. No. 8,075,577 (Dec. 13, 2011 Deem et al.) "Obesity Treatment Tools and Methods", U.S. Pat. No. 8,080,022 (Dec. 20, 2011 Deem et al.) "Obesity Treatment Tools and Methods", U.S. Pat. No. 8,080,025 (Dec. 20, 2011 Deem et al.) "Obesity Treatment Tools and Methods", U.S. Pat. No. 8,123,765 (Feb. 28, 2012 Deem et al.) "Obesity Treatment Tools and Methods", U.S. Pat. No. 8,137,366 (Mar. 20, 2012 Deem et al.) "Obesity Treatment Tools and Methods", U.S. Pat. No. 8,137,367 (Mar. 20, 2012 Deem et al.) "Obesity Treatment Tools and Methods", U.S. Pat. No. 8,147,441 (Apr. 3, 2012 Gannoe et al.) "Method and Device for Use in Endoscopic Organ Procedures", U.S. Pat. No. 8,187,289 (May 29, 2012 Tacchino et al.) "Device and Method for the Therapy of Obesity", U.S. Pat. No. 8,197,498 (Jun. 12, 2012 Coleman et al.) "Gastric Bypass Devices and Procedures", U.S. Pat. No. 8,206,456 (Jun. 26, 2012 Stack et al.) "Restrictive and/or Obstructive Implant System for Inducing Weight Loss", U.S. Pat. No. 8,211,128 (Jul. 3, 2012 Facundus et al.) "Multifunction Gastric Bypass Apparatus and Method", U.S. Pat. No. 8,252,009 (Aug. 28, 2012 Weller et al.) "Devices and Methods for Placement of Partitions within a Hollow Body Organ", and U.S. Pat. No. 8,287,554 (Oct. 16, 2012 Cerier et al.) "Method and Devices for Tissue Reconfiguration".

Examples of prior art that appear to be best classified in this category also include U.S. Patent applications: 20040122452 (Jun. 24, 2004 Deem et al.) "Obesity Treatment Tools and Methods", 20040122453 (Jun. 24, 2004 Deem et al.) "Obesity Treatment Tools and Methods", 20070093910 (Apr. 26, 2007 Imran) "Implantable Digestive Tract Organ", 20070250083 (Oct. 25, 2007 Deem et al.) "Obesity Treatment Tools and Methods", 20100004755 (Jan. 7, 2010 Imran) "Stomach Peristalsis Device and Method", 20100145378 (Jun. 10, 2010 Gertner) "Percutaneous Gastroplasty", 20100204723 (Aug. 12, 2010 Gertner) "Obesity Systems Placed Between the Abdominal Wall and Stomach", 20110009887 (Jan. 13, 2011 Harris et al.) "Methods for Reducing Gastric Volume", 20110009980 (Jan. 13, 2011 Levy et al.) "Obesity Treatment and Device", 20110098725 (Apr. 28, 2011 Cox et al.) "Devices and Methods for Endolumenal Weight Loss Treatments", 20110152899 (Jun. 23, 2011 Deem et al.) "Obesity Treatment Tools and Methods", 20110152899 (Jun. 23, 2011 Deem et al.) "Obesity Treatment Tools and Methods", 20110196504 (Aug. 11, 2011 Imran) "Stomach Peristalsis Device and Method", and 20110208209 (Aug. 25, 2011 Ewers et al.) "Devices and Methods for Laparoscopic Gastric Tissue Reconfiguration".

Examples of prior art that appear to be best classified in this category also include U.S. Patent applications: 20110213385 (Sep. 1, 2011 Ewers et al.) "Delivery Systems and Methods for Gastric Reduction", 20110295055 (Dec. 1, 2011 Albrecht et al.) "Methods and Devices for the Rerouting of Chyme to Induct Intestinal Brake", 20120010459 (Jan. 12, 2012 Lau et al.) "Assembly and Method for Automatically Controlling Pressure for a Gastric Band", 20120016392 (Jan. 19, 2012 Silverman et al.) "Method for Treating Morbid Obesity", 20120022319 (Jan. 26, 2012 Muller) "Systems and Methods for Reducing Gastric Volume", 20120071900 (Mar. 22, 2012 Vahid et al.) "Methods for Reduction of Gastric Lumen", 20120101594 (Apr. 26, 2012 Fogel) "Endoscopic Implantable Device and Method for the Apposition of the Stomach Walls for Reducing the Stomach Internal Volume in a Weight Loss Surgery . . . ", 20120116536 (May 10, 2012 Imran) "Implantable Digestive Tract Organ", 20120160893 (Jun. 28, 2012 Harris et al.) "Methods and Devices for Reducing Gastric Volume", 20120165843 (Jun. 28, 2012 Gannoe et al.) "Method and Device for use in Endoscopic Organ Procedures", 20120165845 (Jun. 28, 2012 Harris et al.) "Methods and Devices for Reducing Gastric Volume", 20120209400 (Aug. 16, 2012 Schurr) "Medical Implant", 20120209400 (Aug. 16, 2012 Schurr) "Medical Implant", 20120265224 (Oct. 18, 2012 Coleman et al.) "Gastric Bypass Devices and Procedures", 20120296348 (Nov. 22, 2012 Saadat et al.) "Apparatus for Manipulating and Securing Tissue", and 20120296354 (Nov. 22, 2012 Hsu et al.) "Methods and Devices for Treating Obesity and GERD by Intussuscepting a Portion of Stomach Tissue".

28. Pumping Food Out of the Stomach Through an Intra-Abdominal Pathway

This novel and unusual category of prior art comprises an implantable intra-abdominal pathway and an accompanying pumping mechanism that allows a person to pump food out of their stomach. Using such a device, even if a person is unable to control what food they eat, the person can still avoid having the body absorb nutrients from the consumed food. This is a novel approach to the problem of excessive caloric intake, but there remain many unknowns with respect to its use. How will people view discharging partially-digested food through a permanent implantable intra-abdominal pathway as a method for losing weight? Will the connections between the intra-abdominal pathway, the person's actively-moving stomach, and the person's skin surface remain durable, secure, and sanitary?

Examples of prior art that appear to be best classified in this category include: U.S. Pat. No. 7,648,479 (Jan. 19, 2010

Solovay et al.) "Systems and Methods for Removing Ingested Material from a Stomach", U.S. Pat. No. 7,740,624 (Jun. 22, 2010 Klein et al.) "Method for Treating Obesity by Extracting Food", U.S. Pat. No. 7,815,629 (Oct. 19, 2010 Klein et al.) "Apparatus for Treating Obesity by Extracting Food", U.S. Pat. No. 8,002,758 (Aug. 23, 2011 Kamen et al.) "Systems and Methods for Removing Ingested Material from a Stomach", and U.S. Pat. No. 8,062,285 (Nov. 22, 2011 Langloss et al.) "Systems and Methods for Removing Ingested Material from a Stomach"; and U.S. patent applications U.S. Pat. No. 8,282,623 (Oct. 9, 2012 Klein et al.) "Method for Treating Obesity by Extracting Food", 20050277900 (Dec. 15, 2005 Klein et al.) "Apparatus for Treating Obesity by Extracting Food", 20080033345 (Feb. 7, 2008 Langloss et al.) "Systems and Methods for Removing Ingested Material from a Stomach", 20080033364 (Feb. 7, 2008 Kamen et al.) "Systems and Methods for Removing Ingested Material from a Stomach", 20080033365 (Feb. 7, 2008 Solovay et al.) "Systems and Methods for Removing Ingested Material from a Stomach", 20080039809 (Feb. 14, 2008 Kamen et al.) "Systems and Methods for Removing Ingested Material from a Stomach", 20080091146 (Apr. 17, 2008 Solovay et al.) "Shunt Apparatus for Treating Obesity by Extracting Food", 20100106130 (Apr. 29, 2010 Solovay et al.) "Method for Treating Obesity by Extracting Food", 20100106131 (Apr. 29, 2010 Klein et al.) "Method for Treating Obesity by Extracting Food", 20100241090 (Sep. 23, 2010 Klein et al.) "Apparatus for Treating Obesity by Extracting Food", 20110178480 (Jul. 21, 2011 Solovay et al.) "Shunt Apparatus for Treating Obesity by Extracting Food", and 20110190719 (Aug. 4, 2011 Kamen et al.) "Systems And Methods for Removing Ingested Material from a Stomach".

29. Gastric Tube

Prior art in this category includes insertion of a tube down into a person's gastrointestinal tract. Devices in this category, including gastric tubes, are generally used for feeding purposes rather than modification of food consumption or absorption. Nonetheless, we have included them here in this categorization scheme because tubes inserted into the gastrointestinal tract can be relevant to some approaches to modification of food consumption.

Examples of prior art that appear to be best classified in this category include: U.S. Pat. No. 7,794,425 (Sep. 14, 2010 Gobel) "Gastro-Esophageal Reflux Control System and Pump" and U.S. Pat. No. 7,967,780 (Jun. 28, 2011 Goebel) "Gastro-Esophageal Reflux Control System and Pump"; and U.S. patent applications 20080154191 (Jun. 26, 2008 Gobel) "Gastro-Esophageal Reflux Control System and Pump", 20090062725 (Mar. 5, 2009 Goebel) "Gastro-Esophageal Reflux Control System and Pump", 20100204669 (Aug. 12, 2010 Knight) "Enteral Feeding Safety Reservoir and System", 20100217194 (Aug. 26, 2010 Pang) "Device for Tube Feeding", 20100298812 (Nov. 25, 2010 Wolkenstorfer) "Catheter System", and 20110082442 (Apr. 7, 2011 Solovay et al.) "Externally Reinforced Percutaneous Gastrostomy Tube with Customizable Smooth Tube Length".

30. Enzyme Flow Modification

Prior art in this category includes diversion of enzymes that play a role in the digestion and absorption of food in the gastrointestinal tract. In various examples, the flow of enzymes into the gastrointestinal tract can be increased, decreased, or diverted. For example, enzymes can be diverted so that they are discharged into the gastrointestinal tract at a lower location, thereby reducing the digestion and absorption of food that passes through the gastrointestinal tract.

Examples of prior art that appear to be best classified in this category include: U.S. Pat. No. 7,833,279 (Nov. 16, 2010 Knudson et al.) "Pancreatic Exocrine Secretion Diversion Apparatus and Method"; and U.S. patent applications 20060106332 (May 18, 2006 Knudson et al.) "Pancreatic Exocrine Secretion Diversion Apparatus and Method", 20110021968 (Jan. 27, 2011 Knudson et al.) "Pancreatic Exocrine Secretion Diversion Apparatus and Method", 20120116285 (May 10, 2012 Duggirala) "Devices for Treating Obesity and Methods of Using Those Devices", and 20120172782 (Jul. 5, 2012 Thompson) "Methods for Biliary Diversion".

31. Gastrointestinal (GI) Volume or Pressure or Flow Modification

This relatively-broad category of prior art includes various devices that modify the interior volume of a gastrointestinal organ (such as the stomach), interior wall pressure of a gastrointestinal organ (such as the stomach), and/or food flow through a valve in a gastro-intestinal organ (such as the pyloric valve in the stomach). In various examples, art in this category can: occupy some of the interior volume of a gastrointestinal organ (such as an expandable gastric balloon in the stomach); apply pressure to the interior walls of a gastrointestinal organ (such as an expandable stomach stent); or mechanically modify the operation of a gastrointestinal valve (such as the operation of the pyloric valve within the stomach).

In an example, reducing the available space for food to occupy within the stomach can reduce the amount of food consumed and/or cause an earlier sensation of fullness. In an example, applying pressure to the interior walls of the stomach can cause an earlier sensation of fullness and reduce the amount of food consumed. In an example, reducing the outflow of food from the stomach by modifying the operation of the pyloric valve can lead to an earlier sensation of fullness and reduce food consumed.

However, there can be limitations to such devices. For example, the stomach can stretch even further when a balloon is implanted inside it or a stent is expanded within it, thwarting efforts to cause an earlier sensation of fullness or reduce food consumption. Also, even if a temporary balloon or stent is effective while implanted, that effect can be lost (or reversed) when the temporary balloon or stent is removed. In a worst case scenario, such a device can make the person worse off. After removal of a balloon or stent, a stretched stomach can accommodate even more food than normal, causing the person to eat more than ever in the long run.

Examples of prior art that appear to be best classified in this category include U.S. patents: U.S. Pat. No. 4,133,315 (Jan. 9, 1979 Berman et al.) "Method and Apparatus for Reducing Obesity", U.S. Pat. No. 4,416,267 (Nov. 22, 1983 Garren et al.) "Method and Apparatus for Treating Obesity", U.S. Pat. No. 4,592,339 (Jun. 3, 1986 Kuzmak et al.) "Gastric Banding Device", U.S. Pat. No. 4,694,827 (Sep. 22, 1987 Weiner et al.) "Inflatable Gastric Device for Treating Obesity and Method of Using the Same", U.S. Pat. No. 5,074,868 (Dec. 24, 1991 Kuzmak) "Reversible Stoma-Adjustable Gastric Band", U.S. Pat. No. 5,226,429 (Jul. 13, 1993 Kuzmak) "Laparoscopic Gastric Band and Method", U.S. Pat. No. 5,234,454 (Aug. 10, 1993 Bangs) "Percutaneous Intragastric Balloon Catheter and Method for Controlling Body Weight Therewith", U.S. Pat. No. 5,259,399 (Nov. 9, 1993 Brown) "Device and Method of Causing Weight Loss Using Removable Variable Volume Intragastric Bladder", U.S. Pat. No. 5,449,368 (Sep. 12, 1995 Kuzmak) "Laparoscopic Adjustable Gastric Banding Device and Method for Implantation and Removal Thereof", U.S. Pat. No. 5,601,604 (Feb. 11, 1997 Vincent) "Universal Gastric Band", U.S. Pat. No. 5,868,141 (Feb. 9, 1999 Ellias) "Endoscopic Stomach Insert for Treating Obesity and Method for Use", U.S. Pat. No. 5,993,473 (Nov. 30, 1999 Chan et al.) "Expandable Body Device for the Gastric Cavity and Method", U.S. Pat. No. 6,067,991 (May 30, 2000 Forsell) "Mechanical Food Intake Restriction Device", U.S. Pat. No. 6,454,785 (Sep. 24, 2002 De Hoyos Garza) "Percutaneous Intragastric Balloon Catheter for the Treatment Of Obesity", U.S. Pat. No. 6,579,301 (Jun. 17, 2003 Bales et al.) "Intragastric Balloon Device Adapted to be Repeatedly Varied in Volume Without External Assistance", U.S. Pat. No. 6,675,809 (Jan. 13, 2004 Stack et al.) "Satiation Devices and Methods", U.S. Pat. No. 6,733,512 (May 11, 2004 Mcghan) "Self-Deflating Intragastric Balloon", U.S. Pat. No. 6,981,980 (Jan. 3, 2006 Sampson et al.) "Self-Inflating Intragastric Volume-Occupying Device", U.S. Pat. No. 7,033,373 (Apr. 25, 2006 DeLaTorre et al.) "Method and Device for Use in Minimally Invasive Placement of Space-Occupying Intragastric Devices", U.S. Pat. No. 7,066,945 (Jun. 27, 2006 Hashiba et al.) "Intragastric Device for Treating Obesity", and U.S. Pat. No. 7,112,186 (Sep. 26, 2006 Shah) "Gastro-Occlusive Device".

Examples of prior art that appear to be best classified in this category also include U.S. patents: U.S. Pat. No. 7,354,454 (Apr. 8, 2008 Stack et al.) "Satiation Devices and Methods", U.S. Pat. No. 7,470,251 (Dec. 30, 2008 Shah) "Gastro-Occlusive Device", U.S. Pat. No. 7,682,306 (Mar. 23, 2010 Shah) "Therapeutic Intervention Systems Employing Implantable Balloon Devices", U.S. Pat. No. 7,699,863 (Apr. 20, 2010 Marco et al.) "Bioerodible Self-Deployable Intragastric Implants", U.S. Pat. No. 7,717,843 (May 18, 2010 Balbierz et al.) "Restrictive and/or Obstructive Implant for Inducing Weight Loss", U.S. Pat. No. 7,758,493 (Jul. 20, 2010 Gingras) "Gastric Constriction Device", U.S. Pat. No. 7,771,382 (Aug. 10, 2010 Levine et al.) "Resistive Anti-Obesity Devices", U.S. Pat. No. 7,785,291 (Aug. 31, 2010 Marco et al.) "Bioerodible Self-Deployable Intragastric Implants", U.S. Pat. No. 7,841,978 (Nov. 30, 2010 Gertner) "Methods and Devices for to Treatment of Obesity", U.S. Pat. No. 7,963,907 (Jun. 21, 2011 Gertner) "Closed Loop Gastric Restriction Devices and Methods", U.S. Pat. No. 8,001,974 (Aug. 23, 2011 Makower et al.) "Devices and Methods for Treatment of Obesity", U.S. Pat. No. 8,016,744 (Sep. 13, 2011 Dlugos et al.) "External Pressure-Based Gastric Band Adjustment System and Method", U.S. Pat. No. 8,016,745 (Sep. 13, 2011 Hassler et al.) "Monitoring of a Food Intake Restriction Device", U.S. Pat. No. 8,029,455 (Oct. 4, 2011 Stack et al.) "Satiation Pouches and Methods of Use", U.S. Pat. No. 8,048,169 (Nov. 1, 2011 Burnett et al.) "Pyloric Valve Obstructing Devices and Methods", U.S. Pat. No. 8,066,780 (Nov. 29, 2011 Chen et al.) "Methods for Gastric Volume Control", U.S. Pat. No. 8,083,756 (Dec. 27, 2011 Gannoe et al.) "Methods and Devices for Maintaining a Space Occupying Device in a Relatively Fixed Location Within a Stomach", U.S. Pat. No. 8,083,757 (Dec. 27, 2011 Gannoe et al.) "Methods and Devices for Maintaining a Space Occupying Device in a Relatively Fixed Location Within a Stomach", U.S. Pat. No. 8,142,469 (Mar. 27, 2012 Sosnowski et al.) "Gastric Space Filler Device, Delivery System, and Related Methods", U.S. Pat. No. 8,142,513 (Mar. 27, 2012 Shalon et al.) "Devices and Methods for Altering Eating Behavior", U.S. Pat. No. 8,187,297 (May 29, 2012 Makower et al.) "Devices and Methods for Treatment of Obesity", U.S. Pat. No. 8,192,455 (Jun. 5, 2012 Brazzini et al.) "Compressive Device for Percutaneous Treatment of Obesity", U.S. Pat. No. 8,202,291 (Jun. 19, 2012 Brister et al.) "Intragastric Device", U.S. Pat. No. 8,226,593 (Jul. 24, 2012 Graham et al.) "Pyloric Valve", U.S. Pat. No. 8,236,023 (Aug. 7, 2012 Birk et al.) "Apparatus and Method for Volume Adjustment of Intragastric Balloons", U.S. Pat. No. 8,241,202 (Aug. 14, 2012 Balbierz et al.) "Restrictive and/or Obstructive Implant for Inducing Weight Loss", U.S. Pat. No. 8,267,888 (Sep. 18, 2012 Marco et al.) "Bioerodible Self-Deployable Intragastric Implants", U.S. Pat. No. 8,282,666 (Oct. 9, 2012 Birk) "Pressure Sensing Intragastric Balloon", U.S. Pat. No. 8,292,911 (Oct. 23, 2012 Brister et al.) "Intragastric Device", U.S. Pat. No. 8,292,911 (Oct. 23, 2012 Brister et al.) "Intragastric Device", U.S. Pat. No. 8,295,932 (Oct. 23, 2012 Bitton et al.) "Ingestible Capsule for Appetite Regulation", and U.S. Pat. No. 8,337,566 (Dec. 25, 2012 Stack et al.) "Method and Apparatus for Modifying the Exit Orifice of a Satiation Pouch".

Examples of prior art that appear to be best classified in this category also include U.S. patent applications: 20010037127 (Nov. 1, 2001 De Hoyos Garza) "Percutaneous Intragastric Balloon Catheter for the Treatment of Obesity", 20060252983 (Nov. 9, 2006 Lembo et al.) "Dynamically Adjustable Gastric Implants and Methods of Treating Obesity Using Dynamically Adjustable Gastric Implants", 20060264699 (Nov. 23, 2006 Gertner) "Extragastric Minimally Invasive Methods and Devices to Treat Obesity", 20070149994 (Jun. 28, 2007 Sosnowski et al.) "Intragastric Space Filler and Methods of Manufacture", 20070207199 (Sep. 6, 2007 Sogin) "Appetite Suppression Device", 20070276293 (Nov. 29, 2007 Gertner) "Closed Loop Gastric Restriction Devices and Methods", 20070293885 (Dec. 20, 2007 Binmoeller) "Methods and Devices to Curb Appetite and/or to Reduce Food Intake", 20080051824 (Feb. 28, 2008 Gertner) "Methods and Devices for to Treatment of Obesity", 20080065168 (Mar. 13, 2008 Bitton et al.) "Ingestible Capsule for Appetite Regulation", 20080147002 (Jun. 19, 2008 Gertner) "Obesity Treatment Systems", 20080161717 (Jul. 3, 2008 Gertner) "Obesity Treatment Systems", 20080188766 (Aug. 7, 2008 Gertner) "Obesity Treatment Systems", 20080208240 (Aug. 28, 2008 Paz) "Implantable Device for Obesity Prevention", 20080319471 (Dec. 25, 2008 Sosnowski et al.) "Gastric Space Filler Device, Delivery System, and Related Methods", 20090131968 (May 21, 2009 Birk) "Pressure Sensing Intragastric Balloon", 20090192535 (Jul. 30, 2009 Kasic) "Swallowable Self-Expanding Gastric Space Occupying Device", 20090247992 (Oct. 1, 2009 Shalon et al.) "Devices and Methods for Altering Eating Behavior", 20090259246 (Oct. 15, 2009 Eskaros et al.) "Intragastric Volume-Occupying Device", 20090275973 (Nov. 5, 2009 Chen et al.) "Devices and Systems for Gastric Volume Control", 20090306462 (Dec. 10, 2009 Lechner) "System for Controlling a Controllable Stomach Band", 20100100117 (Apr. 22, 2010 Brister et al.) "Intragastric Device", 20100114125 (May 6, 2010 Albrecht et al.) "Method of Remotely Adjusting a Satiation and Satiety-Inducing Implanted Device", 20100114125 (May 6, 2010 Albrecht et al.) "Method of Remotely Adjusting a Satiation and Satiety-Inducing Implanted Device", 20100130998 (May 27, 2010 Alverdy) "Balloon System and Methods for Treating Obesity", 20100137897 (Jun. 3, 2010 Brister et al.) "Intragastric Device", 20100152764 (Jun. 17, 2010 Merkle) "Device for Treating Obesity", 20100286660 (Nov. 11, 2010 Gross)

"Gastroretentive Duodenal Pill", and 20100298632 (Nov. 25, 2010 Levine et al.) "Resistive Anti-Obesity Devices".

Examples of prior art that appear to be best classified in this category also include U.S. patent applications: 20100312049 (Dec. 9, 2010 Forsell) "Apparatus for Treating Obesity", 20100312050 (Dec. 9, 2010 Forsell) "Method and Instrument for Treating Obesity", 20100312147 (Dec. 9, 2010 Gertner) "Obesity Treatment Systems", 20100324361 (Dec. 23, 2010 Forsell) "Apparatus for Treating Obesity", 20100331616 (Dec. 30, 2010 Forsell) "Method and Instrument for Treating Obesity", 20100331617 (Dec. 30, 2010 Forsell) "Device, System and Method for Treating Obesity", 20100332000 (Dec. 30, 2010 Forsell) "Device for Treating Obesity", 20110009895 (Jan. 13, 2011 Gertner) "Methods and Devices to Treat Obesity", 20110009896 (Jan. 13, 2011 Forsell) "Apparatus for Treating Obesity", 20110015665 (Jan. 20, 2011 Marco et al.) "Bioerodible Self-Deployable Intragastric Implants", 20110015666 (Jan. 20, 2011 Marco et al.) "Bioerodible Self-Deployable Intragastric Implants", 20110022072 (Jan. 27, 2011 Marco et al.) "Bioerodible Self-Deployable Intragastric Implants", 20110040318 (Feb. 17, 2011 Marco et al.) "Bioerodible Self-Deployable Intragastric Implants", 20110060308 (Mar. 10, 2011 Stokes et al.) "Methods and Implants for Inducing Satiety in the Treatment of Obesity", 20110060358 (Mar. 10, 2011 Stokes et al.) "Methods and Implants for Inducing Satiety in the Treatment of Obesity", 20110092998 (Apr. 21, 2011 Hirszowicz et al.) "Balloon Hydraulic and Gaseous Expansion System", 20110106129 (May 5, 2011 Gertner) "Methods and Devices to Treat Obesity", 20110172693 (Jul. 14, 2011 Forsell) "Apparatus and Method for Treating Obesity", 20110178544 (Jul. 21, 2011 Sosnowski et al.) "Gastric Space Filler Delivery System and Related Methods", 20110196411 (Aug. 11, 2011 Forsell) "Apparatus for Treating Obesity", 20110213448 (Sep. 1, 2011 Kim) "Apparatus and Methods for Minimally Invasive Obesity Treatment", 20110213469 (Sep. 1, 2011 Chin et al.) "Systems and Methods for Bariatric Therapy", 20110224714 (Sep. 15, 2011 Gertner) "Methods and Devices for the Surgical Creation of Satiety and Biofeedback Pathways", 20110269711 (Nov. 3, 2011 Adden et al.) "Methods and Compositions for Inducing Satiety", and 20110295056 (Dec. 1, 2011 Aldridge et al.) "Systems and Methods for Gastric Volume Regulation".

Examples of prior art that appear to be best classified in this category also include U.S. patent applications: 20110295057 (Dec. 1, 2011 Aldridge et al.) "Systems and Methods for Gastric Volume Regulation", 20110307075 (Dec. 15, 2011 Sharma) "Intragastric Device for Treating Obesity", 20110319924 (Dec. 29, 2011 Cole et al.) "Gastric Space Occupier Systems and Methods of Use", 20120004590 (Jan. 5, 2012 Stack et al.) "Satiation Pouches and Methods of Use", 20120022322 (Jan. 26, 2012 Pasricha) "Methods and Devices for Treating Obesity", 20120029550 (Feb. 2, 2012 Forsell) "Obesity Treatment", 20120041463 (Feb. 16, 2012 Forsell) "Obesity Treatment", 20120053613 (Mar. 1, 2012 Weitzner et al.) "Gastric Filler Devices for Obesity Therapy", 20120089168 (Apr. 12, 2012 Baker et al.) "Bariatric Device and Method", 20120089170 (Apr. 12, 2012 Dominguez) "Intragastric Balloon Geometries", 20120089172 (Apr. 12, 2012 Babkes et al.) "Re-Shaping Intragastric Implants", 20120095384 (Apr. 19, 2012 Babkes et al.) "Stomach-Spanning Gastric Implants", 20120095492 (Apr. 19, 2012 Babkes et al.) "Variable Size Intragastric Implant Devices", 20120095494 (Apr. 19, 2012 Dominguez et al.) "Intragastric Implants with Collapsible Frames", 20120095495 (Apr. 19, 2012 Babkes et al.) "Space-Filling Intragastric Implants with Fluid Flow", 20120095496 (Apr. 19, 2012 Dominguez et al.) "Reactive Intragastric Implant Devices", 20120095497 (Apr. 19, 2012 Babkes et al.) "Non-Inflatable Gastric Implants and Systems", 20120095499 (Apr. 19, 2012 Babkes et al.) "Upper Stomach Gastric Implants", 20120123465 (May 17, 2012 Nihalani) "Method and Apparatus for Treating Obesity and Controlling Weight Gain using Self-Expanding Intragastric Devices", 20120150316 (Jun. 14, 2012 Carvalho) "Esophageal Flow Controller", 20120165855 (Jun. 28, 2012 Shalon et al.) "Devices and Methods for Altering Eating Behavior", 20120165855 (Jun. 28, 2012 Shalon et al.) "Devices and Methods for Altering Eating Behavior", 20120191123 (Jul. 26, 2012 Brister et al.) "Intragastric Device", and 20120191124 (Jul. 26, 2012 Brister et al.) "Intragastric Device".

Examples of prior art that appear to be best classified in this category also include U.S. patent applications: 20120191125 (Jul. 26, 2012 Babkes et al.) "Intragastric Implants with Multiple Fluid Chambers", 20120191126 (Jul. 26, 2012 Pecor et al.) "Inflation and Deflation Mechanisms for Inflatable Medical Devices", 20120203061 (Aug. 9, 2012 Birk) "Bariatric Device and Method for Weight Loss", 20120215249 (Aug. 23, 2012 Brazzini et al.) "Compressive Device for Percutaneous Treatment of Obesity", 20120221037 (Aug. 30, 2012 Birk et al.) "Bariatric Device and Method for Weight Loss", 20120232576 (Sep. 13, 2012 Brister et al.) "Intragastric Device", 20120232577 (Sep. 13, 2012 Birk et al.) "Bariatric Device and Method for Weight Loss", 20120253378 (Oct. 4, 2012 Makower et al.) "Devices and Methods for Treatment of Obesity", 20120259427 (Oct. 11, 2012 Graham et al.) "Pyloric Valve", 20120265030 (Oct. 18, 2012 Li) "Devices Systems Kits and Methods for Treatment of Obesity", 20120265234 (Oct. 18, 2012 Brister et al.) "Intragastric Device", 20120283766 (Nov. 8, 2012 Makower et al.) "Devices and Methods for Treatment of Obesity", 20120289992 (Nov. 15, 2012 Quijano et al.) "Intragastric Balloon System and Therapeutic Processes and Products", and 20120316387 (Dec. 13, 2012 Volker) "Adjustable Gastric Wrap (AGW)".

32. Gastrointestinal (GI) Volume or Pressure or Flow Modification (with Drug)

Prior art in this category is similar to that in the previous category, except that it also includes delivery of a pharmaceutical agent. In various examples, this category can include drug-eluting gastric balloons, gastric balloons with an integral drug pump, and drug-eluting gastric stents. Although drug delivery can provide another therapeutic modality for these devices, the addition of drug delivery does not correct most of the potential limitations of devices that were discussed in the previous category. Accordingly, most of these limitations still apply to devices in this present category.

Examples of prior art that appear to be best classified in this category include: U.S. Pat. No. 6,627,206 (Sep. 30, 2003 Lloyd) "Method and Apparatus for Treating Obesity and for Delivering Time-Released Medicaments", U.S. Pat. No. 7,121,283 (Oct. 17, 2006 Stack et al.) "Satiation Devices and Methods", U.S. Pat. No. 7,152,607 (Dec. 26, 2006 Stack et al.) "Satiation Devices and Methods", U.S. Pat. No. 7,833,280 (Nov. 16, 2010 Stack et al.) "Satiation Devices and Methods", U.S. Pat. No. 7,854,745 (Dec. 21, 2010 Brister et al.) "Intragastric Device", U.S. Pat. No. 8,070,768 (Dec. 6, 2011 Kim et al.) "Devices and Methods for Treatment of Obesity", U.S. Pat. No. 8,162,969 (Apr. 24, 2012 Brister et al.) "Intragastric Device", U.S. Pat. No. 8,177,853 (May 15, 2012 Stack et al.) "Satiation Devices and Methods", and U.S. Pat. No. 8,226,602 (Jul. 24, 2012 Quijana et al.) "Intragastric Balloon System and Therapeutic Processes and Products"; and U.S. patent applications 20030021822 (Jan. 30, 2003 Lloyd) "Method and Apparatus for Treating Obesity and for Delivering Time-Released Medicaments", 20040172142 (Sep. 2, 2004 Stack et al.) "Satiation Devices and Methods", 20070265598 (Nov. 15, 2007 Karasik) "Device and Method for Treating Weight Disorders", 20080243071 (Oct. 2, 2008 Quijano et al.) "Intragastric Balloon System and Therapeutic Processes and Products", 20100100116 (Apr. 22, 2010 Brister et al.) "Intragastric Volume-Occupying Device and Method for Fabricating Same", 20100114150 (May 6, 2010 Magal) "Duodenal Stimulation Devices and Methods for the Treatment of Conditions Relating to Eating Disorders", 20120016287 (Jan. 19, 2012 Stack et al.) "Satiation Devices and Methods", 20120022430 (Jan. 26, 2012 Stack et al.) "Satiation Devices and Methods", 20120245553 (Sep. 27, 2012 Raven et al.) "Intragastric Volume Occupying Device with Active Agents", and 20120271217 (Oct. 25, 2012 Stack et al.) "Satiation Devices and Methods".

33. Gastrointestinal (GI) Sleeve or Liner

Prior art in this category includes gastrointestinal sleeves, gastrointestinal liners, and other flexible tubular devices that are implanted within a person's gastrointestinal tract to reduce absorption of nutrients from food by reducing contact between food and the walls of the gastrointestinal tract. Gastric sleeves are common examples of devices in this category. As long as devices in this category can be securely and safely fastened to their proper location within the gastrointestinal tract so that they do not migrate or cause blockages, these devices have potential to be a useful addition to the available approaches to limiting absorption of nutrients from food. Most are less invasive than gastric bypass operations and can be removed if they do not work well.

However, gastrointestinal sleeves and liners in the prior art are food blind. They are not able to selectively reduce absorption of nutrients from unhealthy food and allow normal absorption of nutrients from healthy food. Also, they are implanted and thus do require an operation. In this respect, they are more invasive than purely-external approaches to monitoring and modifying food consumption.

Examples of prior art that appear to be best classified in this category include U.S. patents: U.S. Pat. No. 4,641,653 (Feb. 10, 1987 Rockey) "Medical Sleeve", U.S. Pat. No. 7,220,284 (May 22, 2007 Kagan et al.) "Gastrointestinal Sleeve Device and Methods for Treatment of Morbid Obesity", U.S. Pat. No. 7,695,446 (Apr. 13, 2010 Levine et al.) "Methods of Treatment Using a Bariatric Sleeve", U.S. Pat. No. 7,753,870 (Jul. 13, 2010 Demarais et al.) "Systems and Methods for Treating Obesity", U.S. Pat. No. 7,794,447 (Sep. 14, 2010 Dann et al.) "Gastrointestinal Sleeve Device and Methods for Treatment of Morbid Obesity", U.S. Pat. No. 7,837,643 (Nov. 23, 2010 Levine et al.) "Methods and Devices for Placing a Gastrointestinal Sleeve", U.S. Pat. No. 7,837,669 (Nov. 23, 2010 Dann et al.) "Devices and Methods for Endolumenal Gastrointestinal Bypass", U.S. Pat. No. 7,846,138 (Dec. 7, 2010 Dann et al.) "Cuff and Sleeve System for Gastrointestinal Bypass", U.S. Pat. No. 7,935,073 (May 3, 2011 Levine et al.) "Methods of Treatment Using a Bariatric Sleeve", U.S. Pat. No. 7,981,162 (Jul. 19, 2011 Stack et al.) "Satiation Devices and Methods", U.S. Pat. No. 8,012,140 (Sep. 6, 2011 Kagan et al.) "Methods of Transmural Attachment in the Gastrointestinal System", U.S. Pat. No. 8,057,420 (Nov. 15, 2011 Meade et al.) "Gastrointestinal Implant with Drawstring", U.S. Pat. No. 8,070,743 (Dec. 6, 2011 Kagan et al.) "Devices and Methods for Attaching an Endolumenal Gastrointestinal Implant", U.S. Pat. No. 8,109,895 (Feb. 7, 2012 Williams et al.) "Intestinal Sleeves and Associated Deployment Systems and Methods", U.S. Pat. No. 8,137,301 (Mar. 20, 2012 Levine et al.) "Bariatric Sleeve", U.S. Pat. No. 8,162,871 (Apr. 24, 2012 Levine et al.) "Bariatric Sleeve", U.S. Pat. No. 8,182,459 (May 22, 2012 Dann et al.) "Devices and Methods for Endolumenal Gastrointestinal Bypass", U.S. Pat. No. 8,211,186 (Jul. 3, 2012 Belhe et al.) "Modular Gastrointestinal Prostheses", U.S. Pat. No. 8,216,158 (Jul. 10, 2012 Johnson) "Implantation of a Medical Device Within a Lumen", U.S. Pat. No. 8,282,598 (Oct. 9, 2012 Belhe et al.) "External Anchoring Configurations for Modular Gastrointestinal Prostheses", and U.S. Pat. No. 8,303,669 (Nov. 6, 2012 Meade et al.) "Methods and Apparatus for Anchoring within the Gastrointestinal Tract".

Examples of prior art that appear to be best classified in this category also include U.S. patent applications: 20090093767 (Apr. 9, 2009 Kelleher) "Devices and Methods for Endolumenal Therapy", 20090240340 (Sep. 24, 2009 Levine et al.) "Bariatric Sleeve", 20090248171 (Oct. 1, 2009 Levine et al.) "Bariatric Sleeve", 20100256775 (Oct. 7, 2010 Belhe et al.) "Modular Gastrointestinal Prostheses", 20100298631 (Nov. 25, 2010 Stack et al.) "Satiation Devices and Methods", 20110009690 (Jan. 13, 2011 Belhe et al.) "External Anchoring Configurations for Modular Gastrointestinal Prostheses", 20110087146 (Apr. 14, 2011 Ryan et al.) "Stomach Bypass for the Treatment of Obesity", 20110106273 (May 5, 2011 Belhe et al.) "Gastrointestinal Prostheses Having Partial Bypass Configurations", 20110245752 (Oct. 6, 2011 Levine et al.) "Methods of Treatment Using a Bariatric Sleeve", 20110270410 (Nov. 3, 2011 Stack et al.) "Satiation Devices and Methods", 20120004676 (Jan. 5, 2012 Vargas) "Intragastric Implant Devices", 20120041465 (Feb. 16, 2012 Shalon) "Devices and Methods for Treating Gastrointestinal and Metabolic Disorders", 20120053504 (Mar. 1, 2012 Kagan et al.) "Methods for Attachment of a Gastrointestinal Sleeve", 20120065571 (Mar. 15, 2012 Thompson et al.) "Expandable Pyloric Anchors and Methods for Securing Intestinal Bypass Sleeves", 20120116286 (May 10, 2012 Williams et al.) "Intestinal Sleeves and Associated Deployment Systems and Methods", 20120184893 (Jul. 19, 2012 Thompson et al.) "Anchors and Methods for Intestinal Bypass Sleeves", 20120215152 (Aug. 23, 2012 Levine et al.) "Bariatric Sleeve", 20120232459 (Sep. 13, 2012 Dann et al.) "Devices and Methods for Endolumenal Gastrointestinal Bypass", 20120253259 (Oct. 4, 2012 Belhe et al.) "Modular Gastrointestinal Prostheses", and 20120253260 (Oct. 4, 2012 Belhe et al.) "Gastrointestinal Prostheses".

34. Gastrointestinal (GI) Sleeve or Liner (with Drug)

Prior art in this category is similar to that in the previous category, except that it also includes delivery of a pharmaceutical agent. In various examples, this category includes drug-eluting gastric sleeves and liners. Although drug delivery can provide a secondary therapeutic modality for these devices, the addition of drug delivery does not help differentiate between healthy and unhealthy food. Accordingly, these devices remain food blind. They are not able to selectively reduce absorption of nutrients from unhealthy food and allow normal absorption of nutrients from healthy food.

Examples of prior art that appear to be best classified in this category include U.S. patent applications 20110040232

(Feb. 17, 2011 Magal) "Duodenal Liner Device" and 20120232460 (Sep. 13, 2012 Raven et al.) "Intraluminal Sleeve with Active Agents".

35. Electrical Stimulation (General)

Prior art in this category includes implantable devices that deliver electromagnetic energy to a portion of a person's gastrointestinal tract or to a nerve that innervates a portion of the person's gastrointestinal tract. In an example, electrical stimulation can be applied directly to a person's stomach in order to induce a sense of satiety and/or modify gastric motility. The intent of such gastric stimulation is to reduce a person's food consumption. In another example, electrical energy can be applied to block normal neural transmissions in a nerve that innervates a person's stomach in order to reduce gastric functioning and thereby reduce food consumption. This category of art has considerable potential (no pun intended) to modify food consumption. It is relatively non-invasive with respect to other internal procedures, is adjustable, and is reversible.

In order for devices in this category to be successful in modifying food consumption, the gastrointestinal organ or nerve to which electrical energy is applied must not accommodate (ie: become inured to) the application of electrical energy. If an organ or nerve does accommodate the application of electrical energy, then the organ or nerve stops responding to the applied energy in a therapeutic manner. For this reason, devices in this category generally apply electrical energy in a non-continuous manner.

The ability to differentiate between consumption of healthy vs unhealthy food could enable such devices to selectively deliver electrical energy only when a person eats unhealthy food. This differentiating ability would allow use of higher power levels without the problem of accommodation and make such devices more effective for modifying food consumption. Such ability could also encourage the person to have a healthier diet and extend a device's battery life. However, prior art devices in this category do not appear to offer the ability to differentiate between consumption of healthy vs unhealthy food.

Examples of prior art that appear to be best classified in this category include U.S. patents: U.S. Pat. No. 3,411,507 (Nov. 19, 1968 Wingrove) "Method of Gastrointestinal Stimulation with Electrical Pulses", U.S. Pat. No. 5,188,104 (Feb. 23, 1993 Wernicke et al.) "Treatment of Eating Disorders by Nerve Stimulation", U.S. Pat. No. 5,423,872 (Jun. 13, 1995 Cigaina) "Process and Device for Treating Obesity and Syndromes Related to Motor Disorders of the Stomach of a Patient", U.S. Pat. No. 5,690,691 (Nov. 25, 1997 Chen et al.) "Gastro-Intestinal Pacemaker Having Phased Multi-Point Stimulation", U.S. Pat. No. 5,716,385 (Feb. 10, 1998 Mittal et al.) "Crural Diaphragm Pacemaker and Method for Treating Esophageal Reflux Disease (Mittal)", U.S. Pat. No. 5,891,185 (Apr. 6, 1999 Freed et al.) "Method and Apparatus for Treating Oropharyngeal Disorders with Electrical Stimulation", U.S. Pat. No. 6,091,992 (Jul. 18, 2000 Bourgeois et al.) "Method and Apparatus for Electrical Stimulation of the Gastrointestinal Tract", U.S. Pat. No. 6,243,607 (Jun. 5, 2001 Mintchev et al.) "Gastro-Intestinal Electrical Pacemaker", U.S. Pat. No. 6,564,101 (May 13, 2003 Zikria) "Electrical System for Weight Loss and Laparoscopic Implantation Thereof", U.S. Pat. No. 6,587,719 (Jul. 1, 2003 Barrett et al.) "Treatment of Obesity by Bilateral Vagus Nerve Stimulation", U.S. Pat. No. 6,609,025 (Aug. 19, 2003 Barrett et al.) "Treatment of Obesity by Bilateral Sub-Diaphragmatic Nerve Stimulation", U.S. Pat. No. 6,684,104 (Jan. 27, 2004 Gordon et al.) "Gastric Stimulator Apparatus and Method for Installing", U.S. Pat. No. 6,760,626 (Jul. 6, 2004 Boveja) "Apparatus and Method for Treatment of Neurological and Neuropsychiatric Disorders Using Programmerless Implantable Pulse Generator System", U.S. Pat. No. 6,879,859 (Apr. 12, 2005 Boveja) "External Pulse Generator for Adjunct (Add-On) Treatment of Obesity Eating Disorders Neurological Neuropsychiatric and Urological Disorders", U.S. Pat. No. 7,072,720 (Jul. 4, 2006 Puskas) "Devices and Methods for Vagus Nerve Stimulation", U.S. Pat. No. 7,167,750 (Jan. 23, 2007 Knudson et al.) "Obesity Treatment with Electrically Induced Vagal Down Regulation", U.S. Pat. No. 7,177,693 (Feb. 13, 2007 Starkebaum) "Gastric Stimulation for Altered Perception to Treat Obesity", and U.S. Pat. No. 7,236,822 (Jun. 26, 2007 Dobak) "Wireless Electric Modulation of Sympathetic Nervous System".

Examples of prior art that appear to be best classified in this category also include U.S. patents: U.S. Pat. No. 7,239,912 (Jul. 3, 2007 Dobak) "Electric Modulation of Sympathetic Nervous System", U.S. Pat. No. 7,299,091 (Nov. 20, 2007 Barrett et al.) "Treatment of Obesity by Bilateral Vagus Nerve Stimulation", U.S. Pat. No. 7,529,582 (May 5, 2009 Dilorenzo) "Method and Apparatus for Neuromodulation and Physiologic Modulation for the Treatment of Metabolic and Neuropsychiatric Disease", U.S. Pat. No. 7,551,964 (Jun. 23, 2009 Dobak) "Splanchnic Nerve Stimulation for Treatment of Obesity", U.S. Pat. No. 7,580,751 (Aug. 25, 2009 Starkebaum) "Intra-Luminal Device for Gastrointestinal Stimulation", U.S. Pat. No. 7,599,736 (Oct. 6, 2009 Dilorenzo) "Method and Apparatus for Neuromodulation and Physiologic Modulation for the Treatment of Metabolic and Neuropsychiatric Disease", U.S. Pat. No. 7,657,310 (Feb. 2, 2010 Buras) "Treatment of Reproductive Endocrine Disorders by Vagus Nerve Stimulation", U.S. Pat. No. 7,664,551 (Feb. 16, 2010 Cigaina) "Treatment of the Autonomic Nervous System", U.S. Pat. No. 7,689,276 (Mar. 30, 2010 Dobak) "Dynamic Nerve Stimulation for Treatment of Disorders", U.S. Pat. No. 7,689,277 (Mar. 30, 2010 Dobak) "Neural Stimulation for Treatment of Metabolic Syndrome and Type 2 Diabetes", U.S. Pat. No. 7,702,386 (Apr. 20, 2010 Dobak et al.) "Nerve Stimulation for Treatment of Obesity Metabolic Syndrome and Type 2 Diabetes", U.S. Pat. No. 7,729,771 (Jun. 1, 2010 Knudson et al.) "Nerve Stimulation and Blocking for Treatment of Gastrointestinal Disorders", U.S. Pat. No. 7,756,582 (Jul. 13, 2010 Imran et al.) "Gastric Stimulation Anchor and Method", U.S. Pat. No. 7,840,278 (Nov. 23, 2010 Puskas) "Devices and Methods for Vagus Nerve Stimulation", U.S. Pat. No. 7,945,323 (May 17, 2011 Jaax et al.) "Treatment of Obesity and/or Type II Diabetes by Stimulation of the Pituitary Gland", U.S. Pat. No. 7,979,127 (Jul. 12, 2011 Imran) "Digestive Organ Retention Device", U.S. Pat. No. 7,986,995 (Jul. 26, 2011 Knudson et al.) "Bulimia Treatment", U.S. Pat. No. 8,082,039 (Dec. 20, 2011 Kim et al.) "Stimulation Systems", U.S. Pat. No. 8,145,299 (Mar. 27, 2012 Dobak) "Neural Stimulation for Treatment of Metabolic Syndrome and Type 2 Diabetes", U.S. Pat. No. 8,150,508 (Apr. 3, 2012 Craig) "Vagus Nerve Stimulation Method", U.S. Pat. No. 8,280,505 (Oct. 2, 2012 Craig) "Vagus Nerve Stimulation Method", U.S. Pat. No. 8,301,256 (Oct. 30, 2012 Policker et al.) "GI Lead Implantation", and U.S. Pat. No. 8,340,772 (Dec. 25, 2012 Vase et al.) "Brown Adipose Tissue Utilization Through Neuromodulation".

Examples of prior art that appear to be best classified in this category also include U.S. patent applications: 20040167583 (Aug. 26, 2004 Knudson et al.) "Electrode Band Apparatus and Method", 20070027498 (Feb. 1, 2007 Maschino et al.) "Selective Nerve Stimulation for the Treatment of Eating Disorders", 20070135846 (Jun. 14, 2007 Knudson et al.) "Vagal Obesity Treatment", 20070150021 (Jun. 28, 2007 Chen et al.) "Gastrointestinal Electrical Stimulation", 20070203521 (Aug. 30, 2007 Dobak et al.) "Nerve Stimulation for Treatment of Obesity Metabolic Syndrome and Type 2 Diabetes", 20080046013 (Feb. 21, 2008 Lozano) "Method for Treating Eating Disorders", 20080183238 (Jul. 31, 2008 Chen) "Process for Electrostimulation Treatment of Morbid Obesity", 20080195171 (Aug. 14, 2008 Sharma) "Method and Apparatus for Electrical Stimulation of the Pancreatico-Biliary System", 20090018606 (Jan. 15, 2009 Sparks et al.) "Methods and Devices for Stimulation of an Organ with the Use of a Transectionally Placed Guide Wire", 20090259274 (Oct. 15, 2009 Simon et al.) "Methods and Apparatus for Electrical Treatment Using Balloon and Electrode", 20090259279 (Oct. 15, 2009 Dobak) "Splanchnic Nerve Stimulation for Treatment of Obesity", 20100087706 (Apr. 8, 2010 Syed et al.) "Lead Access", 20100094375 (Apr. 15, 2010 Donders et al.) "Neural Electrode Treatment", 20100168815 (Jul. 1, 2010 Knudson et al.) "Nerve Stimulation and Blocking for Treatment of Gastrointestinal Disorders", 20100183700 (Jul. 22, 2010 Stojanovic-Susulic et al.) "Implantable Pump for Protein Delivery for Obesity Control by Drug Infusion into the Brain", 20100234917 (Sep. 16, 2010 Imran) "Digestive Organ Retention Device", and 20100286745 (Nov. 11, 2010 Imran) "Radially Expandable Gastrointestinal Stimulation Device".

Examples of prior art that appear to be best classified in this category also include U.S. patent applications: 20110034967 (Feb. 10, 2011 Chen et al.) "Gastrointestinal Electrical Stimulation", 20110034968 (Feb. 10, 2011 Knudson et al.) "Controlled Vagal Blockage Therapy", 20110166582 (Jul. 7, 2011 Syed et al.) "Endoscopic Device Delivery System", 20110230938 (Sep. 22, 2011 Simon et al.) "Device and Methods for Non-Invasive Electrical Stimulation and Their Use for Vagal Nerve Stimulation", 20110238035 (Sep. 29, 2011 Jaax et al.) "Treatment of Obesity and/or Type II Diabetes by Stimulation of the Pituitary Gland", 20110270344 (Nov. 3, 2011 Knudson et al.) "Bulimia Treatment", 20110307023 (Dec. 15, 2011 Tweden et al.) "Neural Modulation Devices and Methods", 20110319969 (Dec. 29, 2011 Dobak) "Electric Modulation of Sympathetic Nervous System", 20120041509 (Feb. 16, 2012 Knudson et al.) "Controlled Vagal Blockage Therapy", 20120053653 (Mar. 1, 2012 Hiernaux et al.) "Gastrointestinal Device", 20120053660 (Mar. 1, 2012 Dobak) "Splanchnic Nerve Stimulation for Treatment of Obesity", 20120071947 (Mar. 22, 2012 Gupta et al.) "Method and Apparatus for Event-Triggered Reinforcement of a Favorable Brain State", 20120143279 (Jun. 7, 2012 Ekchian et al.) "Methods and Kits for Treating Appetite Suppressing Disorders and Disorders with an Increased Metabolic Rate", 20120209354 (Aug. 16, 2012 Raykhman) "System and Methods for Producing and Delivering Electrical Impulses", and 20120310295 (Dec. 6, 2012 Libbus et al.) "Systems and Methods for Avoiding Neural Stimulation Habituation".

36. Electrical Stimulation (with Glucose Sensor)

Devices in this category are similar to devices in the previous category of general electrical stimulation except that they also include a glucose sensor. They deliver electromagnetic energy to person's gastrointestinal tract or to a nerve that innervates their gastrointestinal tract. In an example, a person's blood glucose level can be monitored and gastrointestinal electrical stimulation can be triggered when the person's glucose level indicates that such stimulation is most needed. Selective electrical stimulation can help to target therapeutic benefit.

Examples of prior art that appear to be best classified in this category include U.S. patents: U.S. Pat. No. 6,093,167 (Jul. 25, 2000 Houben et al.) "System for Pancreatic Stimulation and Glucose Measurement", U.S. Pat. No. 6,185,452 (Feb. 6, 2001 Schulman et al.) "Battery-Powered Patient Implantable Device", U.S. Pat. No. 6,571,127 (May 27, 2003 Ben-Haim et al.) "Method of Increasing the Motility of a GI Tract", U.S. Pat. No. 6,600,953 (Jul. 29, 2003 Flesler et al.) "Acute and Chronic Electrical Signal Therapy for Obesity", U.S. Pat. No. 6,832,114 (Dec. 14, 2004 Whitehurst et al.) "Systems and Methods for Modulation of Pancreatic Endocrine Secretion and Treatment of Diabetes", U.S. Pat. No. 6,922,590 (Jul. 26, 2005 Whitehurst) "Systems and Methods for Treatment of Diabetes by Electrical Brain Stimulation and/or Drug Infusion", U.S. Pat. No. 6,993,391 (Jan. 31, 2006 Flesler et al.) "Acute and Chronic Electrical Signal Therapy for Obesity", U.S. Pat. No. 7,020,531 (Mar. 28, 2006 Colliou et al.) "Gastric Device and Suction Assisted Method for Implanting a Device on a Stomach Wall", U.S. Pat. No. 7,440,806 (Oct. 21, 2008 Whitehurst et al.) "Systems and Methods for Treatment of Diabetes by Electrical Brain Stimulation and/or Drug Infusion", U.S. Pat. No. 7,477,944 (Jan. 13, 2009 Whitehurst et al.) "Systems and Methods for Modulation of Pancreatic Endocrine Secretion and Treatment of Diabetes", U.S. Pat. No. 7,502,649 (Mar. 10, 2009 Ben-Haim et al.) "Gastrointestinal Methods and Apparatus for Use in Treating Disorders", U.S. Pat. No. 7,512,442 (Mar. 31, 2009 Flesler et al.) "Acute and Chronic Electrical Signal Therapy for Obesity", U.S. Pat. No. 7,558,629 (Jul. 7, 2009 Keimel et al.) "Energy Balance Therapy for Obesity Management", U.S. Pat. No. 7,937,145 (May 3, 2011 Dobak) "Dynamic Nerve Stimulation Employing Frequency Modulation", U.S. Pat. No. 8,019,421 (Sep. 13, 2011 Darvish et al.) "Blood Glucose Level Control", U.S. Pat. No. 8,095,218 (Jan. 10, 2012 Gross et al.) "GI and Pancreatic Device for Treating Obesity and Diabetes", U.S. Pat. No. 8,135,470 (Mar. 13, 2012 Keimel et al.) "Energy Balance Therapy for Obesity Management", U.S. Pat. No. 8,209,037 (Jun. 26, 2012 Laufer et al.) "Methods and Devices for Medical Treatment", U.S. Pat. No. 8,321,030 (Nov. 27, 2012 Maniak et al.) "Esophageal Activity Modulated Obesity Therapy", U.S. Pat. No. 8,321,030 (Nov. 27, 2012 Maniak et al.) "Esophageal Activity Modulated Obesity Therapy", and U.S. Pat. No. 8,346,363 (Jan. 1, 2013 Darvish et al.) "Blood Glucose Level Control".

Examples of prior art that appear to be best classified in this category also include U.S. patent applications: 20040044376 (Mar. 4, 2004 Flesler et al.) "Acute and Chronic Electrical Signal Therapy for Obesity", 20050149142 (Jul. 7, 2005 Starkebaum) "Gastric Stimulation Responsive to Sensing Feedback", 20050222638 (Oct. 6, 2005 Foley et al.) "Sensor Based Gastrointestinal Electrical Stimulation for the Treatment of Obesity or Motility Disorders", 20060074459 (Apr. 6, 2006 Flesler et al.) "Acute and Chronic Electrical Signal Therapy for Obesity", 20070016262 (Jan. 18, 2007 Gross et al.) "GI and Pancreatic Device for Treating Obesity and Diabetes", 20070027493 (Feb. 1, 2007 Ben-Haim et al.) "Gastrointestinal Methods and Apparatus for Use in Treating Disorders and Controlling Blood Sugar", 20070179556 (Aug. 2, 2007 Ben-Haim et al.) "Gastrointestinal Methods and Apparatus for Use in Treating Disorders", 20070255334 (Nov. 1, 2007 Keimel et al.) "Energy Balance Therapy for Obesity Management", 20090018594 (Jan. 15, 2009 Laufer et al.) "Methods and Devices for Medical Treatment", 20090030474 (Jan. 29, 2009 Brynelsen et al.) "Sensor Driven Gastric Stimulation for Patient Management", 20090062881 (Mar. 5, 2009 Gross et al.) "GI and Pancreatic Device for Treating Obesity and Diabetes", 20090088816 (Apr. 2, 2009 Harel et al.) "Gastrointestinal Methods and Apparatus for Use in Treating Disorders and Controlling Blood Sugar", 20090240194 (Sep. 24, 2009 Keimel et al.) "Energy Balance Therapy for Obesity Management", 20100268306 (Oct. 21, 2010 Maniak et al.) "Esophageal Activity Modulated Obesity Therapy", 20110087076 (Apr. 14, 2011 Brynelsen et al.) "Feedback Systems and Methods for Communicating Diagnostic and/or Treatment Signals to Enhance Obesity Treatments", 20120083855 (Apr. 5, 2012 Gross et al.) "GI and Pancreatic Device for Treating Obesity and Diabetes", 20120214140 (Aug. 23, 2012 Brynelsen et al.) "Feedback Systems and Methods for Communicating Diagnostic and/or Treatment Signals to Enhance Obesity Treatments", 20120259389 (Oct. 11, 2012 Starkebaum et al.) "Treatment of Postprandial Hyperglycemia by Gastric Electrical Stimulation", and 20120323099 (Dec. 20, 2012 Mothilal et al.) "Implantable Medical Device Electrode Assembly".

37. Electrical Stimulation (with General Sensor)

Devices in this category are similar to devices in the prior category of general electrical stimulation except that they also include one or more sensors other than a glucose sensor. Like devices in prior categories, they deliver electromagnetic energy to person's gastrointestinal tract or to a nerve that innervates their gastrointestinal tract. In an example, the electromagnetic properties of a person's esophagus or stomach can be monitored by an electromagnetic sensor and gastrointestinal electrical stimulation can be triggered when the sensor indicates that a person is consuming food. Selective electrical stimulation can help to target therapeutic benefit.

Examples of prior art that appear to be best classified in this category include U.S. patents: U.S. Pat. No. 5,263,480 (Nov. 23, 1993 Wernicke et al.) "Treatment of Eating Disorders by Nerve Stimulation", U.S. Pat. No. 5,292,344 (Mar. 8, 1994 Douglas) "Percutaneously Placed Electrical Gastrointestinal Pacemaker Stimulatory System, Sensing System, and PH Monitoring System, with Optional Delivery Port", U.S. Pat. No. 5,540,730 (Jul. 30, 1996 Terry et al.) "Treatment of Motility Disorders by Nerve Stimulation", U.S. Pat. No. 5,836,994 (Nov. 17, 1998 Bourgeois) "Method and Apparatus for Electrical Stimulation of the Gastrointestinal Tract", U.S. Pat. No. 5,861,014 (Jan. 19, 1999 Familoni) "Method and Apparatus for Sensing a Stimulating Gastrointestinal Tract On-Demand", U.S. Pat. No. 5,995,872 (Nov. 30, 1999 Bourgeois) "Method and Apparatus for Electrical Stimulation of the Gastrointestinal Tract", U.S. Pat. No. 6,083,249 (Jul. 4, 2000 Familoni) "Apparatus for Sensing and Stimulating Gastrointestinal Tract On-Demand", U.S. Pat. No. 6,104,955 (Aug. 15, 2000 Bourgeois) "Method and Apparatus for Electrical Stimulation of the Gastrointestinal Tract", U.S. Pat. No. 6,115,635 (Sep. 5, 2000 Bourgeois) "Method and Apparatus for Electrical Stimulation of the Gastrointestinal Tract", U.S. Pat. No. 6,216,039 (Apr. 10, 2001 Bourgeois) "Method and Apparatus for Treating Irregular Gastric Rhythms", U.S. Pat. No. 6,327,503 (Dec. 4, 2001 Familoni) "Method and Apparatus for Sensing and Stimulating Gastrointestinal Tract On-Demand", U.S. Pat. No. 6,535,764 (Mar. 18, 2003 Imran et al.) "Gastric Treatment and Diagnosis Device and Method (Intrapace: Imran)", U.S. Pat. No. 6,591,137 (Jul. 8, 2003 Fischell et al.) "Implantable Neuromuscular Stimulator for the Treatment of Gastrointestinal Disorders", and U.S. Pat. No. 6,735,477 (May 11, 2004 Levine) "Internal Monitoring System with Detection of Food Intake".

Examples of prior art that appear to be best classified in this category also include U.S. patents: U.S. Pat. No. 6,826,428 (Nov. 30, 2004 Chen et al.) "Gastrointestinal Electrical Stimulation", U.S. Pat. No. 6,993,391 (Jan. 31, 2006 Flesler et al.) "Acute and Chronic Electrical Signal Therapy for Obesity", U.S. Pat. No. 7,054,690 (May 30, 2006 Imran) "Gastrointestinal Stimulation Device", U.S. Pat. No. 7,120,498 (Oct. 10, 2006 Imran et al.) "Method and Device for Securing a Functional Device to a Stomach", U.S. Pat. No. 7,430,450 (Sep. 30, 2008 Imran) "Device and Method for Treating Obesity", U.S. Pat. No. 7,437,195 (Oct. 14, 2008 Policker et al.) "Regulation of Eating Habits", U.S. Pat. No. 7,509,174 (Mar. 24, 2009 Imran et al.) "Gastric Treatment/ Diagnosis Device and Attachment Device and Method", U.S. Pat. No. 7,620,454 (Nov. 17, 2009 Dinsmoor et al.) "Gastro-Electric Stimulation for Reducing the Acidity of Gastric Secretions or Reducing the Amounts Thereof", U.S. Pat. No. 7,643,887 (Jan. 5, 2010 Imran) "Abdominally Implanted Stimulator and Method", U.S. Pat. No. 7,702,394 (Apr. 20, 2010 Imran) "Responsive Gastric Stimulator", U.S. Pat. No. 7,738,961 (Jun. 15, 2010 Sharma) "Method and Apparatus for Treatment of the Gastrointestinal Tract", U.S. Pat. No. 7,742,818 (Jun. 22, 2010 Dinsmoor et al.) "Gastro-Electric Stimulation for Increasing the Acidity of Gastric Secretions or Increasing the Amounts Thereof", U.S. Pat. No. 7,881,797 (Feb. 1, 2011 Griffin et al.) "Methods and Devices for Gastrointestinal Stimulation", U.S. Pat. No. 7,941,221 (May 10, 2011 Foley) "Method and Apparatus for Intentional Impairment of Gastric Motility and/or Efficiency by Triggered Electrical Stimulation of the Gastrointestinal . . . ", U.S. Pat. No. 8,214,049 (Jul. 3, 2012 Brynelsen et al.) "Gastric Stimulation Systems and Methods Utilizing a Transgastric Probe", and U.S. Pat. No. 8,239,027 (Aug. 7, 2012 Imran) "Responsive Gastric Stimulator".

Examples of prior art that appear to be best classified in this category also include U.S. patent applications: 20020072780 (Jun. 13, 2002 Foley) "Method and Apparatus for Intentional Impairment of Gastric Motility and/or Efficiency by Triggered Electrical Stimulation of the Gastrointestinal Tract . . . ", 20030009202 (Jan. 9, 2003 Levine) "Internal Monitoring System with Detection of Food Intake", 20040059393 (Mar. 25, 2004 Policker et al.) "Regulation of Eating Habits", 20040088023 (May 6, 2004 Imran et al.) "Gastric Treatment and Diagnosis Device and Method", 20040162595 (Aug. 19, 2004 Foley) "Method and Apparatus for Intentional Impairment of Gastric Motility and/or Efficiency by Triggered Electrical Stimulation of the Gastrointestinal Tract . . . ", 20050065571 (Mar. 24, 2005 Imran) "Responsive Gastric Stimulator", 20050090873 (Apr. 28, 2005 Imran) "Gastrointestinal Stimulation Device", 20060079944 (Apr. 13, 2006 Imran) "Device and Method for Treating Obesity", 20060089699 (Apr. 27, 2006 Imran) "Abdominally Implanted Stimulator and Method", 20070060812 (Mar. 15, 2007 Harel et al.) "Sensing of Pancreatic Electrical Activity", 20070162085 (Jul. 12, 2007 Dilorenzo) "Method Apparatus Surgical Technique and Stimulation Parameters for Autonomic Neuromodulation for the Treatment of Obesity", 20080058887 (Mar. 6, 2008 Griffin et al.) "Methods and Devices for Gastrointestinal Stimulation", 20080086179 (Apr. 10, 2008 Sharma) "Method and Apparatus for Treatment of the Gastrointestinal Tract", 20090018605 (Jan. 15, 2009 Imran et al.) "Gastric Treatment/Diagnosis Device and Attachment Device and Method", 20090018605 (Jan. 15, 2009 Imran et al.) "Gastric Treatment/Diagnosis Device and Attachment Device and Method", 20090030475 (Jan. 29, 2009 Brynelsen et al.) "Gastric Stimulation Systems and Methods Utilizing a Transgastric Probe", and 20090149910 (Jun. 11, 2009 Imran et al.) "Gastric Treatment/Diagnosis Device and Attachment Device and Method".

Examples of prior art that appear to be best classified in this category also include U.S. patent applications: 20090264951 (Oct. 22, 2009 Sharma) "Device and Implantation System for Electrical Stimulation of Biological Systems", 20100049274 (Feb. 25, 2010 Cholette) "Detection of Feeding Intent for Use in Treatment of Eating Disorders", 20100049274 (Feb. 25, 2010 Cholette) "Detection of Feeding Intent for Use in Treatment of Eating Disorders", 20100094374 (Apr. 15, 2010 Imran) "Responsive Gastric Stimulator", 20100305656 (Dec. 2, 2010 Imran et al.) "Gastric Stimulation Anchor and Method", 20100324432 (Dec. 23, 2010 Bjorling et al.) "Method and Device to Detect Eating to Control Artificial Gastric Stimulation", 20110004266 (Jan. 6, 2011 Sharma) "Method and Apparatus for Treatment of the Gastrointestinal Tract", 20110066207 (Mar. 17, 2011 Imran) "Responsive Gastric Stimulator", 20110125211 (May 26, 2011 Griffin et al.) "Methods and Devices for Gastrointestinal Stimulation", 20110251495 (Oct. 13, 2011 Province et al.) "Diagnostic Sensors and/or Treatments for Gastrointestinal Stimulation or Monitoring Devices", 20110295335 (Dec. 1, 2011 Sharma et al.) "Device and Implantation System for Electrical Stimulation of Biological Systems", 20110295336 (Dec. 1, 2011 Sharma et al.) "Device and Implantation System for Electrical Stimulation of Biological Systems", 20110307027 (Dec. 15, 2011 Sharma et al.) "Device and Implantation System for Electrical Stimulation of Biological Systems", 20110307028 (Dec. 15, 2011 Sharma et al.) "Device and Implantation System for Electrical Stimulation of Biological Systems", 20120277619 (Nov. 1, 2012 Starkebaum et al.) "Detecting Food Intake Based on Impedance", and 20120316451 (Dec. 13, 2012 Province et al.) "Event Evaluation Using Heart Rate Variation for Ingestion Monitoring and Therapy".

38. Electrical Stimulation (with Taste Modification)

Devices in this category are similar to devices in the prior category of general electrical stimulation except that they specifically modify a person's sense of taste. In an example, nerves that innervate a person's taste buds can be stimulated to modify a person's sense of taste and thereby modify their food consumption.

Examples of prior art that appear to be best classified in this category include U.S. patent applications: 20060173508 (Aug. 3, 2006 Stone et al.) "Method and System for Treatment of Eating Disorders by Means of Neuro-Electrical Coded Signals", 20060206169 (Sep. 14, 2006 Schuler) "Method and System for Modulating Eating Behavior by Means of Neuro-Electrical Coded Signals", 20060235487 (Oct. 19, 2006 Meyer et al.) "Method and System for Treatment of Eating Disorders by Means of Neuro-Electrical Coded Signals", 20110276112 (Nov. 10, 2011 Simon et al.) "Devices and Methods for Non-Invasive Capacitive Electrical Stimulation and Their Use for Vagus Nerve Stimulation on the Neck of a Patient", 20120029591 (Feb. 2, 2012 Simon et al.) "Devices and Methods for Non-Invasive Capacitive Electrical Stimulation and Their Use for Vagus Nerve Stimulation on the Neck of a Patient", 20120029601 (Feb. 2, 2012 Simon et al.) "Devices and Methods for Non-Invasive Capacitive Electrical Stimulation and Their Use for Vagus Nerve Stimulation on the Neck of a Patient", 20120277814 (Nov. 1, 2012 Schuler) "Method and System for Modulating Eating Behavior by Means of Neuro-Electrical Coded Signals", and 20120277837 (Nov. 1, 2012 Schuler) "Method and System for Modulating Eating Behavior by Means of Neuro-Electrical Coded Signals".

39. Electrical Stimulation (with Drug)

Devices in this category are similar to devices in the prior category of general electrical stimulation except that they also include a drug delivery mechanism. In addition to delivering electromagnetic energy to person's gastrointestinal tract or to a nerve that innervates their gastrointestinal tract, devices in this category can also include an implantable drug pump. In an example, electrical stimulation can be used in conjunction with drug delivery to create combined therapeutic effects.

Examples of prior art that appear to be best classified in this category include: U.S. Pat. No. 5,782,798 (Jul. 21, 1998 Rise) "Techniques for Treating Eating Disorders by Brain Stimulation and Drug Infusion", U.S. Pat. No. 7,493,171 (Feb. 17, 2009 Whitehurst et al.) "Treatment of Pathologic Craving and Aversion Syndromes and Eating Disorders by Electrical Brain Stimulation and/or Drug Infusion", U.S. Pat. No. 7,835,796 (Nov. 16, 2010 Maschino et al.) "Weight Loss Method and Device", U.S. Pat. No. 8,010,204 (Aug. 30, 2011 Knudson et al.) "Nerve Blocking for Treatment of Gastrointestinal Disorders", U.S. Pat. No. 8,185,206 (May 22, 2012 Starkebaum et al.) "Electrical Stimulation Therapy to Promote Gastric Distention for Obesity Management", and U.S. Pat. No. 8,295,926 (Oct. 23, 2012 Dobak) "Dynamic Nerve Stimulation in Combination with Other Eating Disorder Treatment Modalities"; and U.S. patent applications 20080021512 (Jan. 24, 2008 Knudson et al.) "Nerve Stimulation and Blocking for Treatment of Gastrointestinal Disorders", 20080262411 (Oct. 23, 2008 Dobak) "Dynamic Nerve Stimulation in Combination with Other Eating Disorder Treatment Modalities", 20110282411 (Nov. 17, 2011 Knudson et al.) "Nerve Stimulation and Blocking for Treatment of Gastrointestinal Disorders", 20110282411 (Nov. 17, 2011 Knudson et al.) "Nerve Stimulation and Blocking for Treatment of Gastrointestinal Disorders", and 20120277661 (Nov. 1, 2012 Bernard et al.) "Method and Apparatus for Delivery of Therapeutic Agents".

40. Electrical Stimulation (with Drug and Sensor)

Devices in this category are similar to devices in a prior category of general electrical stimulation except that they also include a drug delivery mechanism and at least one sensor. In an example, electrical stimulation can be used in conjunction with drug delivery to create combined therapeutic effects. Further, the sensor can be used to create a self-adjusting, closed-loop stimulation and/or drug delivery system for modification of food consumption.

Examples of prior art that appear to be best classified in this category include: U.S. Pat. No. 6,950,707 (Sep. 27, 2005 Whitehurst) "Systems and Methods for Treatment of Obesity and Eating Disorders by Electrical Brain Stimulation and/or Drug Infusion", U.S. Pat. No. 7,076,305 (Jul. 11, 2006 Imran et al.) "Gastric Device and Instrument System and Method", U.S. Pat. No. 7,483,746 (Jan. 27, 2009 Lee et al.) "Stimulation of the Stomach in Response to Sensed Parameters to Treat Obesity", U.S. Pat. No. 7,590,452 (Sep. 15, 2009 Imran et al.) "Endoscopic System for Attaching a Device to a Stomach", and U.S. Pat. No. 8,095,219 (Jan. 10, 2012 Lee et al.) "Stimulation of the Stomach in Response to Sensed Parameters to Treat Obesity"; and U.S. patent applications 20030167024 (Sep. 4, 2003 Imran et al.) "Gastric Device and Instrument System and Method", 20040243195 (Dec. 2, 2004 Imran et al.) "Endoscopic System for Attaching a Device to a Stomach", 20060129201 (Jun. 15, 2006 Lee et al.) "Stimulation of the Stomach in Response to Sensed Parameters to Treat Obesity", and 20090299434 (Dec. 3, 2009 Imran et al.) "Endoscopic System for Attaching a Device to a Stomach".

41. Salivation Stimulation

This category of prior art includes devices and methods for stimulating salivation in a person's mouth. In some respects, this is quite different than devices and methods that are intended to reduce food consumption. Most devices and methods in this category are focused on increasing, not decreasing, food consumption. However, this category is included for completeness because some of these devices are intended to modify the early stages of food digestion within a person's mouth, which can be relevant. In an example, devices in this category can apply electrical stimulation to the mouth to increase salivation. In an example, devices in this category can release a salivation-stimulating substance.

Examples of prior art that appear to be best classified in this category include: U.S. Pat. No. 4,519,400 (May 28, 1985 Brenman et al.) "Method for Stimulating Salivation (Biosonics)", U.S. Pat. No. 4,637,405 (Jan. 20, 1987 Brenman et al.) "Apparatus for Stimulating Salivation", U.S. Pat. No. 6,230,052 (May 8, 2001 Wolff et al.) "Device and Method for Stimulating Salivation", U.S. Pat. No. 7,041,311 (May 9, 2006 Grainger et al.) "Preparation for Saliva Flow", and U.S. Pat. No. 7,477,947 (Jan. 13, 2009 Pines et al.) "System and Method for Electrical Stimulation of Salivation"; and U.S. patent application 20070077300 (Apr. 5, 2007 Wynn et al.) "Oral Compositions Containing a Salivation Inducing Agent".

42. General Sensor (Glucose)

This category of prior art includes sensors and monitors which detect and analyze glucose levels (such as blood glucose levels). These sensors and monitors can be used for a variety of applications other than modification of food consumption or food absorption. For example, they can be used to determine when a diabetic person needs insulin. Nonetheless, overall, they are sufficiently relevant to be included in this review.

Examples of prior art that appear to be best classified in this category include: U.S. Pat. No. 5,497,772 (Mar. 12, 1996 Schulman et al.) "Glucose Monitoring System", U.S. Pat. No. 7,727,147 (Jun. 1, 2010 Osorio et al.) "Method and System for Implantable Glucose Monitoring and Control of a Glycemic State of a Subject", U.S. Pat. No. 7,974,672 (Jul. 5, 2011 Shults et al.) "Device and Method for Determining Analyte Levels", U.S. Pat. No. 7,988,630 (Aug. 2, 2011 Osorio et al.) "Method and System for Implantable Glucose Monitoring and Control of a Glycemic State of a Subject", U.S. Pat. No. 8,158,082 (Apr. 17, 2012 Imran) "Micro-Fluidic Device", U.S. Pat. No. 8,236,242 (Aug. 7, 2012 Drucker et al.) "Blood Glucose Tracking Apparatus and Methods", U.S. Pat. No. 8,275,438 (Sep. 25, 2012 Simpson et al.) "Analyte Sensor", U.S. Pat. No. 8,287,453 (Oct. 16, 2012 Li et al.) "Analyte Sensor", and U.S. Pat. No. 8,298,142 (Oct. 30, 2012 Simpson et al.) "Analyte Sensor"; and U.S. patent applications 20050096637 (May 5, 2005 Heruth) "Sensing Food Intake", 20120078071 (Mar. 29, 2012 Bohm et al.) "Advanced Continuous Analyte Monitoring System", 20120149996 (Jun. 14, 2012 Stivoric et al.) "Method and Apparatus for Providing Derived Glucose Information Utilizing Physiological and/or Contextual Parameters", and 20120201725 (Aug. 9, 2012 Imran) "Micro-Fluidic Device".

43. General Sensor (Electromagnetic)

This category of prior art includes sensors and monitors which detect selected patterns of electromagnetic energy that are emitted from a member of a person's body. Such sensors and monitors can be used for a variety of applications other than modification of food consumption or food absorption. Nonetheless, overall, they are sufficiently relevant to be included in this review.

Examples of prior art that appear to be best classified in this category include: U.S. Pat. No. 5,795,304 (Aug. 18, 1998 Sun et al.) "System and Method for Analyzing Electrogastrophic Signal", U.S. Pat. No. 6,285,897 (Sep. 4, 2001 Kilcoyne et al.) "Remote Physiological Monitoring System", U.S. Pat. No. 8,192,350 (Jun. 5, 2012 Ortiz et al.) "Methods and Devices for Measuring Impedance in a Gastric Restriction System", U.S. Pat. No. 8,265,758 (Sep. 11, 2012 Policker et al.) "Wireless Leads for Gastrointestinal Tract Applications", and U.S. Pat. No. 8,328,420 (Dec. 11, 2012 Abreu) "Apparatus and Method for Measuring Biologic Parameters"; and U.S. patent applications 20080262557 (Oct. 23, 2008 Brown) "Obesity Management System", 20090281449 (Nov. 12, 2009 Thrower et al.) "Optimization of Thresholds for Eating Detection", 20100305468 (Dec. 2, 2010 Policker et al.) "Analysis and Regulation of Food Intake", and 20120316459 (Dec. 13, 2012 Abreu) "Apparatus and Method for Measuring Biologic Parameters".

44. General Sensor (Chemical)

This category of prior art includes sensors which can detect specific types of chemicals. Such sensors can be used for a variety of applications other than modification of food consumption or food absorption. Some are not even directed toward biomedical applications. Nonetheless, overall, they are sufficiently relevant to be included in this review.

Examples of prior art that appear to be best classified in this category include: U.S. Pat. No. 6,218,358 (Apr. 17, 2001 Firestein et al.) "Functional Expression of, and Assay for, Functional Cellular Receptors In Vivo", U.S. Pat. No. 6,387,329 (May 14, 2002 Lewis et al.) "Use of an Array of Polymeric Sensors of Varying Thickness for Detecting Analytes in Fluids", U.S. Pat. No. 6,610,367 (Aug. 26, 2003 Lewis et al.) "Use of an Array of Polymeric Sensors of Varying Thickness for Detecting Analytes in Fluids", U.S. Pat. No. 7,122,152 (Oct. 17, 2006 Lewis et al.) "Spatiotemporal and Geometric Optimization of Sensor Arrays for Detecting Analytes Fluids", U.S. Pat. No. 7,241,880 (Jul. 10, 2007 Adler et al.) "T1R Taste Receptors and Genes Encoding Same", U.S. Pat. No. 7,595,023 (Sep. 29, 2009 Lewis et al.) "Spatiotemporal and Geometric Optimization of Sensor Arrays for Detecting Analytes in Fluids", U.S. Pat. No. 7,651,868 (Jan. 26, 2010 Mcdevitt et al.) "Method and System for the Analysis of Saliva using a Sensor Array", U.S. Pat. No. 8,067,185 (Nov. 29, 2011 Zoller et al.) "Methods of Quantifying Taste of Compounds for Food or Beverages", U.S. Pat. No. 8,314,224 (Nov. 20, 2012 Adler et al.) "T1R Taste Receptors and Genes Encoding Same", and U.S. Pat. No. 8,334,367 (Dec. 18, 2012 Adler) "T2R Taste Receptors and Genes Encoding Same"; and U.S. patent applications 20090261987 (Oct. 22, 2009 Sun) "Sensor Instrument System Including Method for Detecting Analytes in Fluids", and 20120015432 (Jan. 19, 2012 Adler) "Isolated Bitter Taste Receptor Polypeptides".

45. General Sensor (Microwave)

This category of prior art includes sensors which can detect selected patterns of microwave energy. Such sensors can be used for a variety of applications other than modification of food consumption or food absorption. Nonetheless, overall, they are sufficiently relevant to be included in this review. Examples of prior art that appear to be best classified in this category include U.S. patent applications 20120053426 (Mar. 1, 2012 Webster et al.) "System and Method for Measuring Calorie Content of a Food Sample" and 20130027060 (Jan. 31, 2013 Tralshawala et al.) "Systems and Methods for Non-Destructively Measuring Calorie Contents of Food Items".

46. Sensor (Intraoral)

This category of prior art includes sensors and monitors which are specifically attached or implanted within a person's oral cavity. Examples of prior art that appear to be best classified in this category include: U.S. Pat. No. 8,233,954 (Jul. 31, 2012 Kling et al.) "Mucosal Sensor for the Assessment of Tissue and Blood Constituents and Technique for Using the Same"; and U.S. patent applications 20050263160 (Dec. 1, 2005 Utley et al.) "Intraoral Aversion Devices and Methods", 20060020298 (Jan. 26, 2006 Camilleri et al.) "Systems and Methods for Curbing Appetite", 20070106138 (May 10, 2007 Beiski et al.) "Intraoral Apparatus for Non-Invasive Blood and Saliva Monitoring & Sensing", and 20100209897 (Aug. 19, 2010 Utley et al.) "Intraoral Behavior Monitoring and Aversion Devices and Methods".

47. Sensor (General)

This category of prior art includes general sensors which can be used for a variety of applications other than modification of food consumption or food absorption. Nonetheless, overall, they are sufficiently relevant to merit inclusion in this review.

Examples of prior art that appear to be best classified in this category include: U.S. Pat. No. 4,823,808 (Apr. 25, 1989 Clegg et al.) "Method for Control of Obesity Overweight and Eating Disorders", U.S. Pat. No. 5,301,679 (Apr. 12, 1994 Taylor) "Method and System for Analysis of Body Sounds", U.S. Pat. No. 6,365,128 (Apr. 2, 2002 Bennett-Guerrero et al.) "Monitoring Gastrointestinal Function to Guide Care of High Risk Patients", and U.S. Pat. No. 7,832,407 (Nov. 16, 2010 Gertner) "Obesity Treatment Systems"; and U.S. patent applications 20060089571 (Apr. 27, 2006 Gertner) "Obesity Treatment Systems", 20090118797 (May 7, 2009 Kliger et al.) "Monitoring, Analysis, and Regulation of Eating Habits", 20100160745 (Jun. 24, 2010 Hills et al.) "Detection of Food or Drink Consumption in Order to Control Therapy or Provide Diagnostics", 20120116182 (May 10, 2012 Wong et al.) "Feedback Systems and Methods to Enhance Obstructive and Other Obesity Treatments, Optionally Using Multiple Sensors", and 20120232361 (Sep. 13, 2012 Birk) "Bariatric Instrument or Accessory with Sensors".

48. Blood Analysis and Monitoring

Prior art in this category includes devices and methods that analyze the flow and/or composition of a person's blood. In an example, a sensor can infer whether a person is consuming food by monitoring blood flow through tissue that is related to food consumption and digestion.

Examples of prior art that appear to be best classified in this category include: U.S. Pat. No. 5,398,688 (Mar. 21, 1995 Laniado) "Method, System and Instrument for Monitoring Food Intake", U.S. Pat. No. 6,893,406 (May 17, 2005 Takeuchi et al.) "Mastication Monitoring Device", and U.S. Pat. No. 7,006,871 (Feb. 28, 2006 Darvish et al.) "Blood Glucose Level Control"; and U.S. patent applications 20040073142 (Apr. 15, 2004 Takeuchi et al.) "Mastication Monitoring Device", and 20110218407 (Sep. 8, 2011 Haberman et al.) "Method and Apparatus to Monitor, Analyze and Optimize Physiological State of Nutrition".

49. General Energy Balance Feedback

This category of prior art includes a wide variety of relatively-general systems, devices, and methods that are intended to provide a person with support and feedback concerning their energy balance and weight management. In various examples, systems, devices, and methods in this category can involve: general feedback and behavior modification concerning diet and exercise patterns; broadly-defined use of general types of sensors for energy balance and weight management; interactive communication between people and healthcare providers, or between people and social support networks; internet websites that provide online support for energy balance and weight management; and general meal planning systems and methods. Much of the prior art in this category can be very useful, but is very general compared to the specificity of this present invention. Nonetheless, this general category is included in this review in order to be thorough.

Examples of prior art that appear to be best classified in this category include: U.S. Pat. No. 4,951,197 (Aug. 21, 1990 Mellinger) "Weight Loss Management System", U.S. Pat. No. 5,720,771 (Feb. 24, 1998 Snell) "Method and Apparatus for Monitoring Physiological Data from an Implantable Medical Device", U.S. Pat. No. 6,154,676 (Nov. 28, 2000 Levine) "Internal Monitoring and Behavior Control System (Robert Levine)", U.S. Pat. No. 6,334,073 (Dec. 25, 2001 Levine) "Internal Monitoring and Behavior Control System", U.S. Pat. No. 6,735,479 (May 11, 2004 Fabian et al.) "Lifestyle Management System", U.S. Pat. No. 7,247,023 (Jul. 24, 2007 Peplinski et al.) "System and method for monitoring weight and nutrition (Daniel Peplinski)", and U.S. Pat. No. 7,882,150 (Feb. 1, 2011 Badyal) "Health Advisor"; and U.S. patent applications 20050113649 (May 26, 2005 Bergantino) "Method and Apparatus for Managing a User's Health", 20060015016 (Jan. 19, 2006 Thornton) "Caloric Balance Weight Control System and Methods of Making and Using Same", 20060122468 (Jun. 8, 2006 Tavor) "Nutritional Counseling Method and Server", 20070021979 (Jan. 25, 2007 Cosentino et al.) "Multiuser Wellness Parameter Monitoring System", 20080221644 (Sep. 11, 2008 Vallapureddy et al.) "Remote Monitoring and Control of Implantable Devices", and 20120065706 (Mar. 15, 2012 Vallapureddy et al.) "Remote Monitoring and Control of Implantable Devices".

50. Miscellaneous Energy Balance Related Devices and Methods

Lastly, this category of prior art includes a variety of devices and methods that may be generally relevant to the measurement and modification of food consumption, but which resist neat categorization. Examples of prior art in this miscellaneous category include: altering food perception through the use of special tableware; devices that a person activates to emit a bad smell to reduce their appetite; devices that a person uses to shock their tongue when they have a craving; devices to increase airflow through the nose; methods for identifying olfactory cells; time-restricted food containers to control access to food; and using tongue stimulation as a sensory substitute for vision.

Examples of prior art that appear to be best classified in this category include U.S. patents: U.S. Pat. No. 4,582,492 (Apr. 15, 1986 Etter et al.) "Method for Behavior Modification Using Olfactory Stimuli", U.S. Pat. No. 5,792,210 (Aug. 11, 1998 Wamubu et al.) "Electrical Tongue Stimulator and Method for Addiction Treatment", U.S. Pat. No. 6,145,503 (Nov. 14, 2000 Smith) "Olfactory Activator", U.S. Pat. No. 6,159,145 (Dec. 12, 2000 Satoh) "Appetite Adjusting Tool", U.S. Pat. No. 7,409,647 (Aug. 5, 2008 Elber et al.) "Control of Interactions Within Virtual Environments", and U.S. Pat. No. 8,060,220 (Nov. 15, 2011 Liebergesell et al.) "Promotion of Oral Hygiene and Treatment of Gingivitis Other Periodontal Problems and Oral Mal Odor".

Examples of prior art that appear to be best classified in this category also include U.S. patent applications: 20020049482 (Apr. 25, 2002 Fabian et al.) "Lifestyle Management System", 20040186528 (Sep. 23, 2004 Ries et al.) "Subcutaneous Implantable Medical Devices with Anti-Microbial Agents for Chronic Release", 20050146419 (Jul. 7, 2005 Porter) "Programmable Restricted Access Food Storage Container and Behavior Modification Assistant", 20050240253 (Oct. 27, 2005 Tyler et al.) "Systems and Methods for Altering Vestibular Biology", 20080141282 (Jun. 12, 2008 Elber et al.) "Control of Interactions Within Virtual Environments", 20080270947 (Oct. 30, 2008 Elber et al.) "Control of Interactions Within Virtual Environments", 20090197963 (Aug. 6, 2009 Llewellyn) "Method and Compositions for Suppressing Appetite or Treating Obesity", 20090312817 (Dec. 17, 2009 Hogle et al.) "Systems and Methods for Altering Brain and Body Functions and for Treating Conditions and Diseases of the Same", 20100055245 (Mar. 4, 2010 Havekotte et al.) "Modifying Flavor Experience Via Aroma Delivery", 20100291515 (Nov. 18, 2010 Pinnisi et al.) "Regulating Food and Beverage Intake", 20110314849 (Dec. 29, 2011 Park et al.) "Storage Container with Sensor Device and Refrigerator Having the Same", 20120009551 (Jan. 12, 2012 Pinnisi) "Cues to Positively Influence Eating Habits", 20120036875 (Feb. 16, 2012 Yun et al.) "Storage Container with Sensor Device and Refrigerator Having the Same", and 20120299723 (Nov. 29, 2012 Hafezi et al.) "Communication System Incorporated in a Container".

SUMMARY OF THIS INVENTION

This invention is a device and method for selectively and automatically reducing absorption of unhealthy food in a person's gastrointestinal tract, while allowing normal absorption of healthy food. This helps a person to lose weight without the deficiencies of essential nutrients that can occur with food-blind bariatric procedures and devices that indiscriminately reduce absorption of healthy food as well as unhealthy food.

In an example, such a device can comprise: a food-identifying sensor; an absorption-reducing substance; an implanted reservoir; and a release-control mechanism that selectively and automatically releases the substance into the person's gastrointestinal tract when the sensor detects that the person is consuming unhealthy food. In an example, such a device can comprise: a food-identifying sensor within the person's mouth or nose; and an absorption-reducing member that selectively and automatically reduces the absorption of food when the sensor detects that the person is consuming unhealthy food.

This novel invention addresses several limitations of the prior art in this field and provides a number of advantages for energy balance, weight management, and proper nutrition over the prior art. Further, its novel features are not anticipated by the prior art.

INTRODUCTION TO THE FIGURES

FIGS. 1 through 4 show an example of how this invention can be embodied in a device for selectively and automatically reducing absorption of nutrients from unhealthy food in the context of a longitudinal cross-sectional view of a person's torso.

FIGS. 1 and 2 show an example of how this invention can allow normal absorption of healthy food.

FIGS. 3 and 4 show an example of how this invention can selectively and automatically reduce absorption of nutrients from unhealthy food by coating the walls of a portion of the gastrointestinal tract.

FIGS. 5 and 6 show an example of how this invention can selectively and automatically reduce absorption of nutrients from unhealthy food by coating unhealthy food as it passes through the gastrointestinal tract.

FIGS. 7 and 8 show an example of how this invention can include a mouth-based sensor that triggers the release of a substance into a person's stomach in response to consumption of unhealthy food.

FIGS. 9 and 10 show an example of how this invention can include a mouth-based sensor that triggers electrical stimulation of a person's stomach in response to consumption of unhealthy food.

DETAILED DESCRIPTION OF THE FIGURES

FIGS. 1 through 10 show some examples of how this invention can be embodied in a device and method for selectively and automatically reducing absorption of nutrients from unhealthy food in a person's gastrointestinal tract. This can help a person to lose weight without the deficiencies of essential nutrients that can occur with food-blind procedures and devices in the prior art that indiscriminately reduce absorption of healthy food as well as unhealthy food. However, these figures are just some examples of how this invention can be embodied. They do not limit the full generalizability of the invention claims.

Figure 1:
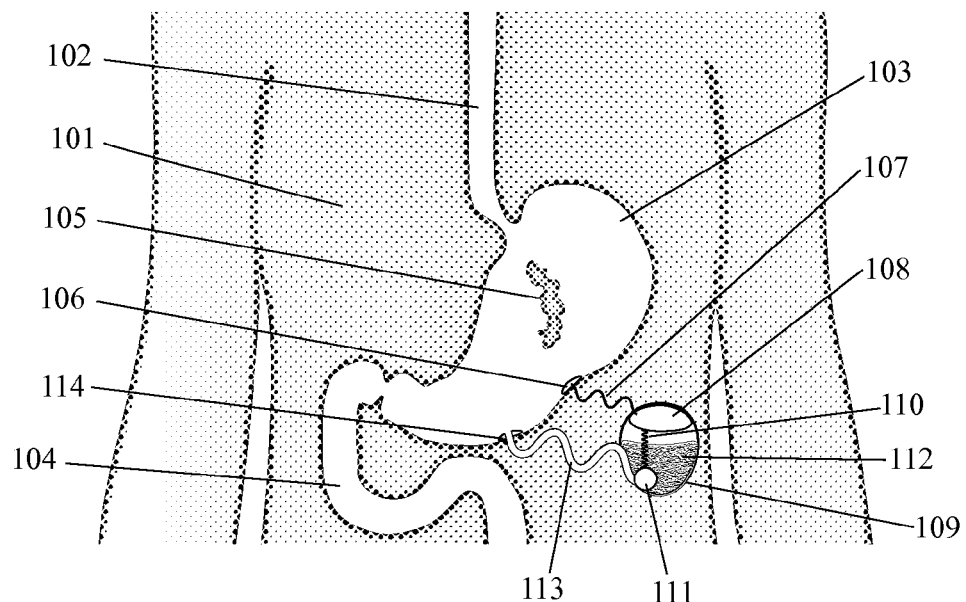
FIGS. 1 through 10 show some examples of how this invention can be embodied, but they do not limit the full generalizability of the claims.

FIG. 1 shows an example of how this invention can be embodied in a device for selectively and automatically reducing absorption of nutrients from unhealthy food in a person's gastrointestinal tract. FIG. 1 shows a longitudinal cross-sectional view of person's torso 101. This view includes a longitudinal cross-sectional view of a portion of the person's gastrointestinal tract comprising the esophagus 102, stomach 103, and duodenum 104. This figure also shows a bolus of food 105 in stomach 103 that the person has consumed. In FIG. 1, the bolus of food 105 is healthy food.

FIG. 1 also shows one embodiment of an implanted device for selective malabsorption of unhealthy food. Subsequent figures will provide sequential views showing how this device works to selectively and automatically reduce absorption of nutrients from unhealthy food, while allowing normal absorption of nutrients from healthy food. Selective malabsorption of unhealthy food, while allowing normal absorption of healthy food, can help a person to lose weight without suffering the deficiencies of essential nutrients that can be occur with food-blind bariatric procedures and malabsorption devices in the prior art.

As shown in the example, in FIG. 1, a food-identifying sensor 106 can be attached to the interior wall of stomach 103. Food-identifying sensor 106 can selectively and automatically detect when the person is consuming unhealthy food. In an example, food-identifying sensor 106 can perform intragastric chemical analysis to differentiate between consumption of unhealthy food versus healthy food. In an example, unhealthy food can be identified based on a high concentration of one or more of the following nutrients: sugars, simple sugars, simple carbohydrates, fats, saturated fats, cholesterol, and sodium.

In various examples, food-identifying sensor 106 can be selected from the group consisting of: chemical sensor, biochemical sensor, amino acid sensor, biological sensor, chemoreceptor, cholesterol sensor, chromatography sensor, EGG sensor, enzyme-based sensor, fat sensor, particle size sensor, peristalsis sensor, glucose sensor, impedance sensor, membrane-based sensor, Micro Electrical Mechanical System (MEMS) sensor, microfluidic sensor, micronutrient sensor, molecular sensor, motion sensor, nutrient sensor, osmolality sensor, pH level sensor, protein-based sensor, reagent-based sensor, and temperature sensor.

In the embodiment of this invention that is shown in FIG. 1, food-identifying sensor 106 is connected by wire 107 to a release-control mechanism 108 that is contained in an implanted reservoir 109. Release-control mechanism 108 is then connected by wire 110 to pump 111 which is also contained in reservoir 109. Pump 111 is in fluid communication with an absorption-reducing substance 112 that is contained in reservoir 109 until this substance is released into the stomach 103 through lumen 113 and one-way valve 114. Absorption-reducing substance 112 is released into the interior of the person's stomach 103 to reduce food absorption when food-identifying sensor 106 detects consumption of unhealthy food.

In an example, absorption-reducing substance 112 can comprise one or more ingredients that are Generally Recognized As Safe (GRAS) under Sections 201(s) and 409 of the Federal Food, Drug, and Cosmetic Act. In various examples, absorption-reducing substance 112 can comprise one or more ingredients selected from the group consisting of: psyllium, cellulose, avocado oil, castor oil, chitin, chitosan, beta-glucan, coconut oil, corn oil, flaxseed oil, olive oil, palm oil, safflower oil, soy oil, sunflower oil, gelatin, pectin, agar, guar gum, gum acacia, lignin, xantham gum, other insoluble fiber, other soluble fiber, other gum, and other vegetable oil.

In this embodiment, the sequence of action for this implanted device is as follows. First, a bolus of food 105 enters the stomach 103. Then, food-identifying sensor 106 detects whether food 105 is unhealthy using intragastric chemical analysis. If food 105 is unhealthy, then sensor 106 sends a signal through wire 107 to release-control mechanism 108. This signal triggers activation of pump 111 which releases absorption-reducing substance 112 through lumen 113 and one-way valve 114 into the stomach 103. After the absorption-reducing substance 112 is released into the stomach, the absorption-reducing substance 112 reduces absorption of nutrients from the bolus of unhealthy food 105 by coating the interior walls of the duodenum 104, by coating the bolus of food 105, or by a combination of both coating actions.

In an example, the absorption-reducing substance 112 can be used to selectively reduce absorption of nutrients from unhealthy food by temporarily coating a portion of the interior walls of the intestine when consumption of unhealthy food is detected. In an example, an absorption-reducing substance 112 can be used to selectively reduce absorption of nutrients from unhealthy food by coating the food, food particles, nutrients, and/or chyme in the gastrointestinal tract when consumption of unhealthy food is detected.

In an example, a release-control mechanism 108 can start releasing an absorption-reducing substance 112 into the person's stomach 103 in response to detection of consumption of unhealthy food by food-identifying sensor 106. In an example, a release-control mechanism 108 can stop releasing absorption-reducing substance 112 into the person's stomach 103 in response to detection of consumption of healthy food by the food-identifying sensor 106.

In an example, a release-control mechanism 108 can communicate wirelessly with a source external to the person's body. In an example, a release-control mechanism 108 can be programmed, or otherwise adjusted, to change the types of selected foods or nutrients to which it responds by releasing an absorption-reducing substance 112 into the person's gastrointestinal tract.

In various examples, a release-control mechanism 108 can be programmed to adjust one or more of the following aspects of its response to food-identifying sensor 106: the type of food which triggers decreased food absorption; the quantity of food which triggers decreased food absorption; the time of day, day of the week, or other timing parameter concerning food consumption which triggers decreased food absorption; the effect of the person's past food consumption on decreased food absorption; the effect of the person's caloric expenditure on decreased food absorption; and the effect of a personalized diet plan created for the person by a health care professional.

Figure 2:
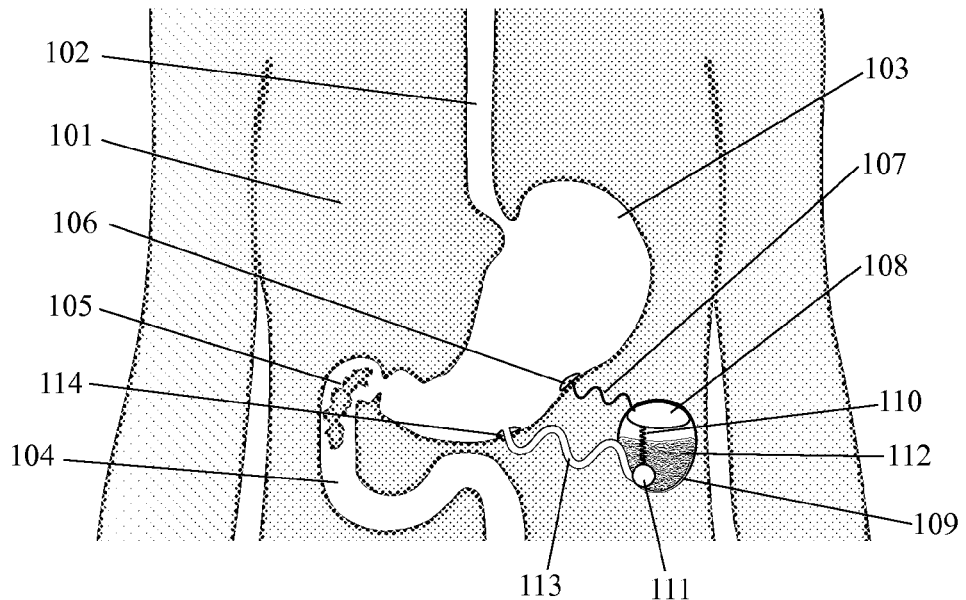

FIGS. 1 and 2 show how this embodiment of this invention can respond (or, more precisely, not respond) to a bolus of healthy food 105. These figures show that the device does not interfere with the normal absorption of healthy food 105. This is an advantage over malabsorption procedures and devices that blindly reduce absorption of all food, including healthy food. FIG. 1 shows a bolus of healthy food 105 that has entered the person's stomach 103. Food-identifying sensor 106 recognizes that bolus of food 105 is healthy, based on intragastric chemical analysis, and does not trigger any reduction in absorption of its nutrients. Accordingly, FIG. 2 shows bolus of food 105 (or a resulting bolus of chyme that contains particles of food 105) passing normally through the person's duodenum 104 for full nutrient absorption. This avoids the deficiencies of essential nutrients that can be caused by food-blind malabsorption procedures and devices in the prior art.

Figure 3:
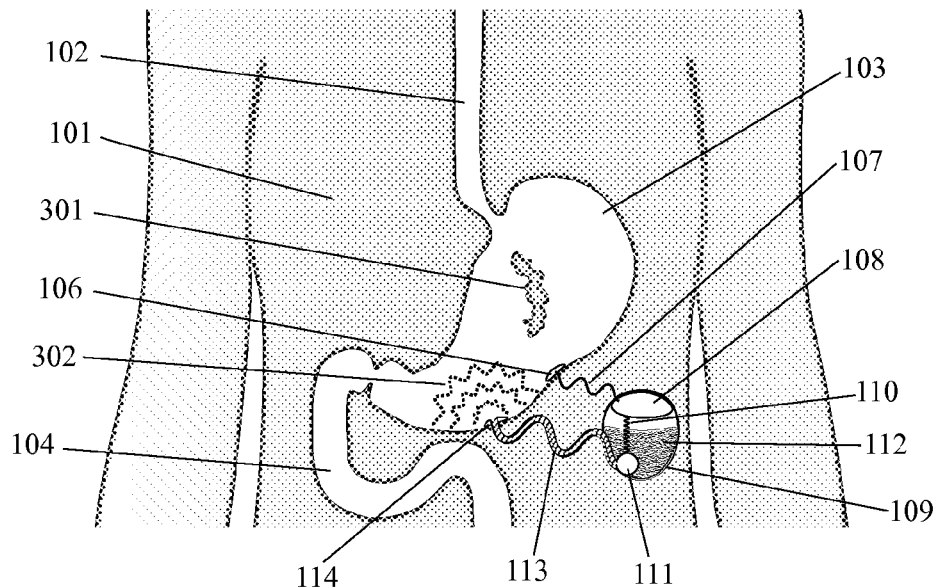
Figure 4:
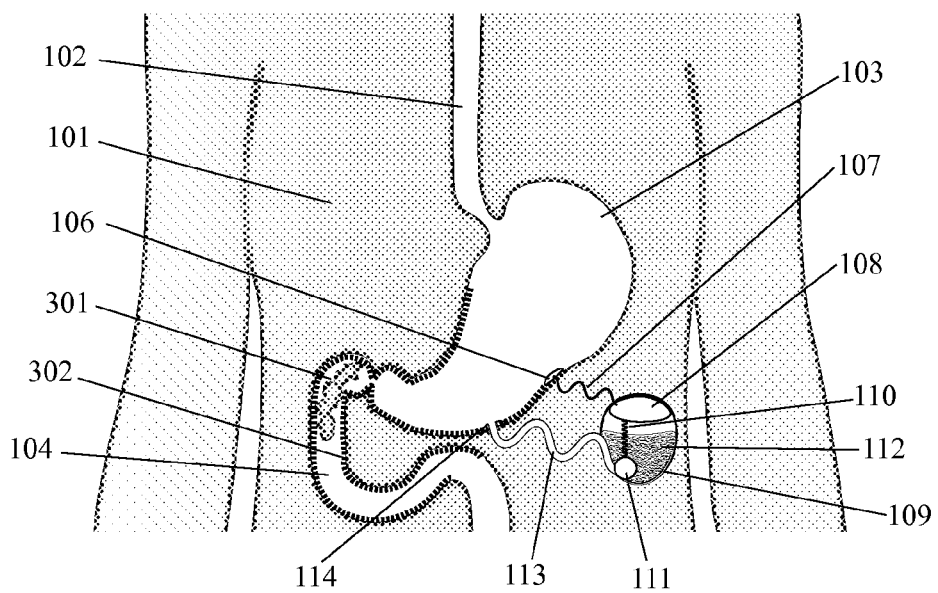

FIGS. 3 and 4 show how this embodiment can selectively and automatically respond to a bolus of unhealthy food 301. In FIG. 3, a bolus of unhealthy food 301 has entered the person's stomach 103. The bolus of unhealthy food 301 is identified as unhealthy by food-identifying sensor 106. In an example, this identification can be done using intragastric chemical analysis. Next, sensor 106 sends a signal indication, via wire 107, that the person has consumed unhealthy food 301 to release-control mechanism 108. Then, release-control mechanism 108 activates pump 111 to release a quantity of the absorption-reducing substance 112, through lumen 113 and one-way valve 114, into the interior of stomach 103. The release of the absorption-reducing substance 112 into stomach 103 is represented by concentric wavy dotted lines 302 that radiate outwards from one-way valve 114 into the interior of the person's stomach 103.

FIG. 4 shows an example of what can happen when the absorption-reducing substance 112 is released into the person's stomach 103. In this example, the absorption-reducing substance 112 temporarily coats the lower portion of person's stomach 103 and, more importantly for malabsorption of nutrients, the absorption-reducing substance 112 also coats the interior walls of the person's duodenum 104. This temporary coating action is represented in FIG. 4 by thick dashed lines 302 on the interior surface of the person's lower stomach 103 and on the interior walls of the person's duodenum 104. In this example, coating 302 on the walls of the duodenum reduces absorption of nutrients from the bolus of unhealthy food 301 (or a resulting bolus of chyme that contains particles of food 301) as this bolus passes through the duodenum.

In an example, this temporary reduction in nutrient absorption occurs because of an increase in the speed or motility with which a bolus of food 301 passes through the duodenum 104. In an example, this temporary reduction in nutrient absorption can occur because of a temporary decrease in the nutrient permeability of the mucus that covers the interior walls of the duodenum 104. In an example, this temporary reduction in nutrient absorption can occur because the absorption-reducing substance temporarily binds to the nutrient-absorbing organelles along the interior walls of the duodenum 104. The temporary nature of this duodenal coating is important because it allows the duodenum 104 to return to normal absorption status for later consumption and absorption of healthy food. This is a significant improvement over food-blind procedures and devices in the prior art that cause permanent and indiscriminant malabsorption of all types of food.

Figure 5:
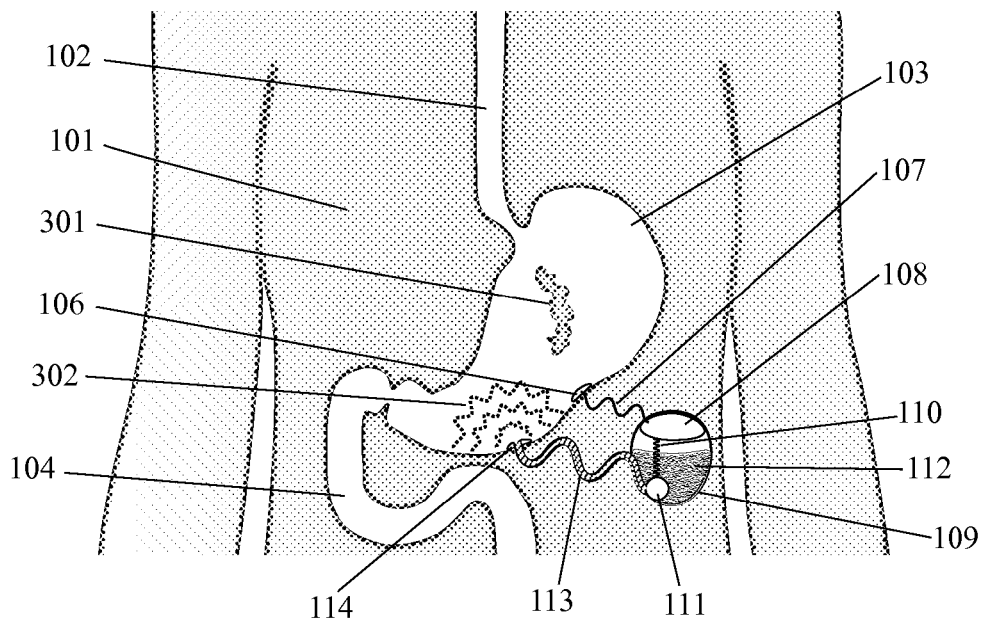
Figure 6:
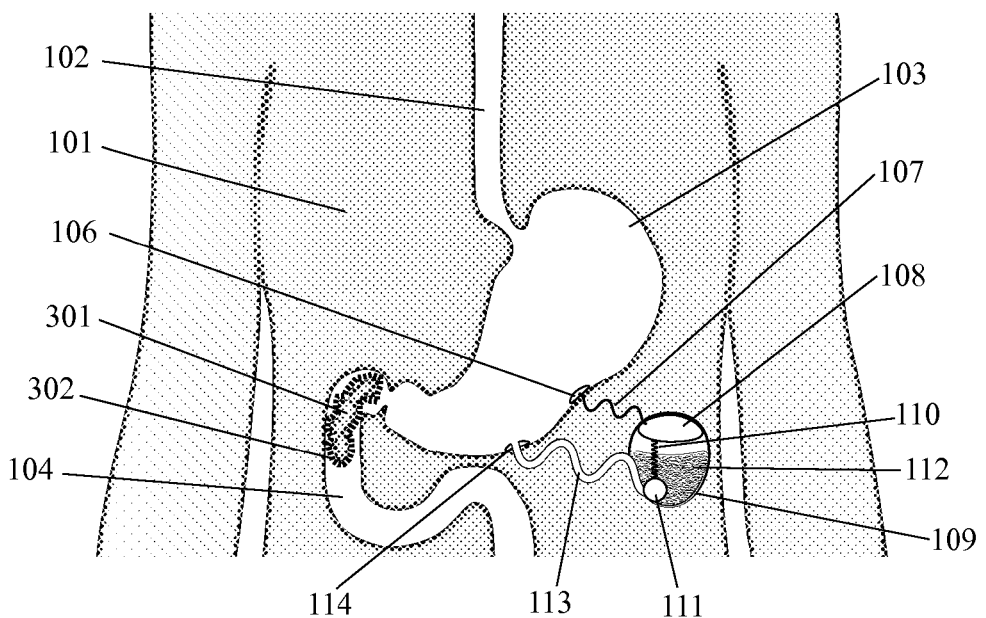

FIGS. 5 and 6 show another example of how this embodiment can selectively and automatically reduce absorption of a bolus of unhealthy food 301. As was the case in FIG. 3, FIG. 5 shows that a bolus of unhealthy food 301 has entered stomach 103. Also, as shown in FIG. 3, FIG. 5 shows that the food-identifying sensor 106 identifies that bolus of food 301 is unhealthy. In an example, this identification is done using intragastric chemical analysis. Identification of bolus of food 301 as being unhealthy triggers release-control mechanism 108. This, in turn, activates pump 111 which releases absorption-reducing substance 112 into the person's stomach 103. The release of absorption-reducing substance 112 into stomach 103 is again represented by wavy dotted lines 302 which radiate outwards from one-way valve 114 into the stomach interior 103.

FIG. 6 is similar to FIG. 4, except that now the absorption-reducing substance 112 coats the surface of bolus of food 301 instead of the interior walls of duodenum 104. This coating action is represented in FIG. 6 by thick dashed lines 302 around the perimeter of bolus of food 301 (or the resulting bolus of chyme that contains particles of food 301) as it passes through the duodenum. In an example, reduced absorption of nutrients from bolus of food 301 can occur because of an increase in the speed at which this bolus of food 301 passes through duodenum 104. In an example, reduced absorption of nutrients from this bolus of food 301 can occur because the coating around the bolus prevents nutrients in the bolus from coming into contact with the nutrient-absorbing organelles along the interior walls of duodenum 104.

In this example, with the bolus having been coated instead of the walls of the duodenum, the duodenum is able to normally and fully absorb nutrients from any subsequent bolus of healthy food that comes down the gastrointestinal tract. This is a significant improvement over food-blind procedures and devices in the prior art that cause permanent and indiscriminant malabsorption of all types of food.

FIGS. 1 through 6 show some examples of how this invention can be embodied in a device for selectively and automatically reducing the absorption of selected types of food in a person's gastrointestinal tract. This device comprises: (a) a food-identifying sensor 106 that selectively detects when the person is consuming and/or digesting selected types of food; (b) an absorption-reducing substance 112 that is released into the interior of the person's gastrointestinal tract to temporarily reduce absorption of nutrients from food by the gastrointestinal tract; (c) an implanted reservoir 109 that contains a quantity of the absorption-reducing substance, wherein this reservoir is configured to be implanted within the person's body and wherein there is an opening or lumen through which the absorption-reducing substance is released from the reservoir into the interior of a portion of the person's gastrointestinal tract; and (d) a release-control mechanism 108 that controls the release of the absorption-reducing substance from the reservoir into the person's gastrointestinal tract, wherein this release-control mechanism can selectively and automatically increase the release of the absorption-reducing substance when the food-identifying sensor detects that the person is consuming and/or digesting selected types of food. I will now discuss each of these four components in greater detail.

I will first discuss the food-identifying sensor in greater detail. In an example, a food-identifying sensor can selectively detect consumption and/or digestion of selected types of food. In an example, food identification can occur as food is entering, or being consumed within, a person's mouth. In an example, food identification can occur as food is passing through, and being digested within, a person's stomach or another portion of a person's gastrointestinal tract. In an example, a food-identifying sensor can selectively detect consumption and/or digestion of unhealthy food. In an example, a food-identifying sensor can selectively discriminate between consumption and/or digestion of unhealthy types or quantities of food versus consumption and/or digestion of healthy types or quantities of food.

In an example, a food-identifying sensor can selectively detect consumption or digestion of unhealthy foods as identified by their having a high concentration or large amount of selected nutrients. In an example, there can be a predefined list of types of food which are classified as unhealthy. In an example, there can be predefined quantities of selected types of food which are classified as unhealthy. In an example, there can be a predefined list of types of food which are classified as healthy. In an example, there can be predefined quantities of selected types of food which are classified as healthy. In an example, lists of the types and quantities of food which are classified as unhealthy or healthy can be compiled and adjusted by experts and professionals who provide the person with nutritional and dietary counseling.

In an example, a food-identifying sensor can selectively detect consumption or digestion of unhealthy food based on their having a high concentration or large amount of nutrients selected from the group consisting of: sugars, simple sugars, simple carbohydrates, fats, saturated fats, fat cholesterol, and sodium. In an example, such a sensor can selectively detect consumption or digestion of foods with a high concentration or quantity of cholesterol. In various examples, a food-identifying sensor can selectively detect consumption and/or digestion of one or more selected types of foods selected from the group consisting of: fried food, high-cholesterol food, high-fat food, high-sugar food, and high-sodium food.

In an example, a food-identifying sensor can selectively detect when a person is consuming or digesting unhealthy types of food and can selectively detect when a person is consuming or digesting healthy types of food. In an example, a food-identifying sensor can selectively differentiate between consumption of unhealthy versus healthy food. In an example, unhealthy food can be identified as having a relatively large amount of sugars, simple carbohydrates, fats, saturated fats, cholesterol, and/or sodium. In an example, unhealthy food can be identified as having a relatively large number of grams of carbohydrates or simple carbohydrates, grams of fats or saturated fats, and/or milligrams of sodium per serving.

In an example, healthy food can be identified in a negative manner, as any food that is not identified as being unhealthy. In an alternative example, healthy food can be identified in a positive manner, as any food with a large concentration or amount of one or more nutrients selected from the group consisting of: food with a lot of soluble fiber, food with a lot of insoluble fiber, food with a lot of essential vitamins, and food with a high concentration of essential nutrients that the person's diet generally lacks.

In various examples, an unhealthy type of food can be identified as being in the group consisting of: fried or deep-fried food, French fries, high-cholesterol food, high-fat food or high-saturated-fat food, food with a high amount of high-fructose corn syrup, high-sodium food, food with a high amount of simple or refined sugar or high-sugar food, food with a high amount of hydrogenated oil, and non-diet soda pop. In an example, a food-identifying sensor can selectively detect when a person is consuming or digesting food that has: at least a selected number of grams of fats per serving, at least a selected number of grams of saturated fats per serving, at least a selected number of milligrams of fat cholesterol per serving, at least a selected number of grams of carbohydrates per serving, and/or at least a selected number of milligrams of sodium per serving. In an example, quantities of food exceeding one or more of these amounts can be automatically classified as unhealthy.

In a variation on this example, serving size for the purposes of food identification can be based on suggested serving sizes and/or population norms. For example, a food-identifying sensor can selectively detect when a person is consuming or digesting food that has: at least a selected number of grams of fats per suggested serving, at least a selected number of grams of saturated fats per suggested serving, at least a selected number of milligrams of fat cholesterol per suggested serving, at least a selected number of grams of carbohydrates per suggested serving, and/or at least a selected number of milligrams of sodium per suggested serving.

In an example, a food-identifying sensor can selectively detect consumption or digestion of food that comprises over: a selected number of grams of fat per suggested serving, a selected number of grams of saturated fat per suggested serving, a selected number of milligrams of fat cholesterol per suggested serving, a selected number of grams of carbohydrate per suggested serving, and/or a selected number of milligrams of sodium per suggested serving. In an example, quantities of food exceeding one or more of these amounts can be automatically classified as unhealthy.

In another example, serving size for the purposes of food identification can be based on a person's past eating habits and/or the actual quantity of food that a person is consuming, in real time, during an eating episode. In an example, an eating episode can be defined as a period of time with continuous eating. In an example, an eating episode can be defined as a period of time with less than a selected amount of time between mouthfuls and/or swallows.

In an example, a food-identifying sensor can selectively detect when a person is consuming or digesting food that has: at least a selected number of grams of fats per actual serving, at least a selected number of grams of saturated fats per actual serving, at least a selected number of milligrams of fat cholesterol per actual serving, at least a selected number of grams of carbohydrates per actual serving, and/or at least a selected number of milligrams of sodium per actual serving. In an example, quantities of food exceeding one or more of these amounts can be automatically classified as unhealthy.

In an example, a food-identifying sensor can selectively detect when a person is consuming or digesting food that has: at least a selected number of grams of fats per eating episode, at least a selected number of grams of saturated fats per eating episode, at least a selected number of milligrams of fat cholesterol per eating episode, at least a selected number of grams of carbohydrates per eating episode, and/or at least a selected number of milligrams of sodium per eating episode. In an example, quantities of food exceeding one or more of these selected amounts can be automatically classified as unhealthy.

In an example, a food-identifying sensor can enable selective detection of cumulative consumption of food during a period of time that totals: at least a selected number of grams of fats, at least a selected number of grams of saturated fats, at least a selected number of milligrams of fat cholesterol, at least a selected number of grams of carbohydrates, and/or at least a selected number of milligrams of sodium. In an example, a food-identifying sensor can enable selective detect of cumulative consumption of food during a period of time that totals: at least a predetermined amount of fat, at least a predetermined amount of saturated fat, at least a predetermined amount of fat cholesterol, at least a predetermined amount of carbohydrates, and/or at least a predetermined amount of sodium. In an example, quantities of food exceeding one or more of these amounts can be automatically classified as unhealthy.

In another variation on these examples, the amount of selected nutrients in a specific type of food can be evaluated as a percentage of the recommended daily intake for such a nutrient. For example, a food-identifying sensor can selectively detect consumption or digestion of food that comprises at least: a selected percentage of the recommended daily intake of fat per suggested serving, a selected percentage of the recommended daily intake of saturated fat per suggested serving, a selected percentage of the recommended daily intake of fat cholesterol per suggested serving, a selected percentage of the recommended daily intake of carbohydrate per suggested serving, and/or a selected percentage of the recommended daily intake of sodium per suggested serving. In an example, quantities of food exceeding one or more of these recommended amounts can be automatically classified as unhealthy.

In an example, food identification can occur as food is being consumed, and beginning to be digested, within a person's mouth. In an example, a food-identifying sensor can detect a selected type of food by analyzing the composition of the person's saliva as that food is being digested in a person's mouth. In an example, a food-identifying sensor can be a chemical sensor that uses chemical analysis to identify particular types of food and/or nutrients. In an example, a food-identifying sensor can analyze the composition of the person's saliva in order to automatically and selectively detect when a person is digesting a food that is high in (simple) sugar or (saturated) fat, while that food is being digested within the person's mouth.

In various examples, a food-identifying sensor which is in fluid communication with a person's oral or nasal cavity can identify food as being unhealthy based on one or more methods selected from the group consisting of: chemical analysis of food as it begins to be digested within a person's mouth; olfactory analysis of food as it beings to be digested within a person's mouth; image analysis of images of food as it approaches the person's mouth; sonic analysis of chewing or swallowing as food is consumed; and analysis of signals from nerves that innervate a person's taste buds and/or olfactory receptors.

There are a number of different types of sensors that can be used to identify a selected type of food and/or a selected quantity of that food. In an example, a food-identifying sensor can be a chemical sensor. In various examples, a chemical sensor can detect the amount or concentration of sugars, simple carbohydrates, fats, saturated fats, cholesterol fat, and/or sodium in food while it is being consumed or digested by a person.

In various examples, a food-identifying sensor can be selected from the group consisting of: chemical sensor, biochemical sensor, accelerometer, amino acid sensor, biological sensor, camera, chemoreceptor, cholesterol sensor, chromatography sensor, electrogastrogram sensor, electrolyte sensor, electromagnetic sensor, EMG sensor, enzymatic sensor, fat sensor, flow sensor, particle size sensor, peristalsis sensor, genetic sensor, glucose sensor, imaging sensor, impedance sensor, interferometer, medichip, membrane-based sensor, Micro Electrical Mechanical System (MEMS) sensor, microfluidic sensor, micronutrient sensor, molecular sensor, motion sensor, muscle activity sensor, nanoparticle sensor, neural impulse sensor, optical sensor, osmolality sensor, pattern recognition sensor, pH level sensor, pressure sensor, protein-based sensor, reagent-based sensor, sound sensor, strain gauge, and temperature sensor.

In various examples, a food-identifying sensor can be located in any location from which it is in fluid and/or gaseous communication with food that the person is consuming or digesting. In an example, a food-identifying sensor can be implanted within a person's body. An implanted sensor is generally less dependent on voluntary action by the person than an external sensor. For example, an implanted sensor can operate in an automatic manner, regardless of the person's behavior. In contrast, an external sensor, such as a picture-taking mobile electronic device or a wearable electronic imaging device can be forgotten, obscured, or just plain unused. An implanted food-identifying sensor is less prone to compliance or circumvention problems than an external sensor. In various examples, an implanted food-identifying sensor can be attached to, or implanted within, the person's body by one or more means selected from the group consisting of: suture, staple, adhesive, glue, clamp, clip, pin, snap, elastic member, tissue pouch, fibrotic tissue, screw, and tissue anchor.

In an example, an implanted food-identifying sensor can be configured to be attached to, or implanted within, a person's stomach. In an example, a food-identifying sensor can detect digestion of selected types of food within a person's stomach. In another example, a food-identifying sensor can be configured to be attached to, or implanted within, a portion of a person's intestine. In an example, a food-identifying sensor can detect digestion of selected types of food within a person's intestine. In various examples, an implanted food-identifying sensor can be configured to be attached to, or implanted within, a person's stomach, duodenum, jejunum, ileum, caecum, colon, or esophagus. In various examples, a food-identifying sensor can be configured to be implanted within a person's abdominal cavity with a means of fluid, neural, or other communication with the person's stomach, duodenum, jejunum, ileum, caecum, colon, or esophagus.

In another example, a food-identifying sensor can be located closer to the initial point of food consumption, such as in a person's mouth or nose. In an example, an implanted food-identifying sensor can be configured to be attached to, implanted within, or otherwise in fluid communication with a person's mouth. In an example, an implanted food-identifying sensor can be configured to be attached to, implanted within, or otherwise in fluid communication with a person's nose.

One advantage of having a food-identifying sensor that is in fluid communication with a person's oral or nasal cavity is that it can identify consumption of a particular bolus of food sooner than a sensor that is in fluid communication with the person's stomach. This can allow time for modification of the person's stomach or intestinal walls before the bolus of food arrives. In an example, a food-identifying sensor in a person's mouth or nose can be in wireless communication with an absorption-reducing member in the person's stomach or intestine.

In an example, a mouth or nose based food-identifying sensor can provide "earlier detection" that a bolus of unhealthy food will be coming down the esophagus into the stomach and intestine. In an example, such advance notice (from a mouth-based sensor) can enable coating the walls of the duodenum with an absorption-reducing coating before a certain bolus of food arrives there. As another example, such advance notice (from a mouth-based sensor) can enable releasing a food-coating substance in the stomach before a certain bolus of food moves down the esophagus to enter the stomach. These actions can more efficiently reduce absorption of a particular bolus of food as it moves through a person's gastrointestinal tract.

In an example, a food-identifying sensor can be configured to be attached to, or implanted within, a person's oral cavity, a person's nasal cavity, or tissue surrounding one of these cavities. In various examples, such a sensor can be configured to be attached to, or implanted within, the person's hard palate, palatal vault and/or upper mouth roof, teeth, tongue, or soft palate. In an example, such a food-identifying sensor can detect consumption or digestion of unhealthy food within the person's mouth.

In an example, a food-identifying sensor can be configured to be implanted in a subcutaneous site or an intraperitoneal site. In an example, a food-identifying sensor can be configured to be attached to a nerve. In an example, a food-identifying sensor can be in communication with a nerve that is connected to the stomach. In an example, a food-identifying sensor can be configured to be implanted in adipose tissue or muscular tissue.

There are advantages to having a food-identifying sensor be implanted in a person's body. For example, having a sensor be implanted can make a sensor more automatic in nature and less susceptible to non-compliance, manipulation, or circumvention. However, there can also be advantages to having a food-identifying sensor be external to the person's body. As one advantage of an external sensor, an external sensor can be less invasive and/or costly than an implanted sensor. As a second potential advantage, an external sensor can detect food consumption earlier than a sensor in a person's mouth or nose. For example, an external food-identifying sensor can identify food as person reaches for it, as the person brings it up to their mouth, or as the person inserts it into their mouth. As a third potential advantage of an external sensor, some forms of food identification (especially image analysis) are easier when performed on food before it is inserted into a person's mouth.

In an example, an external food-identifying sensor can be in wireless communication with an internal absorption-reducing implant. This allows the internal absorption-reducing implant to be selectively activated when the person consumes unhealthy food, but still allow normal absorption of nutrients from healthy food. In an example, a food-identifying sensor can be worn externally on the person's body and be in wireless communication with an implanted member that selectively modifies food absorption.

In an example, a food-identifying sensor can be incorporated into a mobile electronic device, such as a cell phone, mobile phone, or tablet that is carried by the person. In an example, an external sensor can be in wireless communication with an implanted member that selectively modifies consumption of a given bolus of food in order to reduce absorption of unhealthy food and allow normal absorption of healthy food. In an example, an external sensor, or a mobile device of which this sensor is an application or component, can communicate with the internet and/or other mobile devices.

In an example, a food-identifying sensor can be part of a piece of electronically-functional jewelry that is worn by a person. In an example, a food-identifying sensor can be worn on a body member selected from the group consisting of: wrist, hand, finger, arm, torso, neck, head, and ear. In an example, an external food-identifying sensor can be incorporated into a piece of electronically-functional jewelry selected from the group consisting of electronically-functional: necklace, pendant, finger ring, bracelet, nose ring, and earring. In an example, an external food-identifying sensor can be incorporated into an electronically-functional wrist watch, pair of eyeglasses, or hearing aid. In an example, an external sensor, or piece of electronically-functional jewelry of which this sensor is a part, can communicate with the internet and/or other people via other electronic communication means.

I will now discuss the absorption-reducing substance in greater detail. In an example, an absorption-reducing substance can have the property that it reduces absorption of nutrients from food in a person's gastrointestinal tract when this substance is released directly into the person's gastrointestinal tract. In an example, an absorption-reducing substance can reduce absorption of nutrients by temporarily coating the walls of a portion of the person's intestines. In an example, such a substance can reduce absorption of nutrients by selectively coating a particular bolus of food, food particles, or chyme as it moves through the person's gastrointestinal tract. In an example, this substance can coat the walls of a person's intestine and coat a selected bolus of food.

In an example, an absorption-reducing substance can have a local and temporary absorption-reducing effect that allows selective reduction of the absorption of a particular bolus of food. In an example, this selective absorption-reducing effect can be used to selectively reduce absorption of nutrients from unhealthy types and/or quantities of food, while allowing normal absorption of nutrients from healthy types and/or quantities of food. This is an improvement over systemic drugs that have an indiscriminant effect on appetite or food absorption that blindly affect absorption of nutrients from healthy as well as unhealthy food. This is also an improvement over surgical procedures and malabsorption devices in the prior art that blindly reduce absorption of nutrients from healthy food as well as unhealthy food.

In an example, an absorption-reducing substance can be released directly into a person's gastrointestinal tract from an implanted reservoir in order to reduce absorption of nutrients from a selected bolus of unhealthy food. In an example, the food consumed may be of an unhealthy type and/or quantity. It is advantageous for absorption reduction to be temporary so that the substance can be used to selectively reduce food absorption only when the person consumes a bolus of unhealthy food, but still allow normal absorption of nutrients from healthy food. This can help to avoid a deficit of healthy nutrients that can sometimes occur with permanent absorption-reducing methods such as permanent bariatric surgery.

In an example, an absorption-reducing substance can work by creating a coating between a bolus of food and the walls of the gastrointestinal tract. In an example, this coating can reduce fluid communication between food and the walls. In an example, this coating can increase the speed at which food travels through a portion of the gastrointestinal tract. In an example, this coating can coat food (or food particles or chyme) so that nutrients in the food do not come into contact with the walls of the intestine. In another example, this coating can be on the walls of the intestine itself, so that the nutrient-absorbing organelles on the intestinal wall are temporarily blocked from absorbing nutrients from food. In an example, both the food and the walls can be coated.

In various examples, an absorption-reducing substance can be released into the gastrointestinal tract to coat food, food particles, nutrients, or chyme in the gastrointestinal tract. In various examples, an absorption-reducing substance can coat food, food particles, nutrients, or chyme in the gastrointestinal tract in order to increase or decrease the speed at which the coated material moves through the gastrointestinal tract. In various examples, an absorption-reducing substance can coat food, food particles, nutrients, or chyme in the gastrointestinal tract to decrease fluid communication between food in the gastrointestinal tract and the walls of the gastrointestinal tract.

In an example, an absorption-reducing substance can coat a portion of the interior walls of the duodenum or another portion of the intestine. In an example, an absorption-reducing substance can coat, cover, or block the nutrient-absorbing organelles that are located on the walls of a portion of the intestine. In an example, this coating, covering, or blocking action can be temporary. This coating, covering, or blocking action can be timed in advance of the arrival of a bolus of unhealthy food in the intestine so that malabsorption of food is selectively targeted at unhealthy food. Ideally, the adsorption-reducing coating, covering, or blocking action is such that it can wear off by the time that a bolus of healthy food enters the gastrointestinal tract. However, even if there is a lag between when a bolus of unhealthy food passes through the gastrointestinal tract and when the absorption-reducing effect wears off, this device and method can still be superior for absorption of nutrients from healthy food as compared to devices and methods in the prior art that uniformly and indiscriminately reduce absorption of all food.

In an example, an absorption-reducing substance can coat a portion of the interior walls of the gastrointestinal tract in order to increase or decrease the speed at which food moves through the gastrointestinal tract. In an example, an absorption-reducing substance can coat a portion of the interior walls of the gastrointestinal tract in order to decrease fluid communication between food in the gastrointestinal tract and the walls of the gastrointestinal tract. In an example, an absorption-reducing substance can temporarily coat a portion of the interior walls of the duodenum, of another portion of the intestine, or of another portion of the gastrointestinal tract.

In an example, an absorption-reducing substance can temporarily coat or block nutrient-absorbing organelles on a portion of the interior walls of the gastrointestinal tract. In an example, an absorption-reducing substance can temporarily coat a portion of the interior walls of the gastrointestinal tract to increase the speed at which food moves through the gastrointestinal tract. In an example, an absorption-reducing substance can temporarily coat a portion of the interior walls of the gastrointestinal tract to decrease fluid communication between food in the gastrointestinal tract and the walls of the gastrointestinal tract.

In an example, an absorption-reducing substance that is released into the gastrointestinal tract can mechanically, chemically, or biologically bind to, or adhere to, material or tissue in the gastrointestinal tract in order to reduce absorption of food. For example, an absorption-reducing substance can bind to, or adhere to, food, food particles, nutrients, or chyme in the gastrointestinal tract. In an example, an absorption-reducing substance can isolate food, food particles, nutrients, or chyme in the gastrointestinal tract to increase or decrease the speed at which this material moves through the gastrointestinal tract. In an example, an absorption-reducing substance can bind to, or adhere to, food, food particles, nutrients, or chyme in the gastrointestinal tract in order to decrease fluid communication between food nutrients in the gastrointestinal tract and the walls of the gastrointestinal tract.

In an example, an absorption-reducing substance can mechanically, chemically, or biologically bind to, or adhere to, a portion of the interior walls of the duodenum or another portion of the intestine. In an example, an absorption-reducing substance can temporarily bind or adhere to a portion of the interior walls of the gastrointestinal tract. In an example, an absorption-reducing substance can bind to, or adhere to, nutrient-absorbing organelles on a portion of the interior walls of the gastrointestinal tract. Such binding or adhering action can reduce the ability of these organelles to absorb nutrients from a selected bolus of unhealthy food passing through the gastrointestinal tract. When such binding or adhering action is temporary, the body can still absorb required nutrients from a bolus of healthy food consumed some time after the bolus of unhealthy food has passed.

In an example, an absorption-reducing substance can bind to, or adhere to, a portion of the interior walls of the gastrointestinal tract in order to increase or decrease the speed at which food moves through the gastrointestinal tract. In an example, an absorption-reducing substance can have a laxative effect on a bolus of unhealthy food. This laxative effect can reduce unhealthy food absorption by reducing the duration of contact between the unhealthy food and the walls of the duodenum.

In an example, an absorption-reducing substance can temporarily bind to, or adhere to, a portion of the interior walls of the gastrointestinal tract in order to decrease fluid communication between food in the gastrointestinal tract and the walls of the gastrointestinal tract. When this temporary coating is timed in advance of a bolus of unhealthy food, then it can selectively reduce absorption of nutrients from unhealthy food. In an example, an absorption-reducing substance can temporarily block or otherwise disable nutrient-absorbing organelles on a portion of the interior walls of the person's duodenum or another portion of the person's intestine.

In an example, an absorption-reducing substance can work by affecting the mucus that covers the walls of the person's duodenum. In an example, the absorption-reducing substance can temporarily increase the thickness of the mucus on a portion of the interior walls of the person's duodenum. In an example, the absorption-reducing substance can temporarily increase the viscosity of the mucus on a portion of the interior walls of the person's duodenum. This increased thickness or viscosity can temporarily decrease fluid communication between nutrients in a selected bolus of food (or chyme) and the walls of the duodenum. In another example, the absorption-reducing substance can temporarily decreases the nutrient permeability of the mucus on a portion of the interior walls of the person's duodenum or another portion of the intestine. This decreased permeability can decrease the absorption of nutrients by the body from a bolus of unhealthy food moving through the person's gastrointestinal tract.

In various examples, an absorption-reducing substance can reduce absorption of food in the gastrointestinal tract by one or more means selected from the group consisting of: forming a temporary coating on the walls of the duodenum or another portion of the intestine; forming a coating on food or chyme in the gastrointestinal tract; forming a temporary coating on the walls of the intestine to reduce fluid communication between food or chyme in the gastrointestinal tract and the gastrointestinal tract walls; forming a coating on food or chyme in the gastrointestinal tract to reduce fluid communication between food or chyme in the gastrointestinal tract and the gastrointestinal tract walls.

In various examples, an absorption-reducing substance can reduce absorption of food in the gastrointestinal tract by one or more means selected from the group consisting of: forming a temporary coating on the walls of the intestine to increase the speed of food or chyme moving through the gastrointestinal tract; forming a coating on food or chyme moving through the gastrointestinal tract in order to increase the speed of food or chyme moving through the gastrointestinal tract; temporarily binding to the nutrient-absorbing organelles on the interior walls of a portion of the intestine; binding to food or chyme moving through the gastrointestinal tract; temporarily increasing the viscosity of the mucus that coats the interior walls of the duodenum or another portion of the intestine; temporarily decreasing the nutrient permeability of the mucus that coats the interior walls of the duodenum or another portion of the intestine; and temporarily covering or blocking the nutrient-absorbing organelles of the duodenum or another portion of the intestine.

In an example, a quantity of an absorption-reducing substance can be stored in an implanted reservoir. In an example, this substance may be stored in a liquid or gel form. In an example, this substance may be released into the person's gastrointestinal tract by an active pumping or spraying action. In an example, an absorption-reducing substance can be a liquid that coats material or tissue surfaces in the interior of a person's gastrointestinal tract when it is released into the interior of that tract. In an example, a quantity of an absorption-reducing substance can be stored in an implanted reservoir in a powder or solid form and then released into the person's gastrointestinal tract. In various examples, an absorption-reducing substance can be stored in reservoir and/or released into the gastrointestinal tract in a form selected from the group consisting of: liquid, emulsion, erodible formulation, gel, granules, microspheres, capsule, powder, semi-solid, solid, spray, and suspension.

In an example, an absorption-reducing substance can create a lubricious coating that temporarily separates food or food particles in the gastrointestinal tract from fluid communication with the walls of the gastrointestinal tract. In an example, an absorption-reducing substance can create a temporary nutrient barrier that temporarily isolates nutrients in food passing through the gastrointestinal tract from the nutrient-absorbing organelles along the walls of the gastrointestinal tract. In an example, an absorption-reducing substance can reduce absorption of food for a limited period of time after being released into the gastrointestinal tract.

In an example, an absorption-reducing substance can comprise one or more ingredients that are Generally Recognized As Safe (GRAS) under Sections 201(s) and 409 of the Federal Food, Drug, and Cosmetic Act. In an example, an absorption-reducing substance can comprise a composition with insoluble fiber. In an example, an absorption-reducing substance can comprise a composition with soluble fiber. In an example, an absorption-reducing substance can beneficially coat the walls of a portion of the intestine in order to reduce the body's absorption of fats. In various specific examples, an absorption-reducing substance can comprise one or more ingredients that are selected from the group consisting of: psyllium, cellulose, avocado oil, castor oil, chitin, chitosan, beta-glucan, coconut oil, corn oil, flaxseed oil, olive oil, palm oil, safflower oil, soy oil, sunflower oil, gelatin, pectin, agar, guar gum, gum acacia, lignin, xantham gum, other insoluble fiber, other soluble fiber, other gum, and other vegetable oil.

In other specific examples, an absorption-reducing substance can comprise one or more ingredients that are selected from the group consisting of: acai oil, agar, almond oil, amaranth oil, apple seed oil, apricot oil, argan oil, avocado oil, babassu oil, beech nut oil, beta-glucan, bitter gourd oil, black pepper oil, black seed oil, blackcurrant seed oil, borage seed oil, bottle gourd oil, buffalo gourd oil, camellia oil, canola oil, carob oil, cashew oil, castor oil, cellulose, chitin, chitosan, cinnamon oil, citrus oil, clove oil, cocklebur oil, coconut oil, cod liver oil, cohune oil, colza oil, coriander seed oil, corn oil, cottonseed oil, date seed oil, dika oil, egg yolk oil, eucalyptus oil, false flax oil, fennel oil, fish oil, flaxseed oil, garlic oil, gelatin, ginger oil, grape seed oil, grapefruit seed oil, guar gum, gum acacia, hazelnut oil, hemp oil, kapok seed oil, kenaf seed oil, lactulose, lallemantia oil, lemon oil, lignin, lime oil, linseed oil, macadamia oil, mafura oil, marula oil, menthol oil, mineral oil, and mint oil.

In other specific examples, an absorption-reducing substance can comprise one or more ingredients that are selected from the group consisting of: mongongo nut oil, mustard oil, nutmeg oil, okra seed oil, olive oil, olive oil, orange oil, palm oil, papaya seed oil, peanut oil, pecan oil, pectins, pepper oil, peppermint oil, pequi oil, perilla seed oil, persimmon seed oil, pili nut oil, pine nut oil, pistachio oil, polycarbophil, polyethylene glycol, pomegranate seed oil, poppyseed oil, prune kernel oil, psyllium, pumpkin seed oil, quinoa oil, radish oil, ramtil oil, rapeseed oil, royle oil, safflower oil, salicornia oil, sapote oil, seje oil, sesame oil, soybean oil, spearmint oil, sunflower oil, taramira oil, thistle oil, tigernut oil, tomato seed oil, vegetable oil, walnut oil, watermelon seed oil, wheat germ oil, xantham gum, other fish oil, other gum, other insoluble fiber, other soluble fiber, and other vegetable oil.

I will now discuss the implanted reservoir in greater detail. In an example, a quantity of an absorption-reducing substance can be stored in an implanted reservoir before it is released into a person's gastrointestinal tract. In an example, this reservoir can be configured to be implanted within a person's body as part of an integrated device, system, and method for selectively reducing absorption of nutrients from unhealthy food.

In an example, there can be an opening, lumen, or shunt between the interior of an implanted reservoir and the interior of the person's gastrointestinal tract. In an example, an absorption-reducing substance can be released into the gastrointestinal tract through this opening, lumen, or shunt. In an example, this opening, lumen, or shunt enables controllable fluid communication between the interior of the implanted reservoir and the interior of the person's gastrointestinal tract.

In an example, there is a controllable flow of the substance from the interior of the reservoir to the interior of the gastrointestinal tract. In an example, there can be an opening, lumen, or shunt through which an absorption-reducing substance can flow, or be otherwise released, from an implanted reservoir into the interior of a portion of the gastrointestinal tract. In an example, an implanted reservoir, or an opening or lumen connecting it to the interior of the gastrointestinal tract, can have a one-way valve or filter that blocks movement of material from the gastrointestinal tract into the reservoir. This can help to prevent backflow of material from the gastrointestinal tract into the interior of the reservoir. This can prevent contamination of the absorption-reducing substance within the reservoir.

In an example, an implanted reservoir can be configured to be implanted within, or attached to, a body member selected from the group consisting of: stomach, duodenum, jejunum, ileum, caecum, colon, and esophagus. In an example, an implanted reservoir can be attached to the exterior surface of the stomach and have a tube from its interior to the interior of the stomach through which an absorption-reducing substance can be pumped into the stomach. In an example, an implanted reservoir can be configured to be implanted within the abdominal cavity and have a tube or other lumen that connects it to the interior of the gastrointestinal tract. In an example, an implanted reservoir can be configured to be implanted in a subcutaneous site or intraperitoneal site. In an example, an implanted reservoir can be configured to be implanted within, or attached to, adipose tissue or muscular tissue.

In various examples, a reservoir can be implanted within a person's body by one or more means selected from the group consisting of: suture or staple; adhesive or glue; clamp, clip, pin, or snap; elastic member; tissue pouch; fibrotic or scar tissue; screw; and tissue anchor. In an example, a reservoir can be rigid. In an example, a reservoir can be flexible. In various examples, an implanted reservoir, including a possible opening or lumen from the interior of the reservoir to the interior of the person's gastrointestinal tract, can be made from one or more materials selected from the group consisting of: cellulosic polymer, cobalt-chromium alloy, fluoropolymer, glass, latex, liquid-crystal polymer, nitinol, nylon, perflouroethylene, platinum, polycarbonate, polyester, polyether-ether-ketone, polyethylene, polyolefin, polypropylene, polystyrene, polytetrafluoroethylene, polyurethane, pyrolytic carbon material, silicone, stainless steel, tantalum, thermoplastic elastomer, titanium, and urethane.

In an example, an implanted reservoir can have multiple compartments. In an example, these multiple compartments can contain different types of absorption-reducing substances that are released in response to consumption of different types or quantities of food. In an example, these multiple compartments can contain different types of absorption-reducing substances that are released at different times or in different sequences. In an example, an implanted reservoir can have multiple compartments that contain different quantities of the same absorption-reducing substance that are released in response to consumption of different quantities or types of food. In an example, an implanted reservoir can have multiple compartments that contain separate amounts of one or more absorption-reducing substances that are released in discrete doses in response to separate eating events or episodes. In an example, an implanted reservoir can contain different types of absorption-reducing substances in different compartments which can be released and combined in different combinations to create specific and/or unique synergistic effects.

In an example, a reservoir can have an expanding balloon or bladder member to contain a variable quantity of an absorption-reducing substance. In an example, a reservoir can have a level indicator that that detects and communicates how much absorption-reducing substance is contained in the reservoir. In an example, the substance level can be communicated to an external source in a wireless manner. In an example, an implanted reservoir can be refilled or replaced. In an example, an implanted reservoir can be refilled with an absorption-reducing substance by one or more means selected from the group consisting of: an intra-gastric docking mechanism, such as a docking mechanism between a tube inserted orally and the reservoir; a needle or syringe that is temporarily inserted through the skin into the interior of the reservoir; a transdermal access port or tube; and a cartridge containing the substance that fits into the reservoir.

I will now discuss the release-control mechanism in greater detail. In an example, this invention includes a release-control mechanism that controls the manner in which an absorption-reducing substance is released from an implanted reservoir into a person's gastrointestinal tract in response to consumption of unhealthy food. In an example, a release-control mechanism can release an absorption-reducing substance into a person's stomach or intestine when a person consumes and/or digests an unhealthy type of food and/or nutrients. A release-control mechanism can be a key part of an overall system that helps a person to get proper nutrition while they manage their weight.

In an example, a release-control mechanism can activate the flowing, pumping, and/or spraying of an absorption-reducing substance from an implanted reservoir into a person's gastrointestinal tract to selectively reduce absorption of food nutrients. In an example, a release-control mechanism can selectively, temporarily, and automatically release an absorption-reducing substance into a person's gastrointestinal tract in response to consumption or digestion of selected types of food and/or nutrients as detected by a food-identifying sensor.

In an example, a release-control mechanism can selectively and automatically start or increase the flow of an absorption-reducing substance into a person's gastrointestinal tract when a food-identifying sensor identifies that a person is consuming or digesting unhealthy food. In an example, this release-control mechanism can also selectively and automatically stop or decrease the flow of the absorption-reducing substance into the person's gastrointestinal tract when the food-identifying sensor identifies that the person is consuming or digesting healthy food. In this manner, a release-control mechanism can selectively reduce absorption of nutrients from unhealthy food, but not reduce absorption of nutrients from healthy food. This can prevent the adverse potential for malnutrition that sometimes occurs with food-blind malabsorption devices and procedures in the prior art.

In an example, a release control mechanism can release a substance that creates a temporary coating on the interior walls of a portion of a person's gastrointestinal tract when the person eats unhealthy types and/or quantities of food. This can selectively reduce absorption of nutrients from unhealthy types and/or quantities of food. In an example, a release control mechanism can release a substance that creates a coating around a bolus of unhealthy food that is passing through a person's gastrointestinal tract. This can selectively reduce absorption of nutrients from unhealthy types and/or quantities of food.

In an example, a release-control mechanism can actuate a valve, pump, or variable-opening filter to release a flow or spray of an absorption-reducing substance into a person's gastrointestinal tract. In various examples, a release-control mechanism can include one or more valves selected from the group consisting of: biological valve, chemical valve, electromechanical valve, helical valve, piezoelectric valve, MEMS valve, hydraulic valve and micro-valve. In an example, a release-control mechanism can include one or more Micro Electrical Mechanical Systems (MEMS). In various examples, a release-control mechanism can include one or more components selected from the group consisting of: electronic mechanism, MEMS mechanism, microfluidic mechanism, biochemical mechanism, and biological mechanism.

In an example, a release-control mechanism can include a pump that pumps or sprays an absorption-reducing substance directly into a person's gastrointestinal tract. In various examples, a release-control mechanism can include one or more pumps selected from the group consisting of: 360-degree peristaltic pump, axial pump, biochemical pump, biological pump, centrifugal pump, convective pump, diffusion pump, dispensing pump, effervescent pump, elastomeric pump, electrodiffusion pump, electrolytic pump, electromechanical pump, electroosmotic pump, fixed-occlusion peristaltic pump, gravity feed pump, helical pump, hose-type peristaltic pump, hydrolytic pump, infusion pump, mechanical screw-type pump, MEMS pump, micro pump, multiple-roller peristaltic pump, osmotic pump, peristaltic pump, piezoelectric pump, pulsatile pump, rotary pump, spring-loaded roller pump, tube-type peristaltic pump, and vapor pressure pump.

In various examples, a release-control mechanism can be powered by an external power source, by internal power source, or by a combination of external and internal power sources. In an example, a release-control mechanism can transduce kinetic, thermal, or biochemical energy from within the person's body. In an example, a release-control mechanism may be powered by transducing the kinetic energy of stomach movement. In an example, the flow of an absorption-reducing substance from an implanted reservoir to a person's gastrointestinal tract can be caused by a pump that is controlled by a release-control mechanism. In an example, the flow of an absorption-reducing substance from an implanted reservoir to a person's gastrointestinal tract can be caused by the natural movement of a person's body and controlled by a release-control mechanism.

In various examples, a release-control mechanism can be powered from one or more energy sources selected from the group consisting of: a battery, an energy-storing chip, energy harvested or transduced from a bioelectrical cell, energy harvested or transduced from an electromagnetic field, energy harvested or transduced from an implanted biological source, energy harvested or transduced from blood flow or other internal fluid flow, energy harvested or transduced from body kinetic energy, energy harvested or transduced from glucose metabolism, energy harvested or transduced from muscle activity, energy harvested or transduced from organ motion, and energy harvested or transduced from thermal energy.

In various examples, a release-control mechanism can be can be made from one or more materials selected from the group consisting of: cobalt-chromium alloy, fluoropolymer, latex, liquid-crystal polymer, nylon, perflouroethylene, platinum, polycarbonate, polyester, polyethylene, polyolefin, polypropylene, polystyrene, polytetrafluoroethylene, polyurethane, polyvinyl chloride, pyrolytic carbon material, silicon, silicone, silicone rubber, stainless steel, tantalum, titanium, and urethane.

In an example, a release-control mechanism can start releasing an absorption-reducing substance into the gastrointestinal tract when a food-identifying sensor detects that the person has begun consuming unhealthy food and can stop releasing the absorption-reducing substance when the sensor detects that the person has begun consuming healthy food. In an example, the amount of substance that is released can be selectively and automatically increased when the sensor detects that the person is consuming or digesting unhealthy food and the amount of substance that is released can be selectively and automatically decreased when the sensor detects that the person is consuming or digesting healthy food.

In an example, unhealthy types of food can be identified by their having a high concentration of nutrients selected from the group consisting of: sugars, simple sugars, simple carbohydrates, fats, saturated fats, fat cholesterol, and sodium. In an example, unhealthy types and/or quantities of food can be identified by their having a high cumulative amount of one or more nutrients in the group consisting of: sugars, simple sugars, simple carbohydrates, fats, saturated fats, fat cholesterol, and sodium.

In an example, a release-control mechanism can include electronic components. In an example, a release-control mechanism can have one or more microchips or CPUs. In an example, a release-control mechanism can include a memory that tracks the cumulative amounts of nutrients that a person consumes during an episode of eating or during a selected period of time. For example, a release-control mechanism may count how many units of sugar, fat, or sodium are consumed by a person during the course of a day.

In an example, a release-control mechanism can allow up to a certain amount of one or more selected types of food or nutrients to be consumed by a person before it triggers the release of an absorption-reducing substance into the person's gastrointestinal tract. In an example, a release-control mechanism can be programmed to allow moderate consumption of some types of foods, but not excess consumption. In an example, a release-control mechanism can be programmed to allow unmodified absorption of selected foods for a limited time period or up to a certain amount. In an example, a release-control mechanism can be programmed to allow moderate consumption of some foods without malabsorption, but can cause malabsorption if there is excessive consumption of those foods.

In an example, a release-control mechanism can include electronics that can be wirelessly programmed in order to change the types and/or quantities of selected foods or nutrients for which nutrient absorption is automatically reduced. In an example, there can be a list in the device's memory of selected foods or nutrients which will trigger the release of an absorption-reducing substance into the person's gastrointestinal tract. In an example, a release-control mechanism can be programmed to change this list. In an example, the types of foods can be changed by programming In an example, the quantities of foods can be changed by programming In an example, the types and/or quantities of foods on the list can be automatically changed by a device with automatic learning capability.

In various examples, the operation of a release-control mechanism can be manually or automatically adjusted based on one or more factors selected from the group consisting of: the person's short-term eating patterns; the person's long-term eating patterns; the person's short-term exercise patterns and caloric expenditure; the person's long-term exercise patterns and caloric expenditure; the person's success in meeting weight reduction goals; holidays or other special events; professional guidance and diet planning; social support networks; financial constraints and incentives; and degree of sensor precision and measurement uncertainty.

In various examples, a release-control mechanism can be designed or programmed to selectively modify the absorption of selected types of food based on: the time of the day (to reduce snacking between meals or binge eating at night); the person's cumulative caloric expenditure (to reward exercise and achieve energy balance); special social events and holidays (to allow temporary relaxation of dietary restrictions); physical location measured by GPS (to discourage eating in locations that are associated with unhealthy consumption); and/or social networking connections and support groups (to provide peer support for willpower enhancement).

In various examples, one or more aspects of the operation of a release-control mechanism can be manually or automatically adjusted, wherein these aspects are selected from the group consisting of: the type of food consumed which triggers decreased food absorption; the quantity of food consumed during a given period of time which triggers decreased food absorption; the time of day, day of the week, or other timing parameter concerning food consumption which triggers decreased food absorption; the effect of past food consumption behavior on decreased food absorption; the effect of caloric expenditure behavior on decreased food absorption; and a personalized dietary plan treatment created for the person by a health care professional.

In an example, a release-control mechanism can include a wireless data transmitter and receiver. In an example, a release-control mechanism can communicate wirelessly with a food-identifying sensor that is implanted in a different part of a person's body. In an example, a release-control mechanism can communicate wirelessly with a source that is external to the person's body. In an example, a release-control mechanism can be programmed, or otherwise adjusted, by an external remote control unit.

In an example, a release-control mechanism can wirelessly communicate with a food-identifying sensor that is carried by, or worn by, a person. In various examples, a release-control mechanism can be in wireless communication with a food-identifying sensor that a person wears on their wrist, hand, finger, arm, torso, neck, head, and/or ear. In various examples, a release-control mechanism can be in wireless communication with a food-identifying sensor that is incorporated into a piece of electronically-functional jewelry such as a necklace, pendant, finger ring, bracelet, nose ring, or earring. In various examples, a release-control mechanism can be in wireless communication with a food-identifying sensor that is incorporated into a person's wrist watch, eyeglasses, hearing aid, or bluetooth device.

In an example, a release-control mechanism can communicate wirelessly with one or more external computers that are linked by a network, such as the internet. In an example, a release-control mechanism can be wirelessly programmed, or otherwise adjusted, by the person in whom the device is implanted. In an example, a release-control mechanism can be wirelessly programmed, or otherwise adjusted, by a care giver or other health care professional. In various examples, a release-control mechanism can have wireless communication with one or more of the following members: a food-identifying sensor that is implanted within, or attached to, in a different area of the person's body; a remote computer, network, or remote control unit that is external to the person's body; and an external mobile, cellular, or tabular electronic communication device. In an example, a release-control mechanism can be a key part of an overall system to ensure that a person gets proper nutrition while this person is losing weight.

As shown in FIGS. 1 through 6, this invention can be embodied in a device for selectively and automatically reducing the absorption of selected types of food in a person's gastrointestinal tract. This device can comprise: (a) a food-identifying sensor that selectively detects when the person is consuming and/or digesting selected types of food; (b) an absorption-reducing substance that is released into the interior of the person's gastrointestinal tract to temporarily reduce absorption of nutrients from food by the gastrointestinal tract; (c) an implanted reservoir that contains a quantity of the absorption-reducing substance, wherein this reservoir is configured to be implanted within the person's body and wherein there is an opening or lumen through which the absorption-reducing substance is released from the reservoir into the interior of a portion of the person's gastrointestinal tract; and (d) a release-control mechanism that controls the release of the absorption-reducing substance from the reservoir into the person's gastrointestinal tract, wherein this release-control mechanism can selectively and automatically increase the release of the absorption-reducing substance when the food-identifying sensor detects that the person is consuming and/or digesting selected types of food.

In an example, the food-identifying sensor of this embodiment can selectively discriminate between consumption and/or digestion of unhealthy food and consumption and/or digestion of healthy food. In an example, unhealthy food can be identified as having a high concentration of one or more nutrients selected from the group consisting of: sugars, simple sugars, simple carbohydrates, fats, saturated fats, cholesterol, and sodium. In an example, unhealthy food can be identified as having a large amount of one or more nutrients selected from the group consisting of: sugars, simple sugars, simple carbohydrates, fats, saturated fats, cholesterol, and sodium. In an example, unhealthy food can be identified as food with an amount of one or more nutrients selected from the group consisting of sugars, simple sugars, simple carbohydrates, fats, saturated fats, cholesterol, and sodium that is more than the recommended amount of such nutrient for the person during a given period of time.

In an example, the food-identifying sensor of this embodiment can be selected from the group consisting of: chemical sensor, biochemical sensor, accelerometer, amino acid sensor, biological sensor, camera, chemoreceptor, cholesterol sensor, chromatography sensor, EGG sensor, electrolyte sensor, electromagnetic sensor, electronic nose, EMG sensor, enzyme-based sensor, fat sensor, flow sensor, particle size sensor, peristalsis sensor, genetic sensor, glucose sensor, imaging sensor, impedance sensor, infrared sensor, interferometer, medichip, membrane-based sensor, Micro Electrical Mechanical System (MEMS) sensor, microfluidic sensor, micronutrient sensor, molecular sensor, motion sensor, muscle activity sensor, nanoparticle sensor, neural impulse sensor, nutrient sensor, optical sensor, osmolality sensor, pH level sensor, pressure sensor, protein-based sensor, reagent-based sensor, smell sensor, sound sensor, strain gauge, taste sensor, and temperature sensor.

In an example, the absorption-reducing substance of this embodiment can coat food, food particles, nutrients, and/or chyme in the gastrointestinal tract. In an example, this absorption-reducing substance can temporarily coat a portion of the interior walls of the intestine. In an example, this absorption-reducing substance can bind to food, food particles, nutrients, and/or chyme in the gastrointestinal tract. In an example, this absorption-reducing substance can temporarily bind to a portion of the interior walls of the intestine. In an example, this absorption-reducing substance can temporarily increase the viscosity, increase the thickness, and/or decrease the nutrient permeability of the mucus that covers a portion of the interior walls of the person's intestine. In an example, the absorption-reducing substance of this embodiment can comprise one or more ingredients that are Generally Recognized As Safe (GRAS) under Sections 201(s) and 409 of the Federal Food, Drug, and Cosmetic Act.

In an example, the release-control mechanism of this embodiment can: start or increase the release of the absorption-reducing substance into the person's gastrointestinal tract in response to detection of consumption or digestion of unhealthy types of food by the food-identifying sensor; and/or stop or decrease the release of the absorption-reducing substance into the person's gastrointestinal tract in response to detection of consumption or digestion of healthy types of food by the food-identifying sensor. In an example, unhealthy food can be identified as having a relatively large amount or concentration of one or more nutrients selected from the group consisting of: sugars, simple sugars, simple carbohydrates, fats, saturated fats, cholesterol, and sodium.

In an example, the release-control mechanism of this embodiment can communicate wirelessly with a source external to the person's body. In an example, this release-control mechanism can be programmed, or otherwise adjusted, to change the types of selected foods or nutrients to which it responds by releasing an absorption-reducing substance into the person's gastrointestinal tract. In an example, this release-control mechanism can be programmed to adjust one or more of the following aspects of its response to the food-identifying sensor: the type of food which triggers decreased food absorption; the quantity of food which triggers decreased food absorption; the time of day, day of the week, or other timing parameter concerning food consumption which triggers decreased food absorption; the effect of the person's past food consumption on decreased food absorption; the effect of the person's caloric expenditure on decreased food absorption; and the effect of a personalized diet plan created for the person by a health care professional.

In an example, this invention can be embodied in a device for selectively and automatically reducing the absorption of unhealthy food by a person's gastrointestinal tract. This device can comprise: (a) a food-identifying sensor that selectively detects when the person is consuming and/or digesting unhealthy food, wherein unhealthy food is identified as food that has a relatively large amount or concentration of one or more nutrients selected from the group consisting of: sugars, simple sugars, simple carbohydrates, fats, saturated fats, cholesterol, and sodium; (b) an absorption-reducing substance that is released into the person's gastrointestinal tract to reduce absorption of nutrients from food in the gastrointestinal tract by one or more means selected from the group consisting of: coating food, food particles, nutrients, and/or chyme in the gastrointestinal tract; temporarily coating a portion of the interior walls of the gastrointestinal tract; binding to food, food particles, nutrients, and/or chyme in the gastrointestinal tract; temporarily binding to a portion of the interior walls of the gastrointestinal tract; temporarily blocking nutrient-absorbing organelles on a portion of the interior walls of the person's duodenum; temporarily increasing the viscosity of the mucus on a portion of the interior walls of the person's intestine; and temporarily decreasing the nutrient permeability of the mucus on a portion of the interior walls of the person's intestine; (c) an implanted reservoir that contains a quantity of the absorption-reducing substance, wherein this reservoir is configured to be implanted within the person's body, and wherein there is an opening or lumen through which the absorption-reducing substance is released from the reservoir into a portion of the person's gastrointestinal tract; and (d) a release-control mechanism that controls the release of the absorption-reducing substance from the reservoir into the person's gastrointestinal tract, wherein the amount of absorption-reducing substance released can be selectively and automatically increased when the food-identifying sensor detects that the person is consuming or digesting unhealthy food and wherein the amount of substance released can be selectively and automatically decreased when the sensor detects that the person is consuming or digesting healthy food.

FIGS. 7 through 10 show additional examples of how this invention can be embodied in a device and method for selectively and automatically reducing absorption of nutrients from unhealthy food in a person's gastrointestinal tract. In these examples, the food-identifying sensor is a mouth-based or nose-based sensor that is in fluid communication with the person's mouth or nose.

There are advantages to using a mouth-based or nose-based food-identifying sensor in such a device or method for selective malabsorption of unhealthy food. A mouth-based or nose-based food-identifying sensor can detect consumption of unhealthy food earlier than an intragastric sensor. This provides "earlier detection" that a bolus of unhealthy food will be entering the stomach and intestine, before the food even enters the stomach. This "earlier detection" provides more lead time for the device and method to more-thoroughly modify the gastrointestinal tract in order to more-completely reduce absorption of nutrients from the bolus of unhealthy food.

FIGS. 7 through 10 show examples of how this invention can be embodied in a device for selectively and automatically reducing absorption of unhealthy food in a person's gastrointestinal tract using a mouth-based food-identifying sensor. In an example, this device can comprise: (a) a food-identifying sensor that selectively detects when a person is consuming or digesting selected types of food, wherein this food-identifying sensor is configured to be implanted or attached within the person's oral cavity, the person's nasal cavity, or tissue surrounding one of these cavities; and (b) an absorption-reducing member that is implanted within the person's body, wherein this absorption-reducing member can selectively and automatically reduce the absorption of food within the person's gastrointestinal tract when the sensor detects that the person is consuming or digesting selected types of food.

FIGS. 7 through 10 also show examples of how this invention can be embodied in a method for selectively and automatically reducing absorption of unhealthy food in a person's gastrointestinal tract using a mouth-based food-identifying sensor. In an example, such a method can comprise: (a) selectively and automatically detecting when a person is consuming or digesting selected types of food by means of a sensor that is configured to be implanted or attached within the person's oral cavity, the person's nasal cavity, or tissue surrounding one of these cavities; and (b) selectively and automatically reducing the absorption of food within the person's gastrointestinal tract by means of an implanted absorption-reducing member, wherein this member selectively and automatically reduces food absorption when the sensor detects that the person is consuming or digesting selected types of food.

Figure 7:
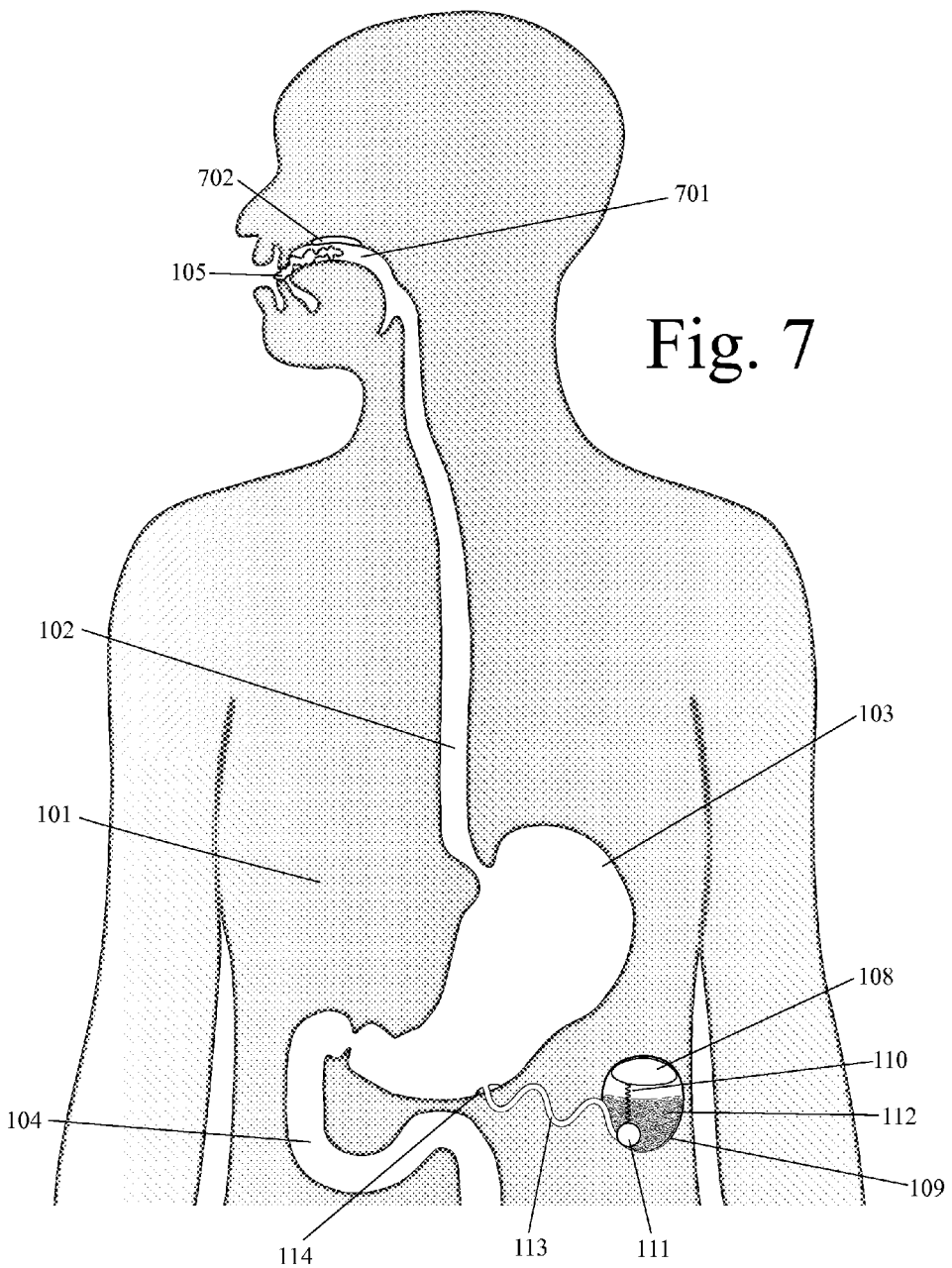

FIG. 7 shows a longitudinal cross-sectional view of a person's torso 101 and head, wherein the person's head is turned sideways to provide a lateral cross-sectional view of the person's head. FIG. 7 includes a longitudinal cross-sectional view of the entire upper portion of the person's gastrointestinal tract, including the person's oral cavity 701, esophagus 102, stomach 103, and duodenum 104. This figure also shows a bolus of food 105 in oral cavity 701, wherein this person is starting to consume and digest this bolus of food 105. In FIG. 7, bolus of food 105 is healthy food.

FIG. 7 also shows an example of an implanted device that enables selective malabsorption of unhealthy food using a mouth-based sensor. Selective malabsorption of unhealthy food, while also allowing normal absorption of healthy food, can help a person to lose weight without suffering deficiencies of essential nutrients that can occur with food-blind bariatric procedures and malabsorption devices in the prior art.

In the example shown in FIG. 7, food-identifying sensor 702 is attached to, or implanted within, the palatal vault of the person's oral cavity 701. In other examples, a food-identifying sensor may be implanted in other locations that are in fluid and/or gaseous communication with the person's oral cavity and/or nasal cavity. Food-identifying sensor 702 can selectively and automatically detect when the person is beginning to consume and digest unhealthy food. In an example, food-identifying sensor 702 can identify unhealthy food by performing chemical analysis of saliva in the person's mouth. In an example, unhealthy food can be identified as having a high concentration of one or more of the following nutrients: sugars, simple sugars, simple carbohydrates, fats, saturated fats, cholesterol, and sodium.

In various examples, food-identifying sensor 702 can be selected from the group of sensors consisting of: chemical sensor, biochemical sensor, amino acid sensor, biological sensor, chemoreceptor, cholesterol sensor, chromatography sensor, EGG sensor, enzyme-based sensor, fat sensor, particle size sensor, peristalsis sensor, glucose sensor, impedance sensor, membrane-based sensor, Micro Electrical Mechanical System (MEMS) sensor, microfluidic sensor, micronutrient sensor, molecular sensor, motion sensor, nutrient sensor, osmolality sensor, pH level sensor, protein-based sensor, reagent-based sensor, and temperature sensor.

In the embodiment of the invention that is shown in FIG. 7, food-identifying sensor 702 can communicate by wireless transmission with release-control mechanism 108. Release-control mechanism 108 is contained in implanted reservoir 109 that is implanted within the person's abdominal cavity. Release-control mechanism 108 is connected by wire 110 to pump 111 which is also contained in reservoir 109. Pump 111 is in fluid communication with absorption-reducing substance 112 that is contained in reservoir 109 until this substance is released into the stomach 103 through lumen 113 and one-way valve 114. In an example, absorption-reducing substance 112 can be selectively and automatically released into the interior of the person's stomach 103 to reduce food absorption when food-identifying sensor 702 detects consumption of unhealthy food in the person's oral cavity 701.

FIG. 7 shows how this embodiment of the invention does not actively respond to the consumption and digestion of bolus of healthy food 105. In this figure, the device does not interfere with the normal absorption of healthy food 105. This is an advantage over malabsorption procedures and devices that blindly reduce absorption of all food, including healthy food. This avoids the deficiencies of essential nutrients that can be caused by food-blind malabsorption procedures and devices in the prior art.

Figure 8:
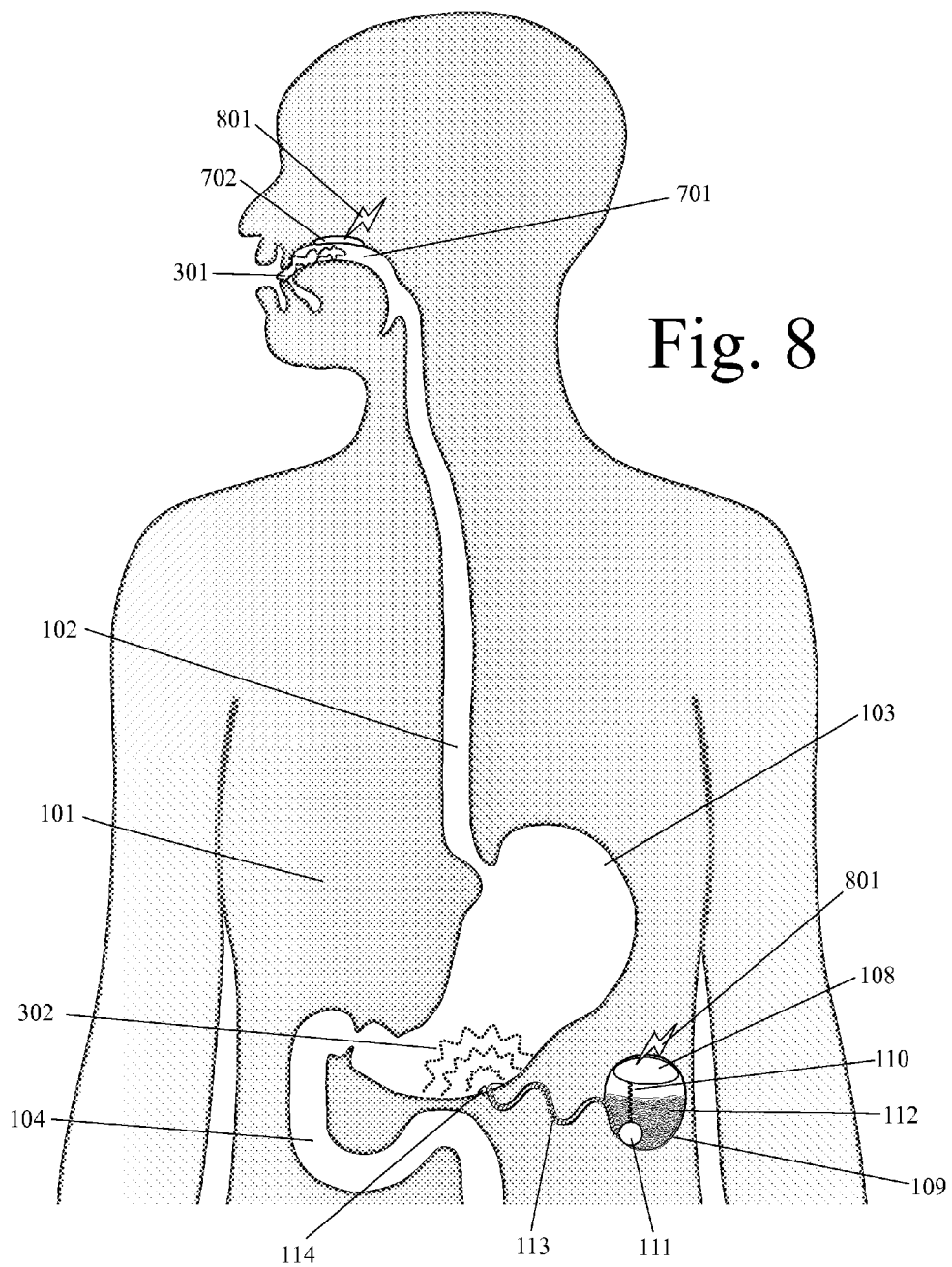

FIG. 8, in contrast, shows how this embodiment can selectively and automatically respond to a bolus of food 301 that is unhealthy. In an example, bolus of food 301 can have a high concentration of one or more of the following nutrients: sugars, simple sugars, simple carbohydrates, fats, saturated fats, cholesterol, and sodium. The following is the sequence of actions involved as the device selectively and automatically reduces absorption of nutrients from unhealthy food 301.

First, in FIG. 8, the person has inserted a bolus of unhealthy food 301 into their mouth and this bolus of food 301 is starting to be digested by chewing action and saliva. Next, the bolus of unhealthy food 301 is identified as unhealthy by food-identifying sensor 702. In an example, this identification can be done by analyzing the chemical composition of saliva in the mouth as the food begins to be digested. Then, food-identifying sensor 702 sends a wireless signal 801 to release-control mechanism 108. This wireless signal informs release-control mechanism 801 that the person has consumed a bolus of unhealthy food 301.

In FIG. 8, the wireless signal that is transmitted from food-identifying sensor 702 to release-control mechanism 108 is represented by two "lightning bolt" symbols labeled 801. The "lightning bolt" symbol (labeled 801) near the sensor represents the origination point of the wireless signal and the "lightning bolt" symbol (also labeled 801) near the release-control mechanism represents the destination point of the wireless signal. The same label (801) is used for the wireless signal in both locations because it is the same signal, just interacting with the device at different locations.

In FIG. 8, the receipt of wireless signal 801 by release-control mechanism 108 triggers the activation of pump 111. Pump 111 then releases a quantity of absorption-reducing substance 112 (through lumen 113 and one-way valve 114) into the interior of stomach 103. The release of absorption-reducing substance 112 into stomach 103 is represented by concentric wavy dotted lines 302 that radiate outwards from one-way valve 114 into the person's stomach 103.

As was shown in previous figures, an absorption-reducing substance 112 can selectively and automatically reduce absorption of nutrients from unhealthy food by coating the walls of the duodenum 104 when unhealthy food is detected. As was shown in previous figures, an absorption-reducing substance 112 can selectively and automatically reduce absorption of nutrients from unhealthy food by coating the bolus of unhealthy food 301 (or chyme containing food particles from this bolus of unhealthy food) as it passes through the stomach 103. In an example, absorption-reducing substance 112 can coat both the duodenal walls and the bolus of food.

In various examples, an absorption-reducing substance 112 can reduce absorption of nutrients from a bolus of unhealthy food 301 by one of more actions selected from the group consisting of: temporarily coating the interior walls of duodenum 104; coating a bolus of unhealthy food 301 (or chyme containing food particles from this bolus); changing the speed at which a bolus of unhealthy food 301 travels through the gastrointestinal tract; temporarily binding to the interior walls of duodenum 104; binding to a bolus of unhealthy food 301; increasing the thickness of the mucus covering the interior walls of the duodenum; increasing the viscosity of the mucus covering the interior walls of the duodenum; and decreasing the nutrient permeability of the mucus covering the interior walls of the duodenum.

In an example, release-control mechanism 108 can start releasing an absorption-reducing substance 112 into the person's stomach 103 in response to detection of consumption of unhealthy food 301 by food-identifying sensor 702. In an example, release-control mechanism 108 can stop releasing absorption-reducing substance 112 into the person's stomach 103 in response to detection of consumption of healthy food 105 by the food-identifying sensor 702.

In an example, release-control mechanism 108 can communicate wirelessly with a source external to the person's body. In an example, release-control mechanism 108 can be programmed, or otherwise adjusted, to change the types of selected foods or nutrients to which it responds by releasing an absorption-reducing substance 112 into the person's gastrointestinal tract. In various examples, release-control mechanism 108 can be programmed to adjust one or more of the following aspects of its response to food-identifying sensor 702: the types of food and/or nutrients which trigger decreased food absorption; the quantities of food and/or nutrients which trigger decreased food absorption; the time of day, day of the week, or other timing parameters concerning food consumption which trigger decreased food absorption; the effects of the person's past food consumption on decreased food absorption; the effects of the person's caloric expenditure on decreased food absorption; and the effects of a personalized diet plan created for the person by a health care professional.

Figure 9:
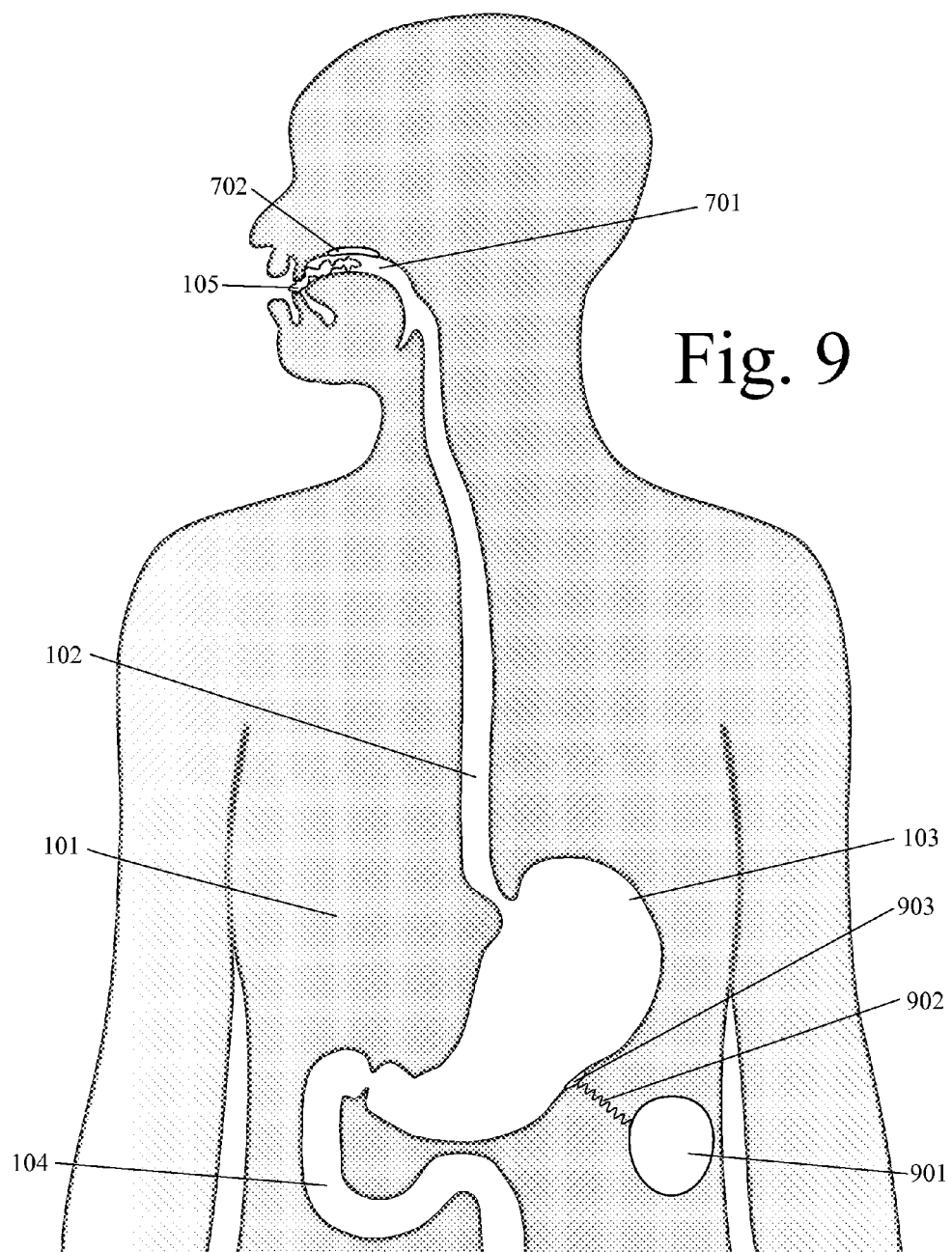
Figure 10:
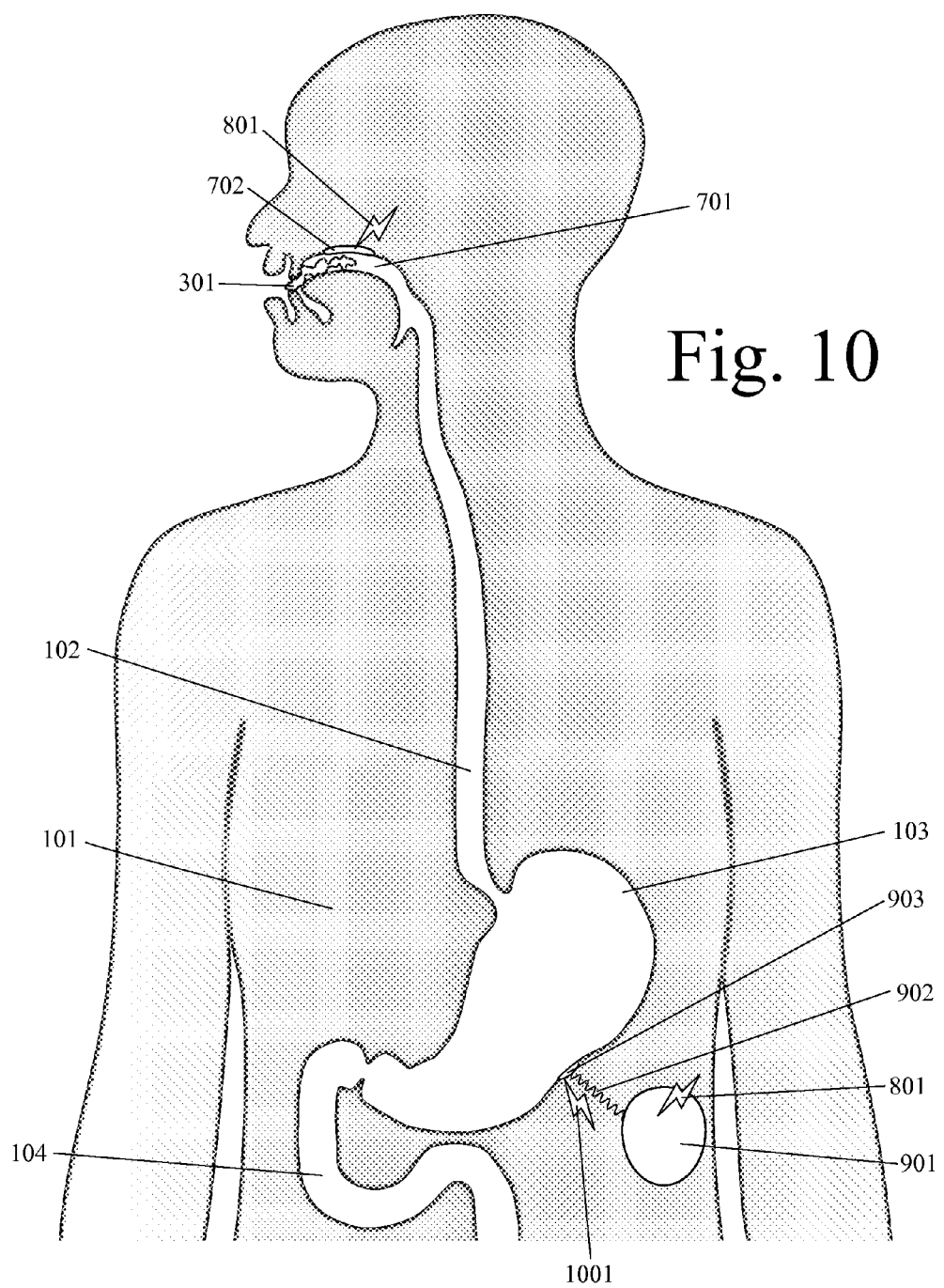

FIGS. 9 and 10 show another example of how this invention can be embodied in a device and method that uses a mouth-based food-identification sensor to selectively and automatically reduce absorption of unhealthy food. Similar to FIG. 7, FIG. 9 shows a longitudinal cross-sectional view of a person's torso 101 and head. This view includes a longitudinal cross-sectional view of the entire upper portion of the person's gastrointestinal tract, including the person's oral cavity 701, esophagus 102, stomach 103, and duodenum 104. This figure also shows a bolus of healthy food 105 in oral cavity 701. The person is starting to consume and digest this bolus of healthy food 105.

FIG. 9 also shows another example of an implanted device that enables selective malabsorption of unhealthy food using a mouth-based sensor. In this example, the absorption-reducing member comprises an implanted electrical component 901. In this example, implanted electrical component 901 is an implanted electrical impulse generator that delivers an electrical impulse to the walls of the person's stomach 103 via wire 902 and electrode 903. In various examples, implanted electrical component 901 can deliver electricity to other portions of the person's gastrointestinal tract or to nerves in communication with the person's gastrointestinal tract.

There are many examples of implanted electrical components in the prior art that deliver electricity to portions of the body. The exact type of implanted electrical component that is used is not central to this invention. However, selectively and automatically activating such a device in response to consumption of unhealthy food, as detected early in consumption by a mouth-based food-identifying sensor, is novel. Selective, automatic, and early activation of an implanted electrical component has significant advantages over devices and methods for electrical stimulation of the gastrointestinal tract in the prior art that are blind concerning whether the person is consuming unhealthy or healthy food.

As one advantage, when an electrical stimulation device is only activated when the person is eating unhealthy food, then the person's muscles and/or nerves will be less likely to habituate to the electrical stimulation and cause stimulation to lose its effectiveness. As a second advantage, when an electrical stimulation device is only activated when the person is eating unhealthy food, then the person is less likely to suffer from deficiencies of essential nutrients because there is no interference with the digestion and absorption of healthy food. As a third advantage, when an electrical stimulation device is only activated when the person is eating unhealthy food, the device uses less battery power than a food-blind device.

FIG. 9 shows how this embodiment of the invention does not actively respond to consumption and digestion of bolus of healthy food 105. In this figure, the device does not interfere with the normal absorption of healthy food 105. For the three reasons discussed above, this is an advantage over implanted electrical stimulators in the prior art that blindly reduce absorption of all food, including healthy food. Having early detection of unhealthy food consumption by a mouth-based sensor allows the device to prepare the stomach and intestine for malabsorption before the food even reaches the stomach. This is an advantage over intragastric sensors.

FIG. 10, in contrast, shows how this embodiment can selectively and automatically respond to a bolus of food 301 that is unhealthy. In an example, bolus of unhealthy food 301 can have a high concentration of one or more of the following nutrients: sugars, simple sugars, simple carbohydrates, fats, saturated fats, cholesterol, and sodium. The following is the sequence of actions involved as the device in FIG. 10 selectively and automatically reduces absorption of nutrients from unhealthy food 301.

First, in FIG. 10, the person has inserted a bolus of unhealthy food 301 into their mouth and this bolus of food 301 is starting to be digested by chewing action and saliva. Next, the bolus of unhealthy food 301 is identified as unhealthy by food-identifying sensor 702. In an example, this identification can be done by analyzing the chemical composition of saliva in the mouth as the food begins to be digested. Then, food-identifying sensor 702 sends a wireless signal 801 to implanted electrical component 901. In this example, the absorption-control member of this invention comprises implanted electrical component 901. The wireless signal informs implanted electrical component 901 that the person has consumed a bolus of unhealthy food 301.

In FIG. 10, the receipt of wireless signal 801 by implanted electrical component 901 triggers an electrical impulse 1001 through wire 902 and electrode 903 to the wall of the person's stomach 103. In this example, this electrical impulse changes the motility of gastric peristalsis to reduce absorption of the bolus of unhealthy food 301 by the person's gastrointestinal tract. In an example, this electrical impulse can increase the speed at which bolus of unhealthy food 301 moves through the person's stomach, duodenum, or other portions of the person's gastrointestinal tract. In an example, this electrical impulse can decrease secretion of enzymes by the person's stomach or adjacent secretory organ's along the person's gastrointestinal tract.

In various examples, application of electricity to one or more portions of the person's gastrointestinal tract, or to the nerves that innervate this tract, can selectively and automatically reduce absorption of nutrients from bolus of unhealthy food 301, as identified by mouth-based food-identification sensor 702. In an example, an implanted absorption-reducing member, such as implanted electrical component 901, can start stimulating an organ along the gastrointestinal tract in response to detection of consumption of unhealthy food 301 by food-identifying sensor 702. In an example, an implanted absorption-reducing member, such as implanted electrical component 901, can stop stimulating an organ along the gastrointestinal tract in response to detection of consumption of healthy food 105 by food-identifying sensor 702.

In an example, implanted electrical component 901 can communicate wirelessly with a source external to the person's body. In an example, an absorption-reducing member, such as implanted electrical component 901, can be programmed, or otherwise adjusted, to change the types of selected foods or nutrients to which it responds by releasing an absorption-reducing substance 112 into the person's gastrointestinal tract.

In various examples, an absorption-reducing member, such as implanted electrical component 901, can be programmed to adjust one or more of the following aspects of its response to food-identifying sensor 702: the types of food and/or nutrients which trigger decreased food absorption; the quantities of food and/or nutrients which trigger decreased food absorption; the time of day, day of the week, or other timing parameters concerning food consumption which trigger decreased food absorption; the effects of the person's past food consumption on decreased food absorption; the effects of the person's caloric expenditure on decreased food absorption; and the effects of a personalized diet plan created for the person by a health care professional.

As shown in FIGS. 7 through 10, this invention can be embodied in a device for selectively and automatically reducing the absorption of selected types of food in a person's gastrointestinal tract comprising: (a) a mouth-based or nose-based food-identifying sensor that selectively detects when a person is consuming or digesting selected types of food, wherein this food-identifying sensor is configured to be implanted or attached within the person's oral cavity, the person's nasal cavity, or tissue surrounding one of these cavities; and (b) an absorption-reducing member that is implanted within the person's body, wherein this absorption-reducing member can selectively and automatically reduce the absorption of food within the person's gastrointestinal tract when the sensor detects that the person is consuming or digesting selected types of food.

Also, as shown in FIGS. 7 through 10, this invention can be embodied in a method for selectively and automatically reducing the absorption selected types of food in the gastrointestinal tract comprising: (a) selectively and automatically detecting when a person is consuming or digesting selected types of food by means of a sensor that is configured to be implanted or attached within the person's oral cavity, the person's nasal cavity, or tissue surrounding one of these cavities; and (b) selectively and automatically reducing the absorption of food within the person's gastrointestinal tract by means of an implanted absorption-reducing member, wherein this member selectively and automatically reduces food absorption when the sensor detects that the person is consuming or digesting selected types of food.

In the following sections of this disclosure, I discuss various examples of these two device sub-components (mouth-based or nose-based food-identifying sensor and absorption-reducing member) and these two method steps (detecting when a person is consuming unhealthy food and reducing the absorption of this unhealthy food) in greater detail.

First, I will discuss the mouth-based or nose-based food-identifying sensor in greater detail. In an example, a food-identifying sensor can be configured to be attached to, or implanted within, a person's oral cavity, nasal cavity, or tissue surrounding one of these cavities. In an example, an implanted food-identifying sensor can be in fluid or gaseous communication with a person's oral cavity or nasal cavity. In an example, a food-identifying sensor can be configured to be attached to, or implanted within, a person's mouth or nose. In an example, an implanted food-identifying sensor can be in fluid or gaseous communication with a person's mouth or nose. In an example, a food-identifying sensor in a person's mouth or nose can be in wireless communication with an absorption-reducing member that is implanted elsewhere in the person's body. In an example, having a food-identifying sensor in a person's mouth or nose can provide "earlier detection" for activation of an absorption-reducing member elsewhere in the person's body.

A food-identifying sensor in a person's mouth or nose can detect consumption and/or digestion of unhealthy food as it is starting to be digested within a person's mouth. There are advantages of having an implanted food-identifying sensor be configured so as to be in fluid or gaseous communication with a person's oral or nasal cavities. Such a food-identifying sensor can provide "earlier detection" that a particular bolus of unhealthy food will be entering the stomach, before food enters the stomach. As compared to an intragastric sensor, a mouth-based or nose-based sensor provides more time for modification of the stomach or intestine to reduce absorption of nutrients from the bolus of food before the food reaches the stomach.

In an example, "earlier detection" of unhealthy food consumption from a mouth-based or nose-based sensor to an absorption-reducing member that is implanted elsewhere in the person's body can enable the walls of the duodenum to be thoroughly coated with an absorption-reducing coating before the bolus of unhealthy food arrives there. In another example, such "earlier detection" from a mouth-based or nose-based sensor can enable a food-coating substance to be thoroughly dispersed throughout the interior of the stomach before the bolus of unhealthy food even enters the stomach. These actions can more efficiently reduce absorption of a bolus of unhealthy food as it moves through the person's gastrointestinal tract. A mouth-based or nose-based food-identifying sensor can provide "earlier detection" to a release-control mechanism that releases an absorption-reducing substance into a person's stomach or intestine before a selected bolus of unhealthy food enters the stomach. By the time the bolus of food enters the stomach, the absorption-reducing substance can already be well dispersed throughout the stomach and/or intestine.

In an example, "earlier detection" from a mouth-based or nose-based food-identifying sensor can be sent to an absorption-reducing member that reduces absorption by applying electricity to a gastrointestinal organ or to nerves that are in communication with such an organ. For example, when a mouth-based or nose-based sensor detects that a person is starting to consume unhealthy food, such a sensor can send signals to an electrical stimulation device that is implanted elsewhere in the person's body. This electrical stimulation device can selectively apply electricity to the person's stomach, to nerves innervating the stomach, or to other organs or tissues in communication with the person's gastrointestinal tract in order to selectively reduce absorption of nutrients from a particular bolus of unhealthy food.

In an example, electrical stimulation can selectively modify the peristalsis of a gastrointestinal organ in order to selectively decrease absorption of nutrients from a bolus of unhealthy food. In another example, electrical stimulation can selectively decrease secretion of enzymes into the gastrointestinal tract to decrease absorption of nutrients from a selected bolus of unhealthy food. The selective malabsorption that is enabled by a mouth-based or nose-based food-identifying sensor can be superior to the indiscriminant malabsorption provided by devices, methods, and procedures in the prior art that are blind to whether a particular bolus of food passing through the gastrointestinal tract is unhealthy or healthy.

In an example, a mouth-based or nose-based food-identifying sensor can provide "earlier detection" to an absorption-reducing member that reduces food absorption by restricting the size of a portion of the person's gastrointestinal tract. For example, when a mouth-based or nose-based sensor detects that the person is starting to consume unhealthy food, a sensor can send signals to a gastric constriction device that: constrains the external size of the entire stomach; constrains the size of the entrance to the stomach; or changes the length of the gastrointestinal tract that is traveled by a selected bolus of food.

In an example, there can be an adjustable valve in a person's gastrointestinal tract that can direct different boluses of food through a shorter route with less absorption of nutrients versus a longer route with more absorption of nutrients. In an example, the shorter route can be a gastric bypass which can be selectively and remotely activated by the results of a food-identifying sensor. In an example, when a food-identifying sensor detects that the person is eating a bolus of unhealthy food, the sensor sends a wireless signal to an absorption-reducing member (a valve control mechanism in this example) that routes this bolus of unhealthy food through the shorter (bypass) route. When the person stops eating unhealthy food and starts eating healthy food, the sensor changes the valve so that healthy food goes through the longer route.

In an example, a food-identifying sensor can be implanted within, or attached to, a person's oral cavity. In an example, a food-identifying sensor can be configured to be attached to, or implanted within, a person's hard palate, palatal vault and/or upper mouth roof, teeth, tongue, or soft palate. In various examples, an food-identifying sensor can be attached to, or implanted by one or more means selected from the group consisting of: suture, staple, adhesive, glue, clamp, clip, pin, snap, elastic member, tissue pouch, fibrotic tissue, screw, and tissue anchor.

In an example, a sensor can be configured to be attached to, or implanted within, or attached underneath a person's tongue. In an example, a food-identifying sensor can be inserted into a person's tongue. In an example, a sensor can be attached or implanted sublingually. In an example, a sensor can be configured to be attached to, or inserted into, the soft palate tissues at the rear of a person's oral cavity. In an example, a sensor can be configured to be attached to, or implanted within, a person's teeth. In various examples, a sensor can be attached to the lingual, palatal, buccal, and/or labial surfaces of a person's teeth. In an example, a food-identifying sensor can be incorporated into a dental and/or orthodontic appliance. In an example, a food-identifying sensor can be incorporated into a dental bridge, cap, or crown.

In an example, a food-identifying sensor within a person's mouth can analyze saliva to selectively detect consumption of unhealthy food at the point of initial consumption. In various examples, a food-identifying sensor that is in fluid communication with a person's mouth can analyze saliva within the mouth in order to automatically and selectively detect when a person is digesting food that is high in sugar or fat. In an example, a food-identifying sensor in a person's mouth can be a chemical sensor. In various examples, a chemical sensor can detect the amount or concentration of sugars, simple carbohydrates, fats, saturated fats, cholesterol fat, and/or sodium in food.

In various examples, a food-identifying sensor that is in fluid or gaseous communication with a person's mouth or nose can identify food as being unhealthy using one or more methods selected from the group consisting of: chemical analysis of food as it begins to be digested within a person's mouth; olfactory analysis of food as it beings to be digested within a person's mouth; image analysis of images of food as it approaches the person's mouth; sonic analysis of chewing or swallowing as food is consumed; and analysis of signals from nerves that innervate the person's taste buds and/or olfactory receptors.

In various examples, a food-identifying sensor within a person's mouth or nose can be selected from the group of sensors consisting of: chemical sensor, biochemical sensor, accelerometer, amino acid sensor, biological sensor, camera, chemoreceptor, cholesterol sensor, chromatography sensor, electrogastrogram sensor, electrolyte sensor, electromagnetic sensor, EMG sensor, enzymatic sensor, fat sensor, flow sensor, particle size sensor, peristalsis sensor, genetic sensor, glucose sensor, imaging sensor, impedance sensor, interferometer, medichip, membrane-based sensor, Micro Electrical Mechanical System (MEMS) sensor, microfluidic sensor, micronutrient sensor, molecular sensor, motion sensor, muscle activity sensor, nanoparticle sensor, neural impulse sensor, optical sensor, osmolality sensor, pattern recognition sensor, pH level sensor, pressure sensor, protein-based sensor, reagent-based sensor, sound sensor, strain gauge, and temperature sensor.

I will now discuss the absorption-reducing member in greater detail. In an example, this invention can include an implanted absorption-reducing member that is in communication with a food-identifying sensor, wherein this sensor is implanted within a person's oral or nasal cavity and can detect when the person is eating unhealthy food. An absorption-reducing member can be in wireless communication with a food-identifying sensor that, in turn, is in fluid or gaseous communication with a person's oral and/or nasal cavities. In combination with a food-identifying sensor within the person's mouth or nose, an absorption-reducing member can selectively, temporarily, and automatically reduce the absorption of nutrients from unhealthy food while allowing normal absorption of nutrients from healthy food.

In one example, an absorption-reducing member can incorporate functions of the following sub-components that have been discussed previously: an absorption-reducing substance; an implanted reservoir; and a release-control mechanism. However, as shown in FIGS. 9 and 10, an absorption-reducing member is not limited to these three sub-components. An absorption-reducing member can selectively and automatically reduce absorption of nutrients from unhealthy food using other sub-components and means that do not require the release of an absorption-reducing substance into a person's gastrointestinal tract. We will now specify alternative sub-components and means for embodiment of an absorption-reducing member in greater detail.

In an example, an absorption-reducing member can be activated when a food-identifying sensor detects that a person is consuming a selected type of food. In an example, this selected type of food can be unhealthy food. In an example, unhealthy food can be identified as having a high concentration or amount of sugars, simple carbohydrates, fats, saturated fats, cholesterol fat, and/or sodium. In an example, a food-identifying sensor within a person's mouth can analyze saliva to detect one or more of these nutrients and thus identify unhealthy food. In an example, a food-identifying sensor in a person's mouth can be a chemical sensor.

In an example, an absorption-reducing member can be triggered when a food-identifying sensor detects that a person is consuming unhealthy food. In an example, an absorption-reducing member can selectively, temporarily, and automatically reduce the absorption of nutrients from a bolus of unhealthy food and then subsequently allow normal absorption of nutrients from a healthy bolus of food. The selective malabsorption that is enabled by the combination of a mouth-based food-identifying sensor and an absorption-reducing member creates a system for selection malabsorption that is superior to the indiscriminant malabsorption caused by devices and methods in the prior art that cannot differentiate unhealthy food versus healthy food.

In an example, an absorption-reducing member can selectively, temporarily, and automatically reduce absorption of nutrients from unhealthy food by releasing an absorption-reducing substance into a person's gastrointestinal tract when this person consumes unhealthy food. Consumption is detected by a mouth-based or nose-based food-identifying sensor. In an example, an absorption-reducing member can selectively, temporarily, and automatically reduce absorption of nutrients from food in the gastrointestinal tract by temporarily coating the walls of a person's duodenum, or another portion of a person's intestine, when the person consumes unhealthy food. In an example, an absorption-reducing member can reduce food absorption by coating a bolus of food as this bolus travels through the person's stomach or another portion of the person's gastrointestinal tract.

In various examples, an absorption-reducing member can release a substance that: temporarily coats the interior walls of the person's gastrointestinal tract as a bolus of unhealthy food passes through the tract; coats a bolus of unhealthy food as this food passes through the tract; or both. In various examples, an absorption-reducing member can release a substance that: temporarily binds to the interior walls of the person's gastrointestinal tract as a bolus of unhealthy food passes through the tract; binds to unhealthy food as the food passes through the tract; or both.

In an example, an absorption-reducing member can selectively reduce absorption of nutrients from unhealthy food by releasing a systemic pharmaceutical agent when a mouth-based or nose-based food-identifying sensor detects that a person is consuming unhealthy food. In an example, this systemic pharmaceutical agent can be released from an implanted reservoir. In an example, this systemic pharmaceutical agent can effect a rapid and temporary reduction in the ability of the intestine to absorb nutrients from food.

In an example, an absorption-reducing member can selectively, temporarily, and automatically reduce absorption of nutrients from unhealthy food by applying electricity to a gastrointestinal organ (or to nerves innervating that organ) when the person consumes unhealthy food. Consumption can be detected by a mouth-based or nose-based food-identifying sensor. In an example, an absorption-reducing member can apply electricity to the external surface of a person's stomach (or to nerves connected to the stomach) in order to temporarily reduce absorption of nutrients from food. In an example, an absorption-reducing member can apply electricity through an electrode.

In an example, an absorption-reducing member can selectively, temporarily, and automatically reduce absorption of nutrients from unhealthy food by modifying gastric motion when a person consumes unhealthy food. This can temporarily increase the speed at which food travels through the gastrointestinal tract. In an example, an absorption-reducing member can change the rate of gastric motility or gastric peristalsis. This can selectively decrease absorption of nutrients from a bolus of unhealthy food.

In an example, an absorption-reducing member can selectively, temporarily, and automatically reduce absorption of nutrients from unhealthy food by applying electricity to an enzyme-secreting organ (or to nerves connected to that organ) when a person consumes unhealthy food. In an example, this can temporarily reduce secretion of digestive enzymes into the gastrointestinal tract and thereby reduce absorption of nutrients from a bolus of unhealthy food.

In an example, an absorption-reducing member can comprise an electrical stimulation device. In an example, this member can be a neural stimulation or muscle stimulation device. In an example, an absorption-reducing member can selectively apply electrical pulses to a person's stomach, to nerves innervating their stomach, or to other organs or tissues in communication with the person's gastrointestinal tract. In combination with a food-identifying sensor in a person's mouth or nose, selective electrical stimulation in response to consumption of unhealthy food can selectively reduce absorption of nutrients from unhealthy food while allowing normal absorption of nutrients from healthy food.

In an example, an absorption-reducing member can selectively, temporarily, and automatically reduce absorption of nutrients from unhealthy food by constricting the size of a portion of the person's gastrointestinal tract when the person consumes unhealthy food. Such consumption can be detected by a mouth-based or nose-based food-identifying sensor. An absorption-reducing member can selectively, temporarily, and automatically reduce food absorption by restricting the size of a portion of the person's gastrointestinal tract.

In an example, an absorption-reducing member can constrict the size of the opening through which food travels into the stomach only when the person eats unhealthy food. In an example, this constriction can be done by decreasing the size of a gastric band or by inflating the interior of a gastric band around the upper portion of a person's stomach. When a mouth-based or nose-based sensor detects that a person is starting to consume unhealthy food, then this sensor sends signals to a gastric constriction device that constrains the size of the entrance to the stomach. In an example, an absorption-reducing member can constrict the overall size of the stomach with an adjustable-volume device that is external to the stomach wall and presses the stomach wall inward when its volume is increased. In an example, such constraints can change the speed at which a bolus of food travels through the gastrointestinal tract and can change the amount of nutrients absorbed from this bolus of food.

In an example, an absorption-reducing member can selectively, temporarily, and automatically reduce absorption of nutrients from unhealthy food by selectively: directing unhealthy food through a short (bypass) pathway in the gastrointestinal tract; and directing healthy food through a long (normal) pathway in the gastrointestinal tract. Such selective direction is made possible by communication between a mouth-based or nose-based food identification sensor and an absorption-reducing member.

For example, most gastric bypasses in the prior art are permanent and blindly reduce absorption of nutrients from healthy food as well as unhealthy food. As a result, sometimes people with gastric bypass operations suffer from deficiencies of key nutrients and have to take supplements for the rest of their lives. It would be advantageous if a device and method for weight loss could selectively decrease absorption of nutrients from unhealthy food but allow normal absorption of nutrients from healthy food. This can allow weight reduction without deficiencies of key nutrients.

The device and method disclosed herein can solve this problem and meet this need. In an example, an absorption-reducing member can selectively reduce food absorption of unhealthy food by selectively directing unhealthy food down a shorter (bypass) path with lower absorption and directing healthy food down a longer (normal) path with higher absorption. In an example, an absorption-reducing member can include an adjustable valve mechanism that is in communication with a food-identifying sensor in the person's mouth or nose.

When a food-identifying sensor detects that a person is eating unhealthy food, then an adjustable valve can be moved to a position that directs food through a shorter (bypass) digestive path. When the sensor detects that a person is eating healthy food, then the valve can be moved to a position that directs food through a longer (normal) digestive path. This avoids the deficiencies of key nutrients and vitamins that sometimes follow bariatric procedures in the prior art. In an example, a gastric bypass can be created, but an adjustable valve is used so that only unhealthy food is routed through this bypass. An absorption-reducing member selectively directs the flow of unhealthy food through the shorter (bypass) route and directs healthy food through the longer (normal) route.

In an example, an absorption-reducing member can include an adjustable food valve or chyme valve that directs unhealthy food or chyme through a bypass that avoids the duodenum and directs healthy food or chyme through a normal path that includes the duodenum. Adjusting and differentiating the digestion pathways of unhealthy versus healthy food is made possible by interaction between a mouth-based or nose-based food identification sensor and an absorption-reducing member.

In an example, when a food-identifying sensor detects that a person is eating unhealthy food, then the sensor can send a wireless signal to an absorption-reducing member that includes a valve control mechanism. This valve can route a bolus of unhealthy food through a shorter (bypass) route. When the person stops eating unhealthy food and starts eating healthy food, then a sensor detects this and changes the valve so that healthy food goes through the longer (normal) route. In various examples, an absorption-reducing member can include one or more valves selected from the group consisting of: biochemical valve, biological valve, electromagnetic valve, electromechanical valve, electronic valve, helical valve, hydraulic valve, MEMS valve, micro valve, microfluidic valve, and piezoelectric valve.

In an example, an absorption-reducing member can be implanted within a person's abdominal cavity. In various examples, an absorption-reducing member can be configured to be implanted in a subcutaneous site, in an intraperitoneal site, within adipose tissue, and/or within muscular tissue. In various examples, an absorption-reducing member can be configured to be attached to, or in fluid communication with, a body member that is selected from the group consisting of: stomach, duodenum, jejunum, ileum, caecum, colon, and esophagus. In various examples, an absorption-reducing member can be configured to be attached to a nerve that innervates a body member selected from the group consisting of: stomach, duodenum, jejunum, ileum, caecum, colon, and esophagus. In various examples, an absorption-reducing member can be attached or implanted by one or more means selected from the group consisting of: suture, staple, adhesive, glue, clamp, clip, pin, snap, elastic member, tissue pouch, fibrotic tissue, screw, and tissue anchor.

In various examples, an absorption-reducing mechanism can be can be made from one or more materials selected from the group consisting of: cobalt-chromium alloy, fluoropolymer, latex, liquid-crystal polymer, nylon, perflouroethylene, platinum, polycarbonate, polyester, polyethylene, polyolefin, polypropylene, polystyrene, polytetrafluoroethylene, polyurethane, polyvinyl chloride, pyrolytic carbon material, silicon, silicone, silicone rubber, stainless steel, tantalum, titanium, and urethane.

As shown in FIGS. 7 through 10, this invention can be embodied in a device for selectively and automatically reducing the absorption of selected types of food in a person's gastrointestinal tract. This device can comprise: (a) a food-identifying sensor that selectively detects when a person is consuming or digesting selected types of food, wherein this food-identifying sensor is configured to be implanted or attached within the person's oral cavity, the person's nasal cavity, or tissue surrounding one of these cavities; and (b) an absorption-reducing member that is implanted within the person's body, wherein this absorption-reducing member can selectively and automatically reduce the absorption of food within the person's gastrointestinal tract when the sensor detects that the person is consuming or digesting selected types of food.

As shown in FIGS. 7 through 10, this invention can be embodied in a method for selectively and automatically reducing the absorption selected types of food in the gastrointestinal tract. This method can comprise: (a) selectively and automatically detecting when a person is consuming or digesting selected types of food by means of a sensor that is configured to be implanted or attached within the person's oral cavity, the person's nasal cavity, or tissue surrounding one of these cavities; and (b) selectively and automatically reducing the absorption of food within the person's gastrointestinal tract by means of an implanted absorption-reducing member, wherein this member selectively and automatically reduces food absorption when the sensor detects that the person is consuming or digesting selected types of food.

In various examples, this invention can be embodied in a device and method to selectively, temporarily, and automatically interfere with the absorption of nutrients from unhealthy food in a person's gastrointestinal tract while allowing normal absorption of nutrients from healthy food in the person's gastrointestinal tract. In an example, this invention can function like an artificial secretory organ that selectively reduces absorption of unhealthy food within a person's gastrointestinal tract without depriving the person of important nutrients from healthy food. In an example, such a device can selectively differentiate between consumption of unhealthy food and healthy food.

In an example, such a device can selectively reduce absorption of unhealthy food and allow normal absorption of healthy food. In an example, this discriminatory ability can be adjusted or programmed to change the types and/or quantities of food which are classified as unhealthy versus healthy. Such a device and method with food discrimination capability can be superior to bariatric surgery and malabsorption devices in the prior art that are blind to whether a selected bolus of food traveling through the gastrointestinal tract is healthy or unhealthy. This device and method can avoid the deficiencies concerning essential nutrients that can occur with food-blind malabsorption devices and methods in the prior art.

I claim:

1. A device for selectively and automatically reducing the absorption of selected types of food in a person's gastrointestinal tract comprising:
   a food-identifying sensor that selectively detects when the person is consuming and/or digesting selected types of food;
   a first absorption-reducing substance configured to be released into the interior of the person's gastrointestinal tract to temporarily reduce absorption of nutrients from food by the gastrointestinal tract;
   a second absorption-reducing substance configured to be released into the interior of the person's gastrointestinal tract to temporarily reduce absorption of nutrients from food by the gastrointestinal tract and the second absorption-reducing substance is different from the first absorption-reducing substance;
   an implanted reservoir, wherein the reservoir has a first compartment that contains the first absorption-reducing substance, wherein the reservoir has a second compartment that contains the second absorption-reducing substance, wherein the reservoir is configured to be implanted within the person's body, and wherein there is an opening or lumen through which the first and/or second absorption-reducing substances are released from the reservoir into the interior of a portion of the person's gastrointestinal tract; and
   a release-control mechanism that controls the release of the first and second absorption-reducing substances from the reservoir into the person's gastrointestinal tract, wherein the release-control mechanism is configured to selectively and automatically increase the release of the first and/or second absorption-reducing substances when the food-identifying sensor detects that the person is consuming and/or digesting selected types of food; and wherein the release-control mechanism is configured to release the first and second absorption-reducing substances in response to consumption of different types or quantities of food as determined by the food-identifying sensor, so that different combinations of the first and second absorption-reducing substances can be released to create specific and/or unique synergistic effects.

2. The device in claim 1 wherein the food-identifying sensor is configured to selectively discriminate between consumption and/or digestion of unhealthy food and consumption and/or digestion of healthy food.

3. The device in claim 2 wherein unhealthy food is identified as having a high concentration of one or more nutrients selected from the group consisting of: sugars, simple sugars, simple carbohydrates, fats, saturated fats, cholesterol, and sodium.

4. The device in claim 2 wherein unhealthy food is identified as having a large amount of one or more nutrients selected from the group consisting of: sugars, simple sugars, simple carbohydrates, fats, saturated fats, cholesterol, and sodium.

5. The device in claim 1 wherein the food-identifying sensor is selected from the group consisting of: chemical sensor, biochemical sensor, accelerometer, amino acid sensor, biological sensor, camera, chemoreceptor, cholesterol sensor, chromatography sensor, EGG sensor, electrolyte sensor, electromagnetic sensor, electronic nose, EMG sensor, enzyme-based sensor, fat sensor, flow sensor, particle size sensor, peristalsis sensor, genetic sensor, glucose sensor, imaging sensor, impedance sensor, infrared sensor, interferometer, medichip, membrane-based sensor, Micro Electrical Mechanical System (MEMS) sensor, microfluidic sensor, micronutrient sensor, molecular sensor, motion sensor, muscle activity sensor, nanoparticle sensor, neural impulse sensor, nutrient sensor, optical sensor, osmolality sensor, pH level sensor, pressure sensor, protein-based sensor, reagent-based sensor, smell sensor, sound sensor, strain gauge, taste sensor, and temperature sensor.

6. The device in claim 1 wherein the first or second absorption-reducing substance coats food, food particles, nutrients, and/or chyme in the gastrointestinal tract.

7. The device in claim 1 wherein the first or second absorption-reducing substance temporarily coats a portion of the interior walls of the intestine.

8. The device in claim 1 wherein the first or second absorption-reducing substance binds to food, food particles, nutrients, and/or chyme in the gastrointestinal tract.

9. The device in claim 1 wherein the first or second absorption-reducing substance temporarily binds to a portion of the interior walls of the intestine.

10. The device in claim 1 wherein the first or second absorption-reducing substance temporarily increases the viscosity, increases the thickness, and/or decreases the nutrient permeability of the mucus that covers a portion of the interior walls of the person's intestine.

11. The device in claim 1 wherein the first or second absorption-reducing substance comprises one or more ingredients that are Generally Recognized As Safe (GRAS) under Sections 201(s) and 409 of the Federal Food, Drug, and Cosmetic Act.

12. The device in claim 1 wherein the release-control mechanism can: start or increase the release of the first or second absorption-reducing substance into the person's gastrointestinal tract in response to detection of consumption or digestion of unhealthy types of food by the food-identifying sensor; and/or stop or decrease the release of the first or second absorption-reducing substance into the person's gastrointestinal tract in response to detection of consumption or digestion of healthy types of food by the food-identifying sensor.

13. The device in claim 1 wherein the release-control mechanism can communicate wirelessly with a source external to the person's body.

14. The device in claim 1 wherein the release-control mechanism can be programmed to adjust one or more of the following aspects of its response to the food-identifying sensor: the type of food which triggers decreased food absorption; the quantity of food which triggers decreased food absorption; the time of day, day of the week, or other timing parameter concerning food consumption which triggers decreased food absorption; the effect of the person's past food consumption on decreased food absorption; the effect of the person's caloric expenditure on decreased food absorption; and the effect of a personalized diet plan created for the person by a health care professional.

15. The device in claim 1 wherein different types of absorption-reducing substances are released in response to consumption of different types or quantities of food.

16. The device in claim 1 wherein the first absorption-reducing substance is released in response to consumption of a first type or quantity of food and the second absorption-reducing substance is released in response to consumption of a second type of quantity of food.

17. The device in claim 1 wherein release of the first absorption-reducing substance and release of the second absorption-reducing substance can be combined to create synergistic effects.

18. The device in claim 1 wherein: the first absorption-reducing substance is selected from the group consisting of psyllium, cellulose, avocado oil, castor oil, chitin, chitosan, beta-glucan, coconut oil, corn oil, flaxseed oil, olive oil, palm oil, safflower oil, soy oil, sunflower oil, gelatin, pectin, agar, guar gum, gum acacia, lignin, xantham gum, other insoluble fiber, other soluble fiber, other gum, and other vegetable oil; and the second absorption-reducing substance is different than the first absorption-reducing substance and is also selected from the group consisting of psyllium, cellulose, avocado oil, castor oil, chitin, chitosan, beta-glucan, coconut oil, corn oil, flaxseed oil, olive oil, palm oil, safflower oil, soy oil, sunflower oil, gelatin, pectin, agar, guar gum, gum acacia, lignin, xantham gum, other insoluble fiber, other soluble fiber, other gum, and other vegetable oil.

* * * * *